(12) United States Patent
Zamanakos et al.

(10) Patent No.: US 10,467,780 B2
(45) Date of Patent: Nov. 5, 2019

(54) SYSTEM AND METHOD FOR DATA ANALYTICS AND VISUALIZATION

(71) Applicant: DexCom, Inc., San Diego, CA (US)

(72) Inventors: Georgios Zamanakos, Portland, OR (US); Daniel Justin Wiedeback, Portland, OR (US); Jeffrey Grant Stewart, Chicago, IL (US); Eli Reihman, San Diego, CA (US); David Price, Carlsbad, CA (US); Lauren C. Miller, Chicago, IL (US); Keri Leone, Encinitas, CA (US); Dan Kraemer, Chicago, IL (US); Katherine Eng Kirby, Chicago, IL (US); Greg Kida, Willow Springs, IL (US); Apurv Ullas Kamath, San Diego, CA (US); Adam R. Greene, Portland, OR (US); Rebecca Gimenez, Chicago, IL (US); Sarah Paige Elli, San Diego, CA (US); Rian Draeger, San Diego, CA (US); Shane Philip Delmore, Portland, OR (US); Leif N. Bowman, San Diego, CA (US)

(73) Assignee: DexCom, Inc., San Diego, CA (US)

(*) Notice: Subject to any disclaimer, the term of this patent is extended or adjusted under 35 U.S.C. 154(b) by 0 days.

(21) Appl. No.: 14/874,296

(22) Filed: Oct. 2, 2015

(65) Prior Publication Data

US 2016/0098848 A1  Apr. 7, 2016

Related U.S. Application Data

(63) Continuation of application No. 14/874,188, filed on Oct. 2, 2015.

(Continued)

(51) Int. Cl.
*G06T 11/20* (2006.01)
*A61B 5/145* (2006.01)
(Continued)

(52) U.S. Cl.
CPC .......... *G06T 11/206* (2013.01); *A61B 5/0022* (2013.01); *A61B 5/14532* (2013.01);
(Continued)

(58) Field of Classification Search
CPC .. G06F 19/3487; G06F 19/322; G06F 19/366; A61B 5/14532; A61B 5/7275; A61B 5/742; G06T 11/206
See application file for complete search history.

(56) References Cited

U.S. PATENT DOCUMENTS 6,174,527 B1   1/2001  Wilson et al.
8,233,959 B2   7/2012  Kamath et al.
(Continued)

*Primary Examiner* — Jwalant Amin
(74) *Attorney, Agent, or Firm* — Knobbe Martens Olson & Bear, LLP

(57) ABSTRACT

Systems and methods are described that provide a dynamic reporting functionality that can identify important information and dynamically present a report about the important information that highlights important findings to the user. The described systems and methods are generally described in the field of diabetes management, but are applicable to other medical reports as well. In one implementation, the dynamic reports are based on available data and devices. For example, useless sections of the report, such as those with no populated data, may be removed, minimized in importance, assigned a lower priority, or the like.

22 Claims, 52 Drawing Sheets

Related U.S. Application Data

(60) Provisional application No. 62/060,351, filed on Oct. 6, 2014.

(51) Int. Cl.

| | | |
|---|---|---|
| *A61B 5/00* | (2006.01) | |
| *G16H 15/00* | (2018.01) | |
| *G16H 10/40* | (2018.01) | |
| *G16H 40/63* | (2018.01) | |
| *G16H 20/17* | (2018.01) | |

(52) U.S. Cl.
CPC .......... *A61B 5/7275* (2013.01); *A61B 5/7282* (2013.01); *A61B 5/742* (2013.01); *G16H 10/40* (2018.01); *G16H 15/00* (2018.01); *G16H 40/63* (2018.01); *G06T 2200/24* (2013.01); *G16H 20/17* (2018.01); *Y02A 90/26* (2018.01)

(56) References Cited

U.S. PATENT DOCUMENTS

| | | | |
|---|---|---|---|
| 8,282,549 B2 | 10/2012 | Brauker et al. | |
| 8,700,161 B2 * | 4/2014 | Harel | A61N 1/36007 607/40 |
| 8,890,681 B2 | 11/2014 | Goetz et al. | |
| 9,465,917 B2 | 10/2016 | Soni et al. | |
| 9,504,430 B2 | 11/2016 | Johnson et al. | |
| 9,901,677 B2 | 2/2018 | Estes | |
| 10,136,845 B2 | 11/2018 | Taub et al. | |
| 2007/0033074 A1 | 2/2007 | Nitzan et al. | |
| 2007/0179352 A1 | 8/2007 | Randlov et al. | |
| 2008/0071580 A1 | 3/2008 | Marcus et al. | |
| 2011/0193704 A1 | 8/2011 | Harper et al. | |
| 2012/0059673 A1 | 3/2012 | Cohen et al. | |
| 2013/0338629 A1 * | 12/2013 | Agrawal | A61M 5/1723 604/504 |
| 2014/0032549 A1 * | 1/2014 | McDaniel | G06F 19/3406 707/736 |
| 2014/0039383 A1 * | 2/2014 | Dobbles | A61M 15/008 604/66 |
| 2014/0058749 A1 | 2/2014 | Galley et al. | |
| 2014/0068487 A1 | 3/2014 | Steiger et al. | |
| 2015/0045641 A1 | 2/2015 | Rule | |
| 2015/0241407 A1 | 8/2015 | Ou et al. | |
| 2016/0210430 A1 | 7/2016 | Saleh et al. | |

* cited by examiner

FIG. 14

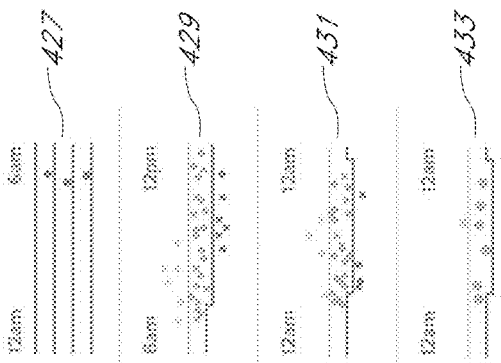
FIG. 15

History of Action Items — 422

| Date | Action | Status |
|---|---|---|
| Aug. 14, 2013 | Lower your insulin prior to dinner by 0.5 U | Completed |
| Aug. 14, 2013 | Lorem ipsum dolor sit amet, consectetur adipiscing elit. Nullam in dui mauris. Vivamus hendrerit arcu. | |
| Aug. 14, 2013 | Etiam at risus et justo dignissim congue. Donec congue lacinia congue. | Completed |
| Aug. 14, 2013 | Etiam at risus et justo dignissim congue. | |
| Mar. 21, 2013 | Lorem ipsum dolor sit amet, consectetur adipiscing elit. Nullam in dui mauris. Vivamus hendrerit arcu. | |
| Dec. 7, 2012 | Lower your insulin prior to dinner by 0.5 U | |
| Nov. 21, 2012 | Lower your insulin prior to dinner by 0.5 U | |
| Oct 7, 2012 | Lorem ipsum dolor sit amet, consectetur adipiscing elit. Nullam in dui mauris. Vivamus hendrerit arcu. | |
| Oct 7, 2012 | Lower your insulin prior to dinner by 0.5 U | |
| Oct 7, 2012 | Lower your insulin prior to dinner by 0.5 U | |

*History of Action Items* — 950

Devices + Usage

Dexcom G4 Platinum — 23.4 AVG HRS PER DAY

617 → CGM ID
- Serial Number: DEX554-334-010313
- Fetched On: Nov. 15, 2013

Alarm Settings
- High Alarm: 200 mg/dL
- Low Alarm: 70 mg/dL
- 90 mg/dL

Statistics
- 7 Day Usage Freq.: 98 %
- 30 Day Usage Freq.: 97%

Meter Company — 4 AVG CHECKS PER DAY

619 → BGM ID
- Serial Number: 34213456789-2234-1
- Fetched On: Nov. 15, 2013

Insulin Pump Company — 22.7 AVG HRS PER DAY

Pump ID
- Serial Number: 87-684PU
- Fetched On: Nov. 15, 2013

Settings
- High Alarm: 260 mg/dL
- Low Alarm: 60 mg/dL
- Correction Factor: 50
- Insulin on Board: 3 hr
- Max Basal Rate: 35.0 u/hr
- Temp Basal Rate: 1.9 u/hr
- Max Bolus Amount: 10.0 u
- Bolus Calculator: On
- Extended Bolus: On
- Dual Bolus: On
- Snooze: On
- Rise/Fall: On

INSULIN TO CARB RATIO
- 12am – 10am: 1/15
- 10am – 12am: 1/18

Statistics
- Avg. Num Bolus/Day: 4
- Avg. Insulin/Day: 34.4 u
- Avg. Bolus/Day: 20 u
- Avg. Basal/Day: 14.4 u
- Basal : Bolus Ratio: 42% : 58%
- Avg. Suspension: 0.8 hr/day
- Avg. Bolus Overrides: 0.7 hr/day
- Override Frequency: 14%
- Avg. Site Change: 3.4 days
- Last Site Change: 4 days ago

Pump Base Rate

621 → PROGRAM 1
- Total Basal: 14.5 u
- 12am – 12pm: 0.8 u

PROGRAM 2
- Total Basal: 13.6 u
- 12am – 8am: 0.5 u
- 8am – 12am: 0.6 u

PROGRAM 3
- Total Basal: 13.6 u
- 12am – 8am: 0.5 u
- 8am – 12am: 0.6 u

PROGRAM 4
- Total Basal: 13.6 u
- 12am – 8am: 0.5 u
- 8am – 12am: 0.6 u

PROGRAM 5
- Total Basal: 13.6 u
- 12am – 8am: 0.5 u
- 8am – 12am: 0.6 u

SYSTEM AND METHOD FOR DATA ANALYTICS AND VISUALIZATION

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 14/874,188, filed Oct. 2, 2015, which claims the benefit of U.S. Provisional Application No. 62/060,351 filed Oct. 6, 2014. The aforementioned applications are incorporated by reference herein in their entirety, and are hereby expressly made a part of this specification.

FIELD

The present disclosure generally relates to data processing of medical measurements of a host, and in particular ways to present such data.

BACKGROUND

Diabetes mellitus is a disorder in which the pancreas cannot create sufficient insulin, such as in the case of Type I diabetes and/or in which insulin is not effective, such as Type 2 diabetes. In a diabetic state, a victim suffers from high blood sugar, which causes an array of physiological derangements, such as kidney failure, skin ulcers, or bleeding into the vitreous of the eye, associated with the deterioration of small blood vessels. A hypoglycemic reaction, such as low blood sugar, may be induced by an inadvertent overdose of insulin, or after a normal dose of insulin or glucose-lowering agent accompanied by extraordinary exercise or insufficient food intake.

A diabetic person may carry a self-monitoring blood glucose (SMBG) monitor, which typically requires uncomfortable finger pricking methods. Due to the lack of comfort and convenience, a diabetic typically measures his or her glucose level only two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is higher or lower based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display, to allow presentation of information to a user hosting the sensor.

Using such systems, glucose values can be immediately displayed to the user. Data from such sensors can also be transmitted to a remote location, and compiled into one or more reports. One problem with such reports is that the same typically have a set report format. The various sections and sub-sections of the report remain the same, whether there is sufficient data to make the section relevant to the user or not. For example, there may not be any insulin data available to generate the report, but the report may have sections that deal with insulin data anyway. This can make the report bulkier, and less comprehensible to the user.

In the same way, static reports can result in presenting information in a way in which important information is either not presented to the user and not presented in a user friendly way. As an example, important recognized patterns could be buried in a report because of the set format. Not only could a user expend considerable time and effort in recognizing the information, but a user could miss the important information altogether.

Moreover, prior art data reporting systems are typically set up with a particular user in mind. This can limit the usefulness of the system to the particular type of person for which the system was designed. For example, the system may be set up for a specialized doctor (e.g. endocrinologist), in which case the system may be designed to provide abundance of detail. However, a new patient may not be able to adequately use the system. Conversely, a simple system that could be useful for new patients may not provide the detail desired by the specialized professional.

In addition, prior art reports tend to follow old conventions that are not necessarily intuitive, and may be difficult to manage efficiently during a doctor-patient visit. The doctor may have to flip around the report while discussing the report with the patient, because information is not provided in a convenient way. Finally, the report may contain a lot of details not relevant to the doctor-patient conversation.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles provide a dynamic reporting functionality that can identify important information and dynamically present a report about the important information that highlights important findings to the user. Systems and methods are generally described in the field of diabetes management, but are applicable to other medical reports as well.

In one aspect, the systems and methods according to present principles provide dynamic reports based on available data and devices. For example, useless sections of the report, such as those with no populated data, may be removed, minimized in importance, assigned a lower priority, or the like.

In general, insights gleaned may be prioritized. Reports may be built that remove sections that are not supported by available data. Reports may also be built in which sections are eliminated or prioritized to highlight information that is believed to be of most relevance to the user of the report. In this way, dynamic reports may be built, constructed, generated, or created based on what is determined to be of importance to the user. That is, systems and methods according to present principles may identify what information would likely be of importance to the user, e.g., based on an analysis of the available data, and may present the findings dynamically, such that important findings are presented and prioritized in the report.

In another aspect, the design of the report may accommodate a variety of user types and use cases. In this way, reports may be provided which are useful for a broad range of users. In one particular implementation, a relatively simple initial view is provided, but the user may be allowed and enabled to "drill down" into details if so desired.

In yet another aspect, reports may be dynamically generated so as to guide a doctor-patient conversation. In this way, the report may be organized so that the same guides the conversation in a logical, flowing manner, reducing the amount of data presented that is unimportant or less important to the discussion.

In yet another aspect, reports may be dynamically generated in such a way so as to effectively coach the patient. In this manner, the report not only points out problem areas, but also celebrates progress. The report can specifically point out where the patient has done well, such as "good days". In the same way, the report need not highlight every problem, but rather identify the most problematic and focus on the same. In a particular implementation, the dynamically generated reports can focus on one particular problem at a time, so as to make user behavior modification more gradual and more convenient. The particular problem focused on may be that which is most problematic.

In yet another aspect, reports may be dynamically generated in such a way as to be more intuitive, not necessarily following old conventions that are less so. Information may be displayed in a way that reflects how the information affects the user/patient. For example, in a glucose/diabetes management implementation, in one implementation, received insulin may be displayed so as to "push down" on the patient's glucose levels, while ingested carbohydrates may be displayed in a way so as to "push up" the patient's glucose levels.

In another implementation, useful information may be generated and displayed about how long particular events are or have been affecting the user's glucose levels. Such "duration" data may be particularly useful in the analysis and prognosis of long-term effects of hypoglycemia or hyperglycemia.

In a first aspect, a method is provided of dynamically reporting data about a user, including: receiving a set of available data about a user, the set corresponding to a first set of available data fields; receiving a default data presentation template, the received default data presentation template having a second set of available data fields and data visualizations based on the second set of available data fields; modifying the default data presentation template, the modifying including: removing data fields from the second set that are not in the first set or are not determinable from the first set, removing data visualizations not determinable from the first set, populating the modified default data presentation template, including the data fields and the data visualizations, with the received set of available data, and displaying the populated modified default data presentation template.

Implementations may include one or more of the following. The receiving a default data presentation template may be preceded by receiving a selection from a user of a default data presentation template. The receiving a selection from a user may be preceded by displaying a set of available default data presentation templates. The data may correspond at least in part to an analyte concentration such as a glucose concentration. The second set may include data fields and data visualizations covering a default time frame, and the modifying may include reducing the second set to only include data fields and data visualizations covering a time frame to which the received available data corresponds. The modifying may include prioritizing the fields and visualizations in the modified default data presentation template, such that upon the displaying, fields and visualizations with a higher priority are displayed above those with a lower priority. The prioritizing may be such that CGM data is given a higher priority than SMBG data. The modifying may include displaying CGM fields if available, and if not, displaying SMBG fields. The default data presentation template may include a data field or visualization corresponding to insulin. The default data presentation template may include a data field or visualization corresponding to events.

The modifying may further include: identifying a pattern in the received data; and modifying the default data presentation template to include a data visualization corresponding to the identified pattern. The identified pattern may include a series of measured glucose values with respect to time. The identifying may include: quantifying a similarity in the received data over two or more periods of time; if the quantified similarity is greater than a predetermined threshold criterion, then identifying the similarity as a pattern. The method may further include prioritizing the data visualizations corresponding to the identified patterns, and may further include displaying the data visualizations corresponding to higher priority patterns above data visualizations corresponding to lower priority patterns. The identified pattern may be selected from the group consisting of: overnight lows, post-meal highs, post-meal lows, time of day highs, time of day lows, weekend versus weekday highs/lows, post event highs/lows, and best days. The method may further include identifying at least one event preceding a pattern, and may further include modifying the default data presentation template to include a data field or data visualization corresponding to the identified at least one event.

The data visualization corresponding to the identified pattern may be a chart, and the data field or data visualization corresponding to the identified at least one event may be an icon placed on the chart. The identifying at least one event may include comparing data about events to predetermined event criteria. The data field or data visualization corresponding to the identified at least one event may include data about a magnitude of the event, an average of similar events, or an amount of time for which the identified event preceded the identified pattern. The method may further include receiving a user entry corresponding to the event, and storing the user entry along with data about the identified event.

The modifying may further include displaying a suggestion based on the received available data, and the suggestion may be further based on a pattern identified in the received data.

The modifying may further include modifying the default data presentation template to include a data visualization corresponding to at least one signal trace of a measured glucose value with respect to time, and may further include displaying an indicator of insulin intake and/or carbohydrate ingestion, and the indicator of insulin intake may be displayed above the at least one signal trace whereby the indicator of insulin intake may be read as "pushing down" on the at least one signal trace, and the indicator of carbohydrate ingestion may be displayed below the at least one signal trace whereby the indicator of carbohydrate ingestion may be read as "pushing up" on the at least one signal trace.

The at least one signal trace of a measured glucose value with respect to time may include a plurality of signal traces corresponding to the measured glucose values with respect to a like time period. The indicator of insulin intake may be quantified and quantized, e.g., basal insulin may be indicated by a constant level on the trace graph and one or more boluses of insulin may be indicated by one or more respective icons at a position with respect to time on the trace graph at which the one or more boluses were caused by the user. If a cessation or reduction in the basal insulin occurs, the basal insulin indication on the trace graph may be correspondingly modified. The method may further include shaping the one or more boluses of insulin to have an extended tail, whereby a length and magnitude of an effect of the bolus is conveyed to a viewer. Similarly, the indicator of carbohydrate ingestion may be quantified and quantized, such that one or more units of carbohydrates are indicated by one or more respective icons at a position with respect to time on the trace graph at which the one or more units of carbohydrates were ingested by the user.

The modifying may further include modifying the default data presentation template to include a data visualization corresponding to at least one signal trace of a measured glucose value with respect to time, the at least one signal trace having a first color, the at least one signal trace being displayed in a second color for values of the signal trace above a predetermined threshold, the at least one signal trace being displayed in a third color for values of the signal trace below another predetermined threshold. The at least one signal trace may include a plurality of signal traces, and the plurality of signal traces may be displayed as part of the data visualization using variability bars. The data visualization may further include an indication of an alarm, the alarm associated with an alarm symbol and an alarm value. The predetermined threshold may correspond to a hyperglycemic level or urgency and the another predetermined threshold may correspond to a hypoglycemic level or urgency. The method may further include causing the predetermined threshold, or the another predetermined threshold, or both, to vary as a function of time of day or patient activity. The patient activity may correspond to eating, bolusing insulin, exercising, or a combination of the above. The method may further include indicating a variation of the predetermined threshold or the another predetermined threshold on the data visualization. The method may further include color coding, or indicating by distinct symbols, the predetermined threshold, or the another predetermined threshold, or both, and/or the variation of the predetermined threshold or the another predetermined threshold, on the data visualization.

The method may further include receiving an entry corresponding to the predetermined threshold, the another predetermined threshold, or both. The entry may be received from a computing environment associated with a health care professional, whereby the health care professional can set thresholds for a plurality of users. The method may further include automatically setting the predetermined threshold and the another predetermined threshold based on one or more factors selected from the group consisting of: age, insurance, type I versus type II, or a glucose control metric. At least a portion of the received available data may correspond to a blood glucose measurement, at least another portion of the received available data corresponds to blood glucose calibration data, and the modifying the default data presentation template to include data visualization may include displaying blood glucose measurement data differently from blood glucose calibration data.

The modifying may include modifying the default data presentation template to include a data visualization, and by hovering over a portion of the data visualization, additional information about the portion may be displayed. The modifying may include modifying the default data presentation template to include a data visualization, and delete by selecting a portion of the data visualization, additional information about the portion may be displayed. The modifying may include modifying the default data presentation template to include a data visualization, and by varying a timeframe, the data visualization may be automatically updated to reflect received data pertaining to the varied timeframe. The portion may correspond to a pattern, and the selection may result in a data visualization being displayed including one or more features selected from the group consisting of: an overview, a multi-day charts illustrating the pattern, a plurality of single day charts illustrating the pattern, and identified event preceding the pattern, and/or a suggestion related to the pattern.

The method may further include receiving an indication of a desired time frame. The indication may be received from user selection of one or more calendar dates. The indication may be received from user selection of an event. The desired time frame may be a first duration of time before the event and a second duration of time after the event. The modifying may include modifying the default data presentation template to include an action item list including a list of entries of action items. The modifying may include modifying the default data presentation template to include a device usage list, the list including a list of entries of devices, and upon selection of an entry from the list additional detail may be displayed about usage of the device.

The modifying may further include modifying the default data presentation template to include a data visualization including compared data, where the compared data compares equivalent data visualizations from two different like time periods. The compared data may include one or more selected from the group consisting of: a chart of a signal trace of a measured glucose value with respect to time, an indicator of device usage, an indicator of an identified pattern, or statistics about the measured data.

The modifying may further include modifying the default data presentation template to include a data visualization including performance data, where a health care professional may view performance of one or more selected patients according to selected criteria, such as criteria selected from the group consisting of: age, weight, sex, insurance, length of time as a patient, type I versus type II, devices used, events, or therapy regimes. The method may further include grouping patients by individual, clinician, or group. The method may further include monitoring patient compliance per group. The method may further include monitoring patient performance per group by comparing patient performance against performance criteria, where the criteria include one or more selected from the group consisting of: A1C, detected patterns, compliance with therapy, and the data visualization may include a comparison of patients that comply with a particular therapy. The displaying may further include printing.

In a second aspect, a non-transitory computer readable medium is provided, including instructions for causing a computing environment to perform the above method.

In third aspect, a method is provided of dynamically reporting data about a user, including: receiving a set of available data about a user, the set corresponding to a first set of available data fields; based on the received set of available data, creating a data presentation template, the created data presentation template having a second set of available data fields or data visualizations corresponding to or generated from the first set; populating the created data presentation template with the received set of available data; and displaying the populated created data presentation template.

Implementations may include one or more of the following. The creating a data presentation template may be preceded by receiving a selection from a user of a desired data presentation template. The receiving a selection from a user may be preceded by displaying a set of available data presentation templates. The data may correspond at least in part to an analyte concentration such as glucose. The second set may include data fields and data visualizations covering a time frame, and the creating may include matching the second set to include data fields and data visualizations covering a time frame to which the received available data corresponds. The creating may include prioritizing the fields and visualizations in the data presentation template, such that upon the displaying, fields and visualizations with a higher priority are displayed above those with a lower priority. The prioritizing may be such that CGM data is given a higher priority than SMBG data. The creating may include displaying CGM fields if available, and if not, displaying SMBG fields. The created data presentation template may include a data field or visualization corresponding to insulin. The created data presentation template may include a data field or visualization corresponding to events.

The creating may include: identifying a pattern in the received data; and creating the data presentation template to include a data visualization corresponding to the identified pattern. The identified pattern may include a series of measured glucose values with respect to time. The identifying may include: quantifying a similarity in the received data over two or more like periods of time; if the quantified similarity is greater than a predetermined threshold criterion, then identifying the similarity as a pattern.

The method may further include prioritizing the data visualizations corresponding to the identified patterns, and may further include displaying the data visualizations corresponding to higher priority patterns above data visualizations corresponding to lower priority patterns. The identified pattern may be selected from the group consisting of: overnight lows, post-meal highs, post-meal lows, time of day highs, time of day lows, weekend versus weekday highs/lows, post event highs/lows, and best days. The method may further include identifying at least one event preceding a pattern, and creating the data presentation template to include a data field or data visualization corresponding to the identified at least one event.

The data visualization corresponding to the identified pattern may be a chart, and the data field or data visualization corresponding to the identified at least one event may be an icon placed on the chart. The identifying at least one event may include comparing data about events to predetermined event criteria. The data field or data visualization corresponding to the identified at least one event may include data about a magnitude of the event, an average of similar events, or an amount of time for which the identified event preceded the identified pattern. The method may further include receiving a user entry corresponding to the event, and storing the user entry along with data about the identified event. The creating may include displaying a suggestion based on the received available data. The suggestion may be further based on a pattern identified in the received data.

The creating may include creating the data presentation template to include a data visualization corresponding to at least one signal trace of a measured glucose value with respect to time, and may further include displaying an indicator of insulin intake and/or carbohydrate ingestion, where the indicator of insulin intake is displayed above the at least one signal trace whereby the indicator of insulin intake may be read as "pushing down" on the at least one signal trace, and where the indicator of carbohydrate ingestion is displayed below the at least one signal trace whereby the indicator of carbohydrate ingestion may be read as "pushing up" on the at least one signal trace.

The at least one signal trace of a measured glucose value with respect to time may include a plurality of signal traces corresponding to the measured glucose values with respect to a like time period. The indicator of insulin intake may be quantified and quantized, such that basal insulin is indicated by a constant level on the trace graph and one or more boluses of insulin are indicated by one or more respective icons at a position with respect to time on the trace graph at which the one or more boluses were caused by the user. If a cessation or reduction in the basal insulin occurs, the basal insulin indication on the trace graph may be correspondingly modified. The method may further include shaping the one or more boluses of insulin to have an extended tail, whereby a length and magnitude of an effect of the bolus may be conveyed to a viewer. The indicator of carbohydrate ingestion may be quantified and quantized, such that one or more units of carbohydrates may be indicated by one or more respective icons at a position with respect to time on the trace graph at which the one or more units of carbohydrates were ingested by the user.

The creating may include creating the data presentation template to include a data visualization corresponding to at least one signal trace of a measured glucose value with respect to time, the at least one signal trace having a first color, the at least one signal trace being displayed in a second color for values of the signal trace above a predetermined threshold, the at least one signal trace being displayed in a third color for values of the signal trace below another predetermined threshold. The at least one signal trace may include a plurality of signal traces, and the plurality of signal traces may be displayed as part of the data visualization using variability bars. The data visualization may further include an indication of an alarm, the alarm associated with an alarm symbol and an alarm value. The predetermined threshold may correspond to a hyperglycemic level or urgency and the another predetermined threshold may correspond to a hypoglycemic level or urgency. The method may further include causing the predetermined threshold, or the another predetermined threshold, or both, to vary as a function of time of day or patient activity. The patient activity may correspond to eating, bolusing insulin, exercising, or a combination of the above. The method may further include indicating a variation of the predetermined threshold or the another predetermined threshold on the data visualization. The method may further include color coding, or indicating by distinct symbols, the predetermined threshold, or the another predetermined threshold, or both, and/or the variation of the predetermined threshold or the another predetermined threshold, on the data visualization.

The method may further include receiving an entry corresponding to the predetermined threshold, the another predetermined threshold, or both. The entry may be received from a computing environment associated with a health care professional, whereby the health care professional can set thresholds for a plurality of users. The method may further include automatically setting the predetermined threshold and the another predetermined threshold based on one or more factors selected from the group consisting of: age, insurance, type I versus type II, or a glucose control metric. At least a portion of the received available data may correspond to blood glucose measurements, at least another portion of the received available data may correspond to blood glucose calibration data, and the creating the data presentation template to include a data visualization may include displaying blood glucose measurement data differently from blood glucose calibration data.

The creating may include creating the data presentation template to include a data visualization, and by hovering over a portion of the data visualization, additional information about the portion may be displayed. The creating may include creating the data presentation template to include a data visualization, and by selecting a portion of the data visualization, additional information about the portion may be displayed. The creating may include creating the data presentation template to include a data visualization, and by varying a timeframe, the data visualization may be automatically updated to reflect received data pertaining to the varied timeframe. The portion may correspond to a pattern, and the selection may result in a data visualization being displayed including one or more features selected from the group consisting of: an overview, a multi-day chart illustrating the pattern, a plurality of single day charts illustrating the pattern, an identified event preceding the pattern, and/or a suggestion related to the pattern. The method may further include receiving an indication of a desired time frame. The indication may be received from a user selection of one or more calendar dates. The indication may be received from a user selection of an event. The desired time frame may be a first duration of time before the event and a second duration of time after the event. The creating may include creating the data presentation template to include an action item list including a list of entries of action items. The creating may include creating the data presentation template to include a device usage list, the list including a list of entries of devices, and upon selection of an entry from the list, additional detail may be displayed about usage of the device.

The creating may include creating the data presentation template to include a data visualization including compared data, where the compared data compares equivalent data visualizations from two different like time periods. The compared data may include one or more selected from the group consisting of: a chart of a signal trace of a measured glucose value with respect to time, an indicator of device usage, an indicator of an identified pattern, or statistics about the measured data.

The creating may include creating the data presentation template to include a data visualization including performance data, where a health care professional may view performance of one or more selected patients according to selected criteria, where the criteria is selected from the group consisting of: age, weight, sex, insurance, length of time as a patient, type I versus type II, devices used, events, or therapy regimes. The method may further include grouping patients by individual, clinician, or group. The method may further include monitoring patient compliance per group. The method may further include monitoring patient performance per group by comparing patient performance against performance criteria, where the criteria include one or more selected from the group consisting of: A1C, detected patterns, compliance with therapy. The criteria may also include compliance with therapy, and the data visualization may include a comparison of patients that comply with a particular therapy.

In a fourth aspect, a non-transitory computer readable medium is provided, including instructions for causing a computing environment to perform the above method.

In a fifth aspect, method is provided of dynamically reporting data about a user, including: receiving a set of available data about a user, the set corresponding to a first set of available data fields; receiving a default data presentation template, the received default data presentation template having a second set of available data fields or data visualizations based on the second set of available data fields; populating the default data presentation template, including the data fields and the data visualizations, with the received set of available data; prioritizing the data fields and the data visualizations in the default data presentation template; and displaying the populated default data presentation template.

Implementations may include one or more of the following. The method may further include modifying the default data presentation template, the modifying including, prior to the prioritizing or displaying: removing data fields from the second set that are not in the first set or are not determinable from the first set and removing data visualizations not determinable from the first set. The prioritizing may include ordering the displayed data fields and data visualizations such that higher priority fields and visualizations are displayed before lower priority fields and visualizations. The prioritizing may include highlighting the displayed data fields and data visualizations such that higher priority fields and visualizations are highlighted differently than lower priority fields and visualizations. The prioritizing may include comparing the populated data fields and data visualizations against a set of criteria. The set of criteria may be entered by a user or may be set by default.

In a sixth aspect, a method is provided of dynamically reporting data about a user, including: receiving a set of available data about a user, the set corresponding to a first set of available data fields; based on the received set of available data, creating a data presentation template, the created data presentation template having a second set of available data fields and data visualizations corresponding to the first set; populating the created data presentation template with the received set of available data; prioritizing the populated data fields and data visualizations; and displaying the populated created data presentation template.

Implementations may include one or more of the following. The method may further include modifying the default data presentation template, the modifying including, prior to the prioritizing or displaying: removing data fields from the second set that are not in the first set or are not determinable from the first set and removing data visualizations not determinable from the first set. The prioritizing may include ordering the displayed data fields and data visualizations such that higher priority fields and visualizations are displayed before lower priority fields and visualizations. The prioritizing may further include highlighting the displayed data fields and data visualizations such that higher priority fields and visualizations are highlighted differently than lower priority fields and visualizations. The prioritizing may further include comparing the populated data fields and data visualizations against a set of criteria. The set of criteria may be entered by a user or may be set by default.

In a seventh aspect, a system is provided for performing any of the methods described below. In yet another aspect, a device, system, and/or method substantially as shown and/or described in the specification and/or drawings are provided.

In an eighth aspect, an electronic device is provided for monitoring data associated with a physiological condition, including: a continuous analyte sensor, where the continuous analyte sensor is configured to substantially continuously measure the concentration of analyte in the host, and to provide continuous sensor data associated with the analyte concentration in the host; and a processor module configured to perform any one of the methods described here.

In a ninth aspect, an electronic device is provided for delivering a medicament to a host, the device including: a medicament delivery device configured to deliver medicament to the host, where the medicament delivery device is operably connected to a continuous analyte sensor, where the continuous analyte sensor is configured to substantially continuously measure the concentration of analyte in the host, and to provide continuous sensor data associated with the analyte concentration in the host; and a processor module configured to perform any one of the methods described here.

In a tenth aspect, method is provided of identifying and reporting events preceding a pattern in a set of user data, including: receiving a set of data about a user; identifying a pattern in the received data, the pattern representing repeating data arrangements in the received data; displaying a data visualization corresponding to the identified pattern; identifying at least one event preceding one or more of the repeating data arrangements; and displaying an indication of the identified event on the displayed data visualization.

Implementations may include one or more of the following. The identifying at least one event may further include identifying at least one event preceding at least a predetermined percentage of the repeating data arrangements. The percentage may be at least 25%, 50%, 75%, 90%, or 99%. The method may further include displaying an icon corresponding to the event on the displayed data visualization. The method may further include displaying data in a window, frame, or layer, corresponding to the event, on or within the displayed data visualization. The data corresponding to the event may include data about a nature of the event, an average amount of time between the event and a start of the pattern, or an effect of the event, or combinations of the above. The method may further include displaying an editable field along with the indication of the identified event, whereby a user can enter and store information about the event. The identifying at least one event may further include comparing an event against one or more criteria to determine if the event pertains to the identified pattern. The data may be a glucose concentration value, and the identifying at least one event may further include identifying at least one increase or decrease in glucose value preceding two or more of the repeating data arrangements.

In an eleventh aspect, a method is provided of displaying data pertaining to user intake of a substance, e.g., one or more units of a substance, including: receiving a first set of data about a user, the first set of data representing an analyte concentration value with respect to time; receiving a second set of data about a user, the second set of data representing user intake of a substance with respect to time; aligning the first and second sets of data with respect to time and displaying the first and second sets of data in one data visualization, where the second set of data is displayed such that an indicator of substances that tend to increase the analyte value is displayed below the first set of data, and an indicator of substances that tend to decrease the analyte value are displayed above the first set of data.

Implementations may include one or more of the following. The second set of data may further represent user intake of one or more units of the substance with respect to time and the second set of data may be displayed such that substances that tend to increase the analyte value are displayed as individual units with a quantity according to the user intake and below the first set of data, and substances that tend to decrease the analyte value may be displayed as individual units with a quantity according to the user intake and above the first set of data. The first set of data may represent a signal trace of glucose concentration and the second set of data may represent insulin intake and/or carbohydrate ingestion, where units of insulin intake may be displayed above the signal trace, whereby the units of insulin intake appear to "push down" on the signal trace, and where units of carbohydrate ingestion may be displayed below the signal trace, whereby the units of carbohydrate ingestion appear to "push up" on the signal trace. The method may further include: receiving a basal value of a medicament, and displaying an indicator of the basal value on the data visualization.

In a twelfth aspect, a method is provided of displaying data pertaining to user analyte concentration values, including: receiving a set of data about a user, the first set of data representing an analyte concentration value with respect to time; receiving at least one threshold value; and displaying the set of data such that the abscissa is time and the ordinate is the analyte concentration value, where the displaying is such that values of the analyte concentration value above the threshold are displayed using a different format than values of the analyte concentration value below the threshold.

Implementations may include one or more of the following. The method may further include displaying an indicator of the received threshold value along with the displayed set of data. The method may further include: receiving at least one alert value and displaying an indication of the at least one alert value along with the displayed set of data. The method may further include: receiving at least one alarm value and displaying an indication of the at least one alarm value along with the displayed set of data. The threshold value may vary with respect to time, including periodically over time, such as where the period is one day. The threshold value may also be entered by a user. The analyte may be glucose, the threshold value may be a default value, and the default value may be determined based on at least one of: user age, user insurance, user type of diabetes, user glucose control metric, A1C value, user mean glucose value, or user mean glucose variability.

In a thirteenth aspect, a method is provided of displaying data pertaining to user analyte concentration values, including: receiving a first set of data about a user, the first set of data representing analyte concentration values with respect to time measured using a first technique; receiving a second set of data about the user, the second set of data representing calibration values of the analyte concentration value with respect to time measured using a second technique, where the first set of data is calibrated based on the second set of data; receiving a third set of data about the user, the third set of data representing values of the analyte concentration value with respect to time measured using the second technique; and displaying the first, second, and third sets of data such that the abscissa is time and a first set of ordinates is the first set of data and another set of ordinates is the third set of data.

Implementations may include one or more of the following. The method may further include displaying a third set of ordinates, the third set of ordinates corresponding to the second set of data, where the ordinates representing the second set of data and the ordinates representing the third set of data are formatted differently. The first set of data may be glucose measurements from a continuous glucose monitor, the second set of data may be calibration measurements from a blood glucose monitor, and the third set of data may be measurements from a blood glucose monitor.

In a fourteenth aspect, a method is provided of displaying data pertaining to user analyte concentration values, including: receiving a first set of data about a user, the first set of data representing an analyte concentration value with respect to time over a first time period; receiving a second set of data about a user, the second set of data representing an analyte concentration value with respect to time over a second time period; and displaying the first set of data as a data visualization and displaying the second set of data as a data visualization, the data visualizations adjacent each other, whereby a user may compare the analyte concentration value over the first time period with the analyte concentration value over the second time period.

Implementations may include one or more of the following. The method may further include identifying a pattern in either the first or second set of received data, or both, the pattern representing repeating data arrangements in the received data, and displaying an indication of the pattern along with the respective data visualization. If the first time period is prior to the second time period, and if a pattern is identified in the first set of data but not the second set of data, then the method may further include displaying an indication that the pattern is not present in the second set of data. The first and second time periods may be selected by default. The method may further include detecting an event in a user calendar, and the first and second time periods may be selected as being before and after the event. The event may be an appointment with a healthcare practitioner. The first and second time periods may be configured to be selectable by a user. The method may further include identifying device usage associated with either the first or second set of received data, or both, and displaying an indication of the identified device usage along with the respective data visualizations. The method may further include identifying a user metric associated with either the first or second set of received data, or both, and displaying an indication of the identified user metric along with the respective data visualizations. The first and second time periods may be determined based on an identified pattern.

In a fifteenth aspect, a method is provided of displaying data about patients in a multi-patient setting, including: receiving in a user interface one or more criteria related to patient data; comparing the one or more received criteria against data records in a database including a set of patient records; and determining and displaying in the user interface one or more patient records that meet the received criteria.

Implementations may include that the one or more criteria are selected from the group consisting of: age, weight, gender, insurance, length of time as a patient, type of malady, devices used to monitor or treat a malady, events associated with patient, a therapy regime, criteria related to user malady treatment performance, or combinations of the above.

In a sixteenth aspect, a method is provided of displaying data about patient compliance in a multi-patient setting, including: receiving in a user interface one or more criteria related to patient compliance with a therapy regime; comparing the one or more criteria against data records in a database including a set of patient records; and determining and displaying in the user interface one or more patient records that meet the received criteria.

Implementations may include that the one or more criteria are selected from the group consisting of: accuracy of device usage, overall time of device usage, accuracy of calibration measurements with respect to a suggested calibration time, user acknowledgement of alarms, accuracy of medicament administration, or combinations of the above.

Advantages may include, in certain embodiments, one or more of the following. Dynamic reports provided by systems and methods according to present principles may coach the patient in a way tailored to the patient or otherwise particularly convenient to the same. The dynamic reports can be dynamically formatted and edited to guide a doctor-patient conversation. Such dynamic reports may not necessarily simply point out problem areas, e.g., highlighting every problem, but can provide a useful tool for patients/users and health care providers/practitioners ("HCP" s) and caregivers to guide disease management. Other advantages will be understood from the description that follows, including the figures.

Any of the features of embodiments of the various aspects disclosed is applicable to all aspects and embodiments identified. Moreover, any of the features of an embodiment is independently combinable, partly or wholly with other embodiments described herein, in any way, e.g., one, two, or three or more embodiments may be combinable in whole or in part. Further, any of the features of an embodiment of the various aspects may be made optional to other aspects or embodiments. Any aspect or embodiment of a method can be performed by a system or apparatus of another aspect or embodiment, and any aspect or embodiment of the system can be configured to perform a method of another aspect or embodiment.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

It is to be understood that both the foregoing general description and the following detailed description are example and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

FIG. 14 is an exemplary user interface of a dynamic reporting system according to present principles, showing a set of patterns determined from CGM data;

FIG. 15 is an exemplary user interface of a dynamic reporting system according to present principles, showing a set of patterns determined from BG data;

FIG. 17 is an exemplary user interface of a dynamic reporting system according to present principles, showing a history of action items;

FIG. 30 shows another exemplary user interface of a dynamic reporting system, for use by an HCP, for monitoring a group of patients;

FIG. 38 shows an exemplary printed dynamic report, in particular illustrating devices and usage;

FIG. 43 shows an exemplary printed dynamic report, in particular illustrating a view of a week's worth of monitored BG trace data;

Like reference numerals refer to like elements throughout. Elements are not to scale unless otherwise noted.

DETAILED DESCRIPTION

Definitions

Figure 1:
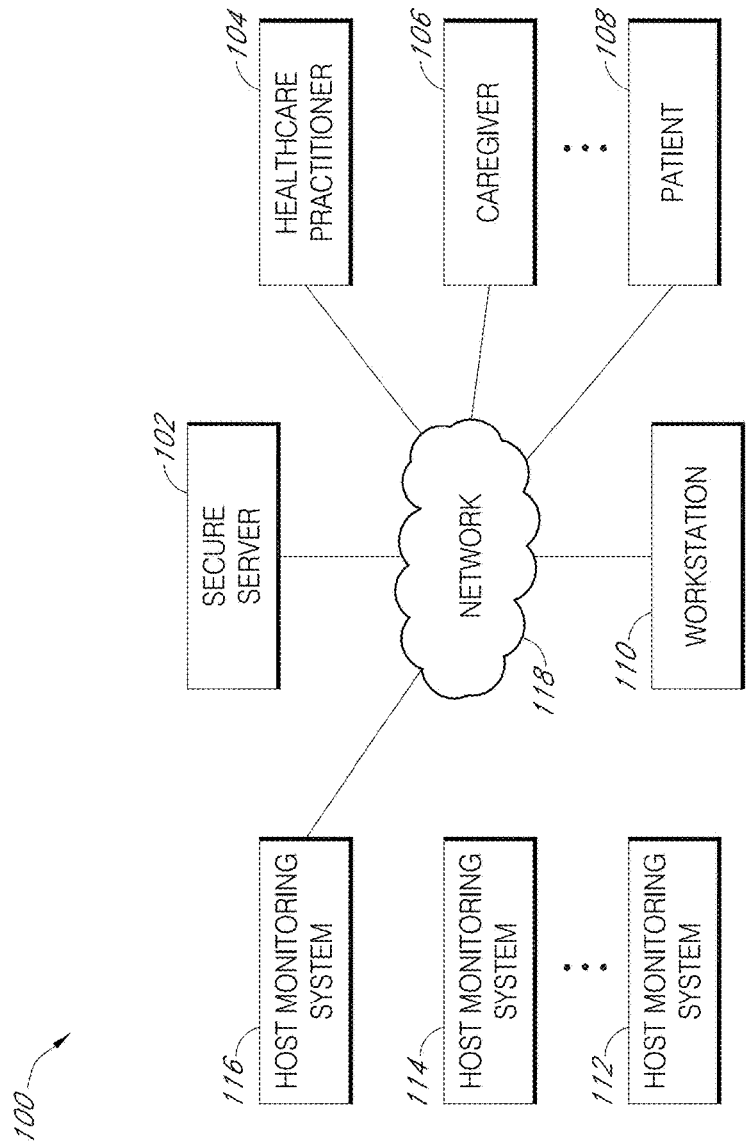
FIG. 1 depicts a high-level system architecture of a remote monitoring system in accordance with some exemplary implementations.

In order to facilitate an understanding of the preferred embodiments, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free B-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The term "RF transceiver" as used herein is a broad term and is to be given its ordinary and customary meaning to a person of ordinary skill in the art (and is not to be limited to a special or customized meaning), and furthermore refers without limitation to a radio frequency transmitter and/or receiver for transmitting and/or receiving signals.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data. In some embodiments, namely, in continuous analyte sensors, calibration can be updated or recalibrated over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified.

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

$$Glucose+O_2 \rightarrow Gluconate+H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, calculating, deriving, establishing and/or the like.

The term "electronic circuitry" as used herein is a broad term and is to be given its ordinary and customary meaning to a person of ordinary skill in the art (and is not to be limited to a special or customized meaning), and furthermore refers without limitation to the components of a device configured to process biological information obtained from a host. In the case of a glucose-measuring device, the biological information is obtained by a sensor regarding a particular glucose in a biological fluid, thereby providing data regarding the amount of that glucose in the fluid. U.S. Pat. Nos. 4,757,022, 5,497,772 and 4,787,398, which are hereby incorporated by reference, describe suitable electronic circuits that can be utilized with devices including the biointerface membrane of a preferred embodiment.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte (or glucose) sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for the continuous analyte sensor, for example a self-monitoring blood glucose meter (SMBG) can be used as a reference for a continuous glucose sensor for comparison, calibration, and the like.

The term "mean" as used herein is a broad term and is to be given its ordinary and customary meaning to a person of ordinary skill in the art (and is not to be limited to a special or customized meaning), and furthermore refers without limitation to the sum of the observations divided by the number of observations.

The term "variation" as used herein is a broad term and is to be given its ordinary and customary meaning to a person of ordinary skill in the art (and is not to be limited to a special or customized meaning), and furthermore refers without limitation to a divergence or amount of change from a point, line, or set of data. In one embodiment, estimated analyte values can have a variation including a range of values outside of the estimated analyte values that represent a range of possibilities based on known physiological patterns, for example.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

The following description and examples described the present embodiments with reference to the drawings. In the drawings, reference numbers label elements of the present embodiments. These reference numbers are reproduced below in connection with the discussion of the corresponding drawing features.

Implementations described herein can include a system and method for dynamic generation of reports about health characteristics of one or more hosts. The health characteristics can include an analyte concentration of a host, such as glucose, or a bodily function, such as heart rate, blood pressure, temperature and the like. In addition, other characteristics of a host can be monitored and reported about to facilitate care of a host, such as a location of the host, state of a host (e.g., exercising, sleeping, or working), medication ingested by the host, meals consumed by the host and the like. The dynamically generated reports can include information about patterns detected in the monitored analyte concentration, steps to take upon detection of a pattern, reasons for patterns, noted events, reasons for events, questions for an HCP, and the like. Generally the term "pattern" relates to a repeating data arrangement identified in received data, e.g., in glucose monitoring, an occurrence of "overnight lows" that commonly occurs with the user.

The health characteristics and other characteristics can be gathered using a host monitoring system that incorporates a computing device, such as a smart phone, and one or more sensors, such a continuous glucose sensor, heart-rate monitor, GPS device, etc. Additionally, a host can manually input information into the computing device or the device can automatically detect or receive inputs, such as meal information, medication administration times and amounts (e.g., from an insulin delivery device), and the like. The information gathered by the host monitoring system can be dynamically reported to the patient or can be transmitted to one or more monitors used by caregivers. The caregiver(s) can then view and print dynamic reports about the host's health condition.

For purposes of illustration only, the following example is a non-limiting exemplary environment in which implementations of remote monitoring systems described herein can be used.

In this exemplary environment, a host having diabetes is monitored by several different caregivers. The host has a continuous glucose monitoring system, such as the DexCom G4® Platinum continuous glucose monitoring system, commercially available from DexCom, Inc., which provides measurements of the host's glucose levels on a display device, such as the DexCom G4® Platinum Receiver, also commercially available from DexCom, Inc.

Further, in this exemplary environment, the display device can be in communication with a gateway device, either via wired communication or wireless communication. The gateway device gathers information, including real-time or near-real-time glucose concentration values, from the display device and transmits the information to a secure server. The gateway device can include a smartphone, such as an iPhone 4S or iPhone 5, each commercially available from Apple, Inc., and a host monitoring software application that comprises instructions configured to cause the smartphone to function as the gateway. The host monitoring software application can be in the form of a so-called "App" downloaded from the Apple App Store operated by Apple, Inc. The gateway can transmit information gathered from the continuous glucose monitoring system wirelessly to the secure server over a cellular network, Wi-Fi network, and the like.

The server can store and monitor the information received from the monitoring system. The monitoring can include comparing glucose values of the host (generated by the continuous glucose monitoring system and transmitted to the server via the gateway) to predetermined thresholds and initiating an action if a threshold is exceeded. For example, the server can compare a current glucose value with a predetermined glucose threshold and initiate a notification, such as a text message over a cellular network, to a monitoring system of an HCP, caregiver, and/or patient, if the glucose value exceeds the threshold. The server can also provide historical and current glucose values to the monitoring system on demand.

The following provides more detail of specific implementations, which may or may not include features noted in the above-discussed exemplary environment.

FIG. 1 depicts a high-level system architecture of an implementation of a monitoring system 100. Here, remote monitoring system 100 includes a plurality of host monitoring systems 112-116 connected to a plurality of caregiver (or patient, host, or user) monitors 104-108 via network 118. Each host monitoring system may be one or more health monitoring devices that gather health-related data, e.g., CGM or BG data, data about insulin or the like, or other data, associated with a host and transmit the health-related data via network 118. Exemplary implementations of host monitoring systems 112-116 are described in more detail elsewhere in this disclosure, but in some implementations can include one or more sensors and computing devices operably coupled to the sensors to gather, process and transmit the health-related data. Network 118 can include any communication medium, such as wired and wireless networks including cellular networks, local area networks, wide area networks, Wi-Fi networks, the internet, and the like. Network 118 can also include one or more servers 102 to process the health-related data received from and transmit notifications and data to one or more caregiver monitors 104-108 either automatically or in response to a request from the caregiver monitors. Each caregiver monitor 104-108 can be associated with an individual or entity that is monitoring the health of one or more of hosts using host monitoring systems 112-116. Each caregiver monitor can be associated with a caregiver, such as parent, spouse, doctor, nurse, hospital and the like, or the patient. The caregiver monitor can include a computing device that receives notifications from network 118 and requests additional information, such as historical health related data generated by one or more host monitoring systems 112-116.

Remote monitoring system 100 of FIG. 1 can also include workstation 110. Workstation 110 may be a computing device, such as a personal computer, that has access to remote monitoring system 100 for configuring settings of system 100 and/or viewing information associated with one or more host monitoring systems 112-116, such as reports dynamically generated by caregiver monitoring systems based on a host's health-related data. Dynamically generated reports may be viewed or printed at a doctor's office, at the patient's home or displayed on a patient's computing device, e.g., smart phone or computer, or the like.

Using the monitoring system 100 of FIG. 1, one or more monitors 104-108 can monitor one or more host monitoring systems 112-116. That is, host monitoring system 112 can be monitored by monitors 104 and 106, and at the same time, monitor 104 can monitor host monitoring system 114 in addition to host monitoring system 112. Various permissions and invitations can be used to limit which caregiver monitors can monitor host monitoring systems.

In one non-limiting example of remote monitoring system 100, each host monitoring system 112-116 comprises a smartphone, such as an iPhone from Apple, Inc., and, likewise, each caregiver monitor 104-108 has a computing device such as a tablet computer, laptop computer, or desktop computer, or a smart mobile telephone, such as an iPhone. Each host mobile telephone has a host software application downloaded from a server of network 118, the application configuring the mobile telephone to perform any of the functions by host monitoring system 112-116 described herein, including gathering and transmitting health-related data used in remote monitoring system 100. The host software application can be an application downloaded using the App Store service hosted by Apple, Inc. Similarly, each caregiver monitor 104-108 has a remote monitoring application downloaded from a server of network 118, the monitoring application configuring to perform any of the monitoring functions including the generation of dynamic reports described herein, including receiving notifications and requesting health-related data of a host. The monitoring application can also be a software application downloaded using the App Store service hosted by Apple, Inc.

Figure 2A:
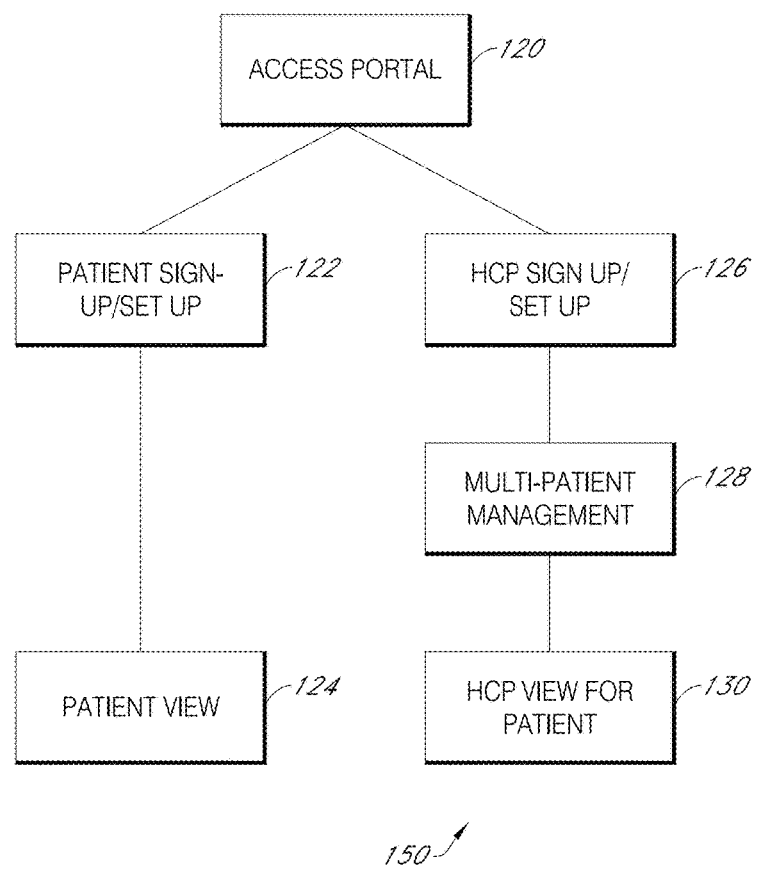
FIG. 2A illustrates a page flow of an exemplary dynamic reporting system according to present principles.

FIG. 2A is a functional block diagram of an exemplary reporting and display system 150 according to present principles. It will be noted that the below described blocks may each constitute a number of pages or portals or subportals, or may further be combined into single pages. That is, the above and below described functional blocks may be implemented as pages in a website or application, portals or subportals to access a webpage or to enter data on a form, links to access webpages or forms, or even as individual buttons on a page. Such are described below in the context of particular implementations, such as blocks, pages, portals, subportals, views, and buttons, but such description is intended to encompass any implementation or combination of implementations, as appropriate and/or desired by the implementer.

Referring back to FIG. 2A, an access portal 120 may provide an initial landing point for access of the dynamic reporting system. A user may then choose to enter a patient sign-up/set up page 122 or a page 126 for HCP sign-up and set up. In some cases, the access portal 120 is not required and each set up page (for users/patients or HCPs) has its own landing page.

If a user or patient is entering the system, the patient sign-up/set up option will be chosen and the patient may be provided with various options to sign-up to the system, edit their profile, set up preferences, or the like. Once such are set up, a page for a patient view 124 may be displayed as a dynamically generated or created report. If the patient has previously entered the system, he or she may be given the option to edit their profile or to confirm their information. Alternatively, upon log in, the patient may be directed to the patient view immediately, with a capability to edit their profile as a menu option. A caregiver for a particular patient may generally use the page 122 to enter the system and review dynamic reports for their subject patient. In the case where the caregiver monitors multiple patients, e.g., a parent of two or more children with diabetes, the caregiver may enter the system through a portal somewhat akin to the HCP portal, enabling viewing and selection of multiple patients.

In many cases the patient view will mirror information provided in the HCP view for an individual patient, although in other cases the HCP view will include additional information primarily useful to the HCP. However, the customizability and dynamic nature of the systems and methods according to present principles will generally allow the patient view to provide equivalent amounts of information, if desired by the patient.

Referring to the right side of FIG. 2A, a similar capability may be provided by page 126 for HCP sign-up and set up. This side of the system will generally have additional functionality, along with individual patient dynamically generated or created reports, and HCPs may generally be enabled to view multiple patients and in many cases all of the patients treated by one or more clinics. Thus, upon HCP login, the HCP may be enabled to manage multiple patients via a multi-patient management page 128. The multi-patient management page 128 may allow a number of operations related to patient management, including summary views of individual patients, the ability to "drill down" to a given patient's more detailed information, overall (cumulative or group) patient disease management, trends, patterns, and the like.

Figure 2B:
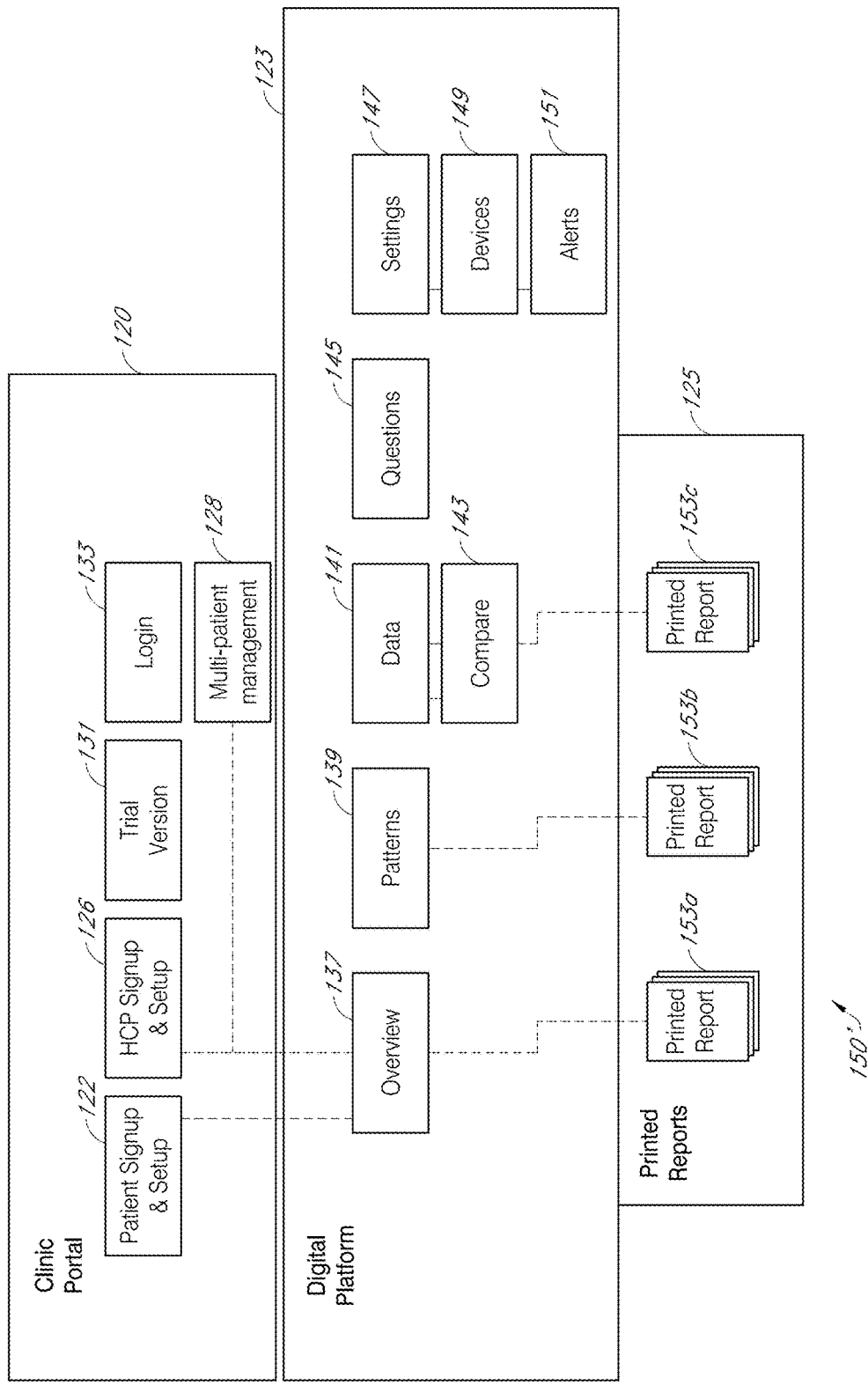
FIG. 2B is a layout of a user interface of a dynamic exemplary reporting system according to present principles.

These aspects are described in greater detail in FIG. 2B, in which the more detailed system 150' includes the patient sign-up and set up page 122 and the HCP sign-up and set up page 126, as well as the multi-patient management page 128. These pages are situated as part of the portal 120 along with a login page 133 and a trial version page 131 allowing new users to download and/or try out the reporting system.

Upon login by a patient or HCP, access is gained to the digital platform 123 which provides a number of functional blocks as shown. These blocks are generally described below, and then a number of examples are given for the use of such blocks, both individually and in combination. By analysis of login information, systems and methods according to present principles may determine the identity of the user logging in, and the identity may further serve as a basis for dynamic generation of a report.

An aspect of systems and methods according to present principles is the dynamic generation of reports, and these reports can be displayed on the screen of a computing device such as a computer or smart phone, and may also be printed for placement in a patient file and/or to guide a doctor-patient conversation. Accordingly, a printed reports system 125 is provided to facilitate the generation of exemplary reports 153a, 153b, and 153c, which may flow from various types of reports in the digital platform 123. The reports 153a, 153b, and 153 are exemplary and generally may represent different report formats, that are predefined or which may be configured by the user according to their desired report style. Exemplary print settings and reports are described below with respect to FIGS. 33-44. The digital platform 123 includes a number of blocks representing links or subportals to different portions of the dynamically created report. An overview block 137 is provided as a quick summary of a patient's condition, and the same identifies information at a high level to provide a summary of the patient's current status. The same can also be employed to provide a summary of the patient's status over a given time frame, which can be a default timeframe, but which can also dynamically vary depending on the amount of data, e.g., historical data, available. The overview block 137 can provide an identification of patterns detected, but generally at a high level, representing the most significant patterns. Additional detail about particular patterns may generally be provided by a patterns block 139. The significant patterns identified and portrayed in the overview block 137 may be ranked or prioritized, as well as selected, based on a number of factors, including available data. A ranking or prioritization, as well as the selection, may also be based on predetermined criteria. In particular, identified patterns may be compared to criteria that have been determined as being pertinent, either to all patients or to that given patient. The criteria for pertinence of a given pattern may be set by the patient, by a caregiver, by an HCP, or may be provided by default (which may in turn be editable). For example, in the context of glucose monitoring, if the patient often encounters overnight lows, detection of a pattern of such may be highlighted in the overview subportal 137 not only due to the relevance to the user but also because of the overall importance of such a pattern in diabetes management, as such patterns are generally noted as being particularly dangerous to users. Patterns may be selected and prioritized in a number of other ways as well. For example, patterns may be selected based on their predominance to a user, e.g., if they are the dominant pattern the user encounters. In some cases patterns are shown if they are of particular educational value to a user, or particularly exemplify a common effect, e.g., a rebound high, where a user's attempt to remedy a low results in a large upward excursion. The dynamic reporting system can also vary the pattern shown to a user so that user interest in such reports is maintained. For example, while particularly dangerous patterns would likely always be shown to a user, one that indicates a smaller area for improvement may be configured to only appear every other week, so that the user is reminded of the potential area for improvement, but the same does not unduly occupy screen or paper "real estate" that could instead be employed for demonstrating other patterns. While of course all patterns could be shown, by selecting certain ones and prioritizing them, the user's attention is drawn to the noted reports without causing fatigue or frustration in the user.

The overview subportal or page 137 may also dynamically change over time based on a number of factors. For example, as additional data is received, the data in fields or visualizations portrayed on the overview page may change to reflect the additional data. Similarly, the data in fields or visualizations derivable from the received data may change as such additional data is received and as such populate fields or visualizations in the overview page.

The availability of data is not the only aspect that can result in dynamic changes to the reports provided on or by the overview page 137. Additional data may lead to additional patterns being recognized, as well as the recognition of events that may have occurred resulting from the new or updated additional data. Additional data may constitute newly received sensor monitoring data, but may also constitute additional data entered by a patient, additional data received from other sensors, e.g., exercise data from accelerometers or GPS data, comments entered by the patient, caregiver, or HCP, data from other medical devices such as medicament pumps, data caused by changes in device settings, and the like. In other cases, the patterns and overview page 137 may also change based on less data being available. For example, the user may no longer use a particular device, or the device may not be providing all the data it previously did due to a malfunction. In yet other cases, data provided by a first device may be supplanted by other data if the other data is "richer" than the data from the first device, e.g., provides more information, is better calibrated, is more useful to the user, or the like. Such a situation may occur when a user adds a CGM to monitoring routine, where they previously used only an SMBG.

In any case, the dynamic reporting may, e.g., automatically adjust and account for cases where the user employs a CGM and pump in their diabetes management, or where just a CGM is employed (e.g., where the pump is defective), or even where just a pump is employed. It will be understood that the above discussion is only exemplary and that numerous variations are possible given this teaching.

Figure 2C:
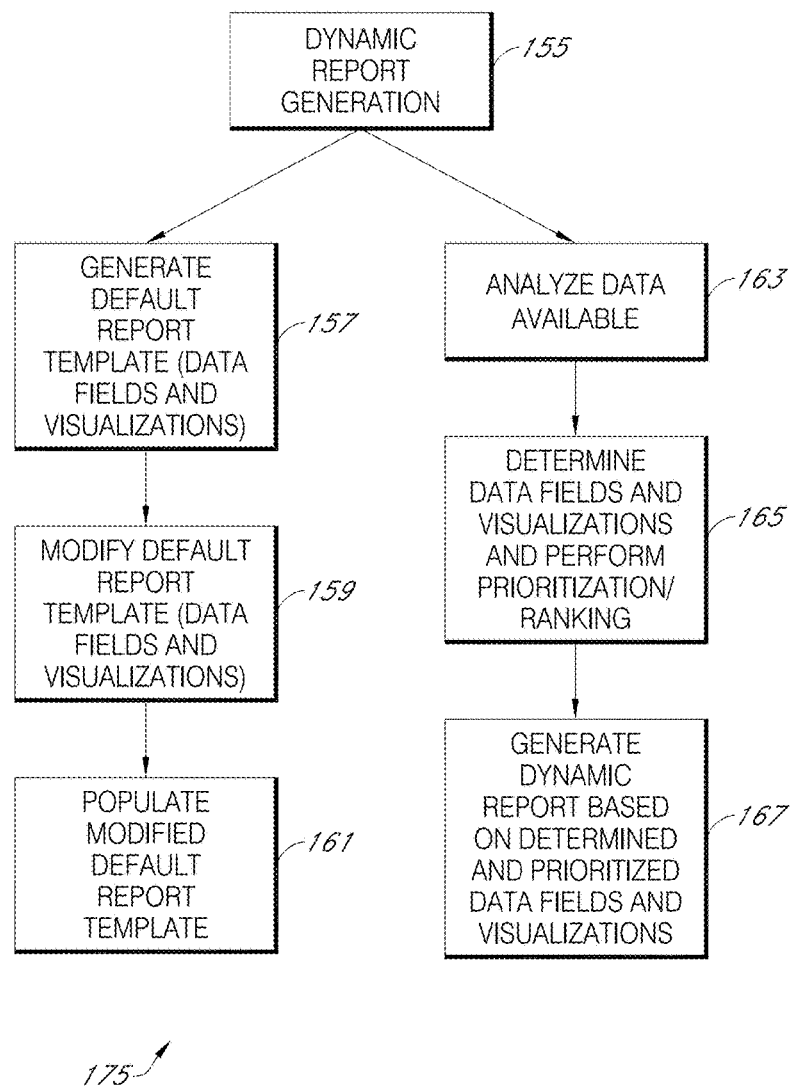
FIG. 2C is a flowchart of a first exemplary method of creating dynamic reports according to present principles.

These aspects are described in greater detail below, but the flowchart 175 of FIG. 2C illustrates at a high level one implementation of a method for dynamic report generation.

In particular, as illustrated in the example of FIG. 2C, a step of dynamic report generation 155 can be performed in at least two ways, one way illustrated by the left side path and another way illustrated by the right side path.

On the left side path, a default report template may be generated (step 157) based on user and system settings. The default report template may include a number of data fields, e.g., glucose measurement value, and a number of data visualizations, e.g., graphical representations of patterns, textual indications of steps to take in response to detected patterns, and the like. The default report template may then be modified (step 159) to reflect available data, user preferences, rankings or prioritizations of data fields and data visualizations, and the like. The modified default report template may then be populated with the data (step 161) and displayed to the patient or other user (or printed, etc.). Thus, on the left side path, a default template is created and then modified.

On the right side path, a default template is not created or employed, but rather the report is generated sui generis based on available data and prioritizations/rankings (and other factors as disclosed). In a first step, data is analyzed to determine what is available and what data or other parameters are derivable from the available data (step 163). In a next step, it is determined what data fields and data visualizations can be constructed (step 165). This step may also include performing prioritizations or rankings as appropriate given user/HCP settings. The dynamic report may then be generated according to the determined data fields and visualizations and prioritization/rankings (step 167).

The above ways of generating dynamic reports are exemplary, and it will be understood that other ways are also possible, including ways that combine the left side path and the right side path.

Referring back to FIG. 2B, selection of a pattern by a user, or selection or activation of a "PATTERNS" button, leads the patient to a patterns block or subportal 139. The patterns block or subportal constitutes one or more pages in which charts may be provided indicating, graphically or textually, patterns that have been detected or identified. To illustrate, patterns can be detected by analyzing a signal trace over time, including comparison with the criteria, e.g., previously identified signal patterns, but the same may also be recognized on a more relative basis, such as patterns detected after meals, patterns detected after exercise, or the like.

Generally the pattern data is a chart illustrating one or more traces (representations of detected signal values) over a timeframe including the detected pattern and a selected amount of time preceding the detected pattern to illustrate provide context as to what factors may have caused or contributed to the detected pattern. Traces can sometimes be portrayed group together by variability bars, which are similar to error bars but generally reflect the variability of the response of a biological system and not an "error" per se. Patterns may be illustrated with a single day's chart being portrayed as an example, or in a chart that represents multiple days' data, using variability bars, multiple traces, or the like. Patterns may also be illustrated with a plurality of single day charts that exemplify the pattern. In a multi-day view, individual days (or other time frames) may be portrayed as thumbnails which upon selection or activation causes display of a corresponding single day chart. Examples of these types are described below.

In systems and methods according to present principles, a dynamic report may be generated so as to illustrate the pattern to the patient or other user in the best way, but without inundating the patient or other user with too much data, e.g., too many views, making it difficult to analyze the pattern. In some cases, traces may be shifted in time so as to better illustrate patterns. For example, if a high-value of a trace occurs 30 min. after breakfast, but the time of breakfast may shift from day-to-day, the trace may shift by the corresponding amount, to indicate more effectively the repeating aspect, that a high occurs 30 min. after breakfast.

Pattern reports may also be dynamically generated based on the amount of data available. In the above example, if a default template would otherwise show a pattern of "high after breakfast" and would show multiple single day charts over the course of Monday-Friday illustrating the pattern, if no data is available for Thursday, then rather than show a blank chart on Thursday, the Thursday chart may be dynamically removed. As noted above with respect to data fields and visualizations in the overview block, patterns displayed in this view may be automatically updated as additional data becomes available or as additional patterns are identified. Other dynamic changes or modifications will also be understood. For example, the data and, e.g., patterns portrayed may form a "sliding window", and a user may slide the window to various other time frames (or expand or contract the window) to investigate and/or examine patterns occurring within these other time frames. It is further noted that additional data input may lead to a dynamic updating of a report, and the same may be especially common when, upon identification of a pattern, a user inputs event data that provides an aspect of causation for a pattern, e.g., a user may enter meal data to explain a pattern of high glucose readings. In this case the report may be dynamically updated in real time to reflect the added data.

By use of the pattern view, users may be enabled to identify events that preceded a pattern, e.g., by recognizing a regular pattern of activity that occurred relative to a pattern of signal traces.

In the case of glucose monitoring patterns, data may be available from a CGM, and data may also be available, either as measured data or as calibration data, from SMBG measurements. In another example of dynamic report generation based on data available, if only one or the other type of data is available, then only that data may be reported. For example, an SMBG chart may be employed when only SMBG data is available, and the same for CGM data. If both are available, both may be reported. If CGM data, e.g., a first set of data measured using a first technique, is available with blood glucose calibration data, e.g., a second set of data using a second technique, then both may be reported, and in some cases on the same chart. In some cases, blood glucose data that is not calibration data may further be displayed on the same chart, such constituting a third set of data. In this case, the blood glucose data used for calibration may be displayed in a different format than the blood glucose data simply displayed for its measurement value. In practical use, if both CGM and SMBG data are available, it may also be common to display only the CGM data, due to its significantly greater richness. If data is available about insulin, e.g., via injection or pump, the same may be displayed as well, as may be carbohydrate or other meal intake as well. Such patterns are illustrated below.

Within the patterns view, the user may also be enabled to selectively apply types of data to charts, as well as time frames over which data in charts are illustrated. A default may be provided and employed. One exemplary such default is that only data believed to be important to the particular pattern is selected, but a user can modify such to allow other types or time frames of data to be displayed. Other defaults may also be employed, including generalized defaults. As one specific example, where a pattern relates to overnight lows, a default may be that meal and insulin data are displayed along with glucose data.

The patterns view may also generate helpful tips that could be used to impact detected patterns. For example, one or more tips may be displayed based on a pattern to either decrease the occurrence of the pattern (if such is a deleterious pattern), or to increase the occurrence of the pattern (if such has been identified as helpful to the patient). As with the pattern charts themselves, the tips may be dynamically created or deleted based on a current status and available data, as well as on device and report settings.

Besides the pattern view, the digital platform 123 may also include a data block or view 141. While the pattern view is largely determinable by the reporting system, the data block allows users and HCPs considerable flexibility in analyzing the data, allowing "power users" the ability to "drill down" to significant levels of detail in data and perform detailed data analysis, for example.

For example, within the data block 141, a "COMPARE" feature may be provided by which a user can compare two time frames of data, e.g., signal traces, patterns, action items, suggested tips, comments, events, devices used, treatments, and/or the like. Where the user is comparing traces, the traces may be over various time periods such as days, or may be compared based on events (as determined by, e.g., detecting an appointment in a user electronic calendar). For example, a first timeframe can be a week prior to beginning a treatment, and the second timeframe can be a week after the beginning of the treatment. The second timeframe may also be a week prior to a doctor's appointment. Other exemplary aspects to compare are described below, and still others will be apparent to one of ordinary skill in the art given this teaching.

A questions block 145 may be provided within the digital platform 123 which allows a user to input questions, which may later be reviewed by their clinician. In some cases, the clinician may be enabled to respond to the questions immediately, e.g., via e-mail or text, or within a response block (not shown) within the dynamic reporting system. Yet other questions may be stored for later discussion between the patient and the clinician during an appointment. A check box or other indicator of completion may be employed by either the patient or the clinician to indicate that the matter has been discussed and the question adequately answered. A clinician or other user may also use a questions block to inquire about disease management aspects of a patient, e.g., about bolusing medication or meal intake.

A settings block 147 may also be employed within the digital platform 123 which allows the user, caregiver, and/or HCP to input and modify settings associated with the patient. The settings block 147 may include editable data fields including user identifying information, clinic information, or the like.

The settings block 147 may also be employed to input target ranges, including a high predetermined threshold and a low predetermined threshold, as thresholds for hyperglycemic and hypoglycemic alerts or alarms, respectively. These thresholds may vary based on time of day, e.g., whether day or night, and/or by patient status, e.g., awake or sleeping. The settings block 147 may also be employed to link to an alerts block 151 that allows a user to enter other alerts and notifications settings, including, e.g., communications means to caregivers (for text messaging alarms or the like). The block may also be employed to enter or modify other communication settings, including communications with outside accounts, e.g., EMR accounts, social networking accounts, or the like.

The settings block 147 may further be employed to indicate usual times for meals, e.g., breakfast, lunch, and dinner, and even within these common meal items. In some cases, common meal items as input in the settings block may in a reporting system be portrayed next to checkboxes, and by a user checking the appropriate checkbox, data about a meal may be entered into the system. By entering meal timing information into the settings block 147, identification of patterns due to meal ingestion may be assisted.

The settings block 147 may also be employed to link to a devices block 149 for a user to enter data about the devices they use for disease management, e.g., SMBGs, CGMs, pumps, or the like. Such device data may then be portrayed in various dynamic reports as will be illustrated below. Additional details about settings are also described below.

Figure 3:
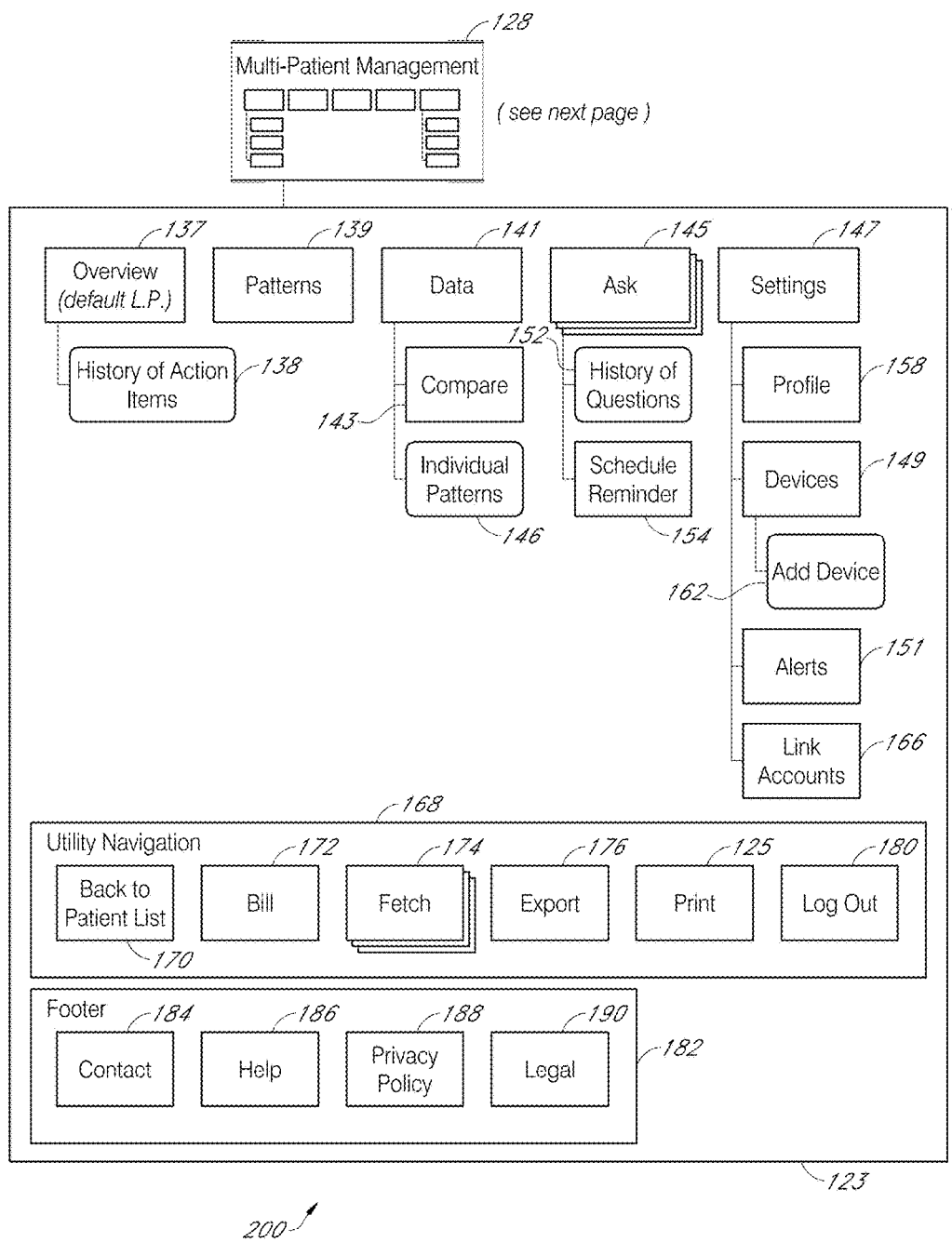
FIG. 3 is a more detailed layout of a portion of an exemplary reporting system according to present principles, which may be employed within the context of either a patient or an HCP view.

FIG. 3 is a functional block diagram of a more detailed view of an exemplary reporting and display system 200 according to present principles, as such may be particularly implemented in an HCP multi-patient setting (although many features are also present in a patient view). The system 200 includes the digital platform 123 which is shown coupled to the multi-patient management block 128 which is described in greater detail in FIG. 4. The digital platform 123 includes a link 138 to a history of action items, which may be implemented in a database, spreadsheet, or the like. Similarly, the platform may include a link 152 to a history of questions, which may be implemented similarly, as well as a link 154 to allow the scheduling of reminders or other calendaring functionality, as well as other doctor-patient communications.

The settings block 147 may include a profile 158 in which a user may enter or edit identifying information, as well as a "LINK ACCOUNTS" block 166 in which patients may be linked with other patients, caregivers or HCPs, or vice versa. Utility functionality may be provided by a utility navigation bar 168. Within the bar 168, a link 170 may be provided back to a list of patients. A link 172 may be provided to access billing/invoicing and payment information. A link 174 may be provided to fetch additional information as needed, such as data from other devices that are communicatively connected. Examples of such other devices may include, e.g., a pump, an SMBG meter, or the like. A link 176 may be provided to export patient data, e.g., in a number of formats, e.g., CSV, as a particular type of database, and so on. A link 125 may be provided to access the print functionality noted above and described in greater detail below.

The print blocks indicated as elements 125 may pertain to either the HCP or the patient view. In general, it may be desirable in many implementations to have the print view be similar to an online, or screen view, so that the patient, caregiver, or HCP need not learn a different set of conventions for one versus the other. Also in many implementations, it may be desirable to have the print view convey just as much information in black and white as in color, so as to enable those without color printers to obtain needed information from a printed report. In addition, black and white reports may be preferred by certain users due to the higher expense of color printing. Modifications to default print settings may be made easily using edit functionality provided within print block 125 or within a print settings block or module within setting block 147. The modifications may include different types of data fields and data visualizations to be printed, but also different overall levels of data, e.g., a simpler printout or display of only key data fields and visualizations, or a complex printout of many data fields and visualizations (perhaps prioritized in order of importance as perceived by the user, patient, caregiver, or HCP). In one exemplary type of report, a one page dynamically generated summary is printed. In another exemplary type of report, a comprehensive multipage dynamically generated report is provided, along with identified pattern pages. In yet another exemplary type of report, a dynamically generated summary page is printed followed by the comprehensive multipage report. In yet another exemplary type of report, daily view options for both CGM and SMBG data may be provided. Other variations will also be understood. For example, and as will be illustrated below, print options may allow for a section for a clinician's notes at the bottom of a page, such being often identified as important for reimbursement as well as being convenient for HCPs that like to go over a printed version of the report with the patient. And as noted HCP-specific print settings and defaults may be employed to set a different default format for each HCP of a practice.

In general, reports may be viewed and printed by users, caregivers, and clinicians, in a number of ways and are generally controllable by the viewer. Such printable reports (which may also be convenient ways to view on-screen reports) are described below in greater detail with respect to FIGS. 35-44.

A button 180 may be provided for logout. A footer bar 182 may be provided to access, enter, and edit data such as: contact information 184, health information 186, a privacy policy 188, and legal information 190.

Figure 4:
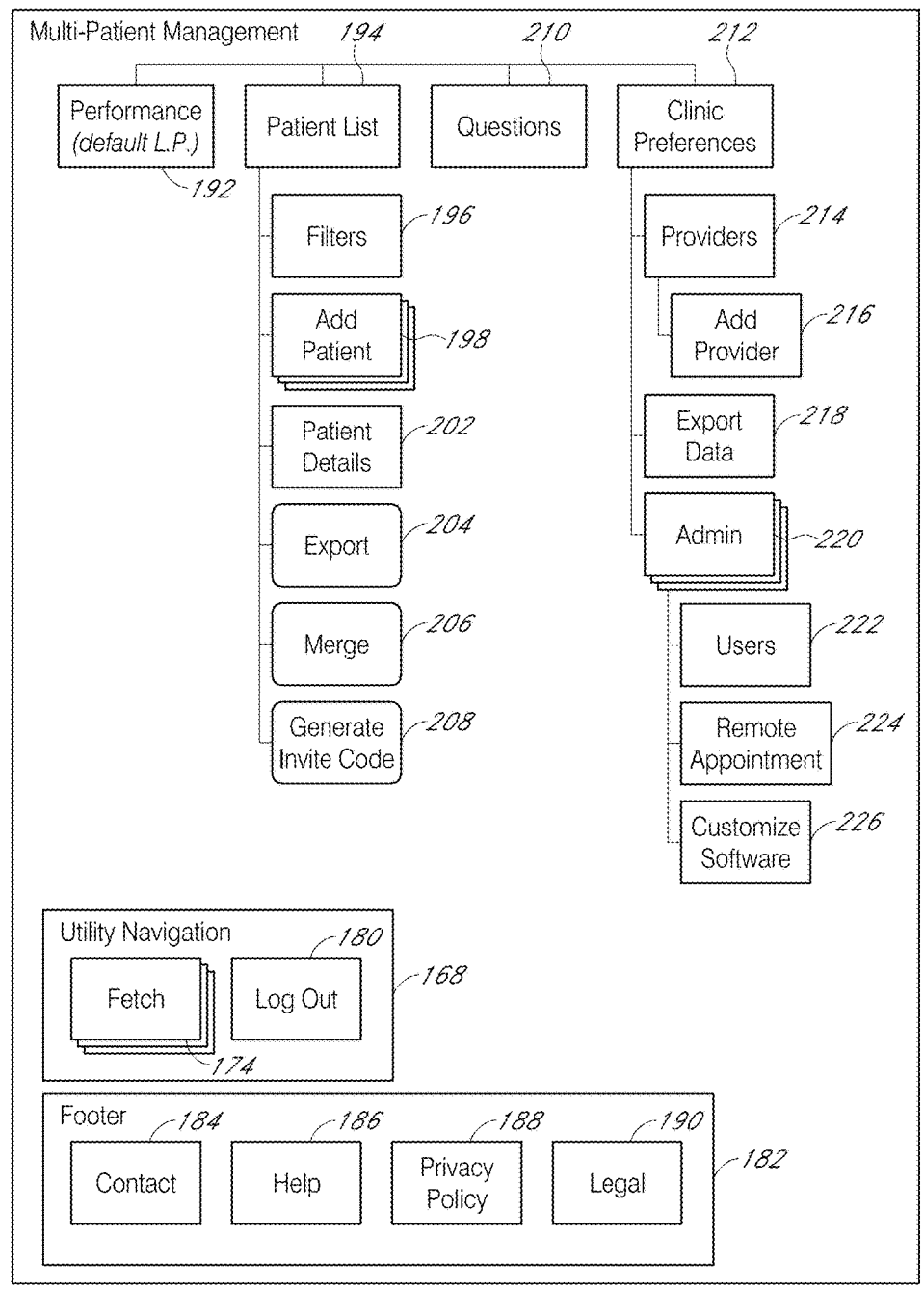
FIG. 4 is a more detailed layout of a portion of an exemplary dynamic reporting system according to present principles, which may be employed within the context of an HCP view.

FIG. 4 illustrates a more detailed view of a multi-patient management block 128. The block 128 includes one or more subblocks including a performance block 192, a patient list block 194, a questions block 210, as well as a clinic preferences block 212.

The performance block 192 is described in greater detail below but here it is noted that the same can be effectively employed to monitor patient compliance and other aspects of patient data and performance. Filtering, e.g., based on criteria, can also be employed to monitor the performance and compliance of subgroups. In this way, the performance or compliance of a single patient may be monitored, as well as that of a group of patients, e.g., based on age, insurance, devices used, patient type (e.g., type I versus type II), how long a user has been a patient of the clinic, or the like.

The patients list block 194 may also include a filtering capability, and can be sorted or arranged in various ways, e.g., patients may be sorted by appointment time, patients may be sorted and identified by their treatment needs, either by specific need or by urgency, patients may be identified and sorted based on which are due for an appointment based on insurance coverage, and so on. The patient list block 194 may further include one or more filtering blocks 196, an ADD PATIENT block 198, a PATIENT DETAILS block 202, an EXPORT block 204, a MERGE block 206, and a GENERATE INVITE CODE block 208. These blocks may be in many cases implemented as buttons on the user interface.

In more detail, the filtering block 196 allows various filters to be applied to the patient list to allow the clinician to focus on one or more types of patients, e.g., on the basis of gender, age, weight, types of devices used, or the like. The add patient block allows 198 patients to be added into the system.

A patient details block 202 allows access to additional details about a given patient, and in many cases leads to the overview and other views described elsewhere in this specification. Upon selection of a patient to view via the patient details block 202, charts and other data about the patient may be displayed. The same may also lead to a performance view of the patient or patients.

The export block 204 allows exporting of patient data, e.g., for billing or EMR purposes or the like. The merge block 206 also allows patient details to be merged, e.g., such as within a family. The generate invite code button 208 allows potential patients to be invited to become part of the patient group associated with a given position or clinic. A code is generated which is sent to the potential patient, and upon acceptance by the potential patient, the same may be monitored within a particular dynamic reporting system. The GENERATE INVITE CODE block may also be employed to allow caregivers to become affiliated with one or more patients.

The questions block 210 provides an overall list of questions which the clinician may then attempt to answer. These questions may be sorted or filtered by patient, so that, e.g., if an appointment is upcoming, the clinician may attempt to have the questions answered by the time of the appointment. In so doing, in another implementation the questions block 210 may enable the sorting of questions according to time of patient appointment.

The clinic preferences block 212 may have several sub blocks or buttons associated with the same, including a providers block 214, which provides access to the providers associated with the particular reporting system, as well as an ADD PROVIDER block 216, allowing addition of new providers. An EXPORT DATA block 218 may be provided to allow export of provider and/or patient data. An ADMINISTRATIVE block 220 may be employed to allow additional functionality, such as to manage users via a users block 222, a remote scheduling functionality provided by REMOTE APPOINTMENT block 224, and a capability to customize software via CUSTOMIZE SOFTWARE block 226. In more simple customization, logos for a particular clinic may be added to the dynamically generated reports. In more detailed customization, the customization may allow functionality not provided by base systems, and may be accomplished in various programming languages, e.g., Visual Basic, JavaScript®, or the like.

The clinic preferences block may also allow additional functionality, not shown. For example, a clinician may set what views to print in preparation for patient appointments, and the same may even be customized per patient. The clinician may enable particular settings for the report, as well as default target glucose ranges they prefer for their patients.

Figure 5:
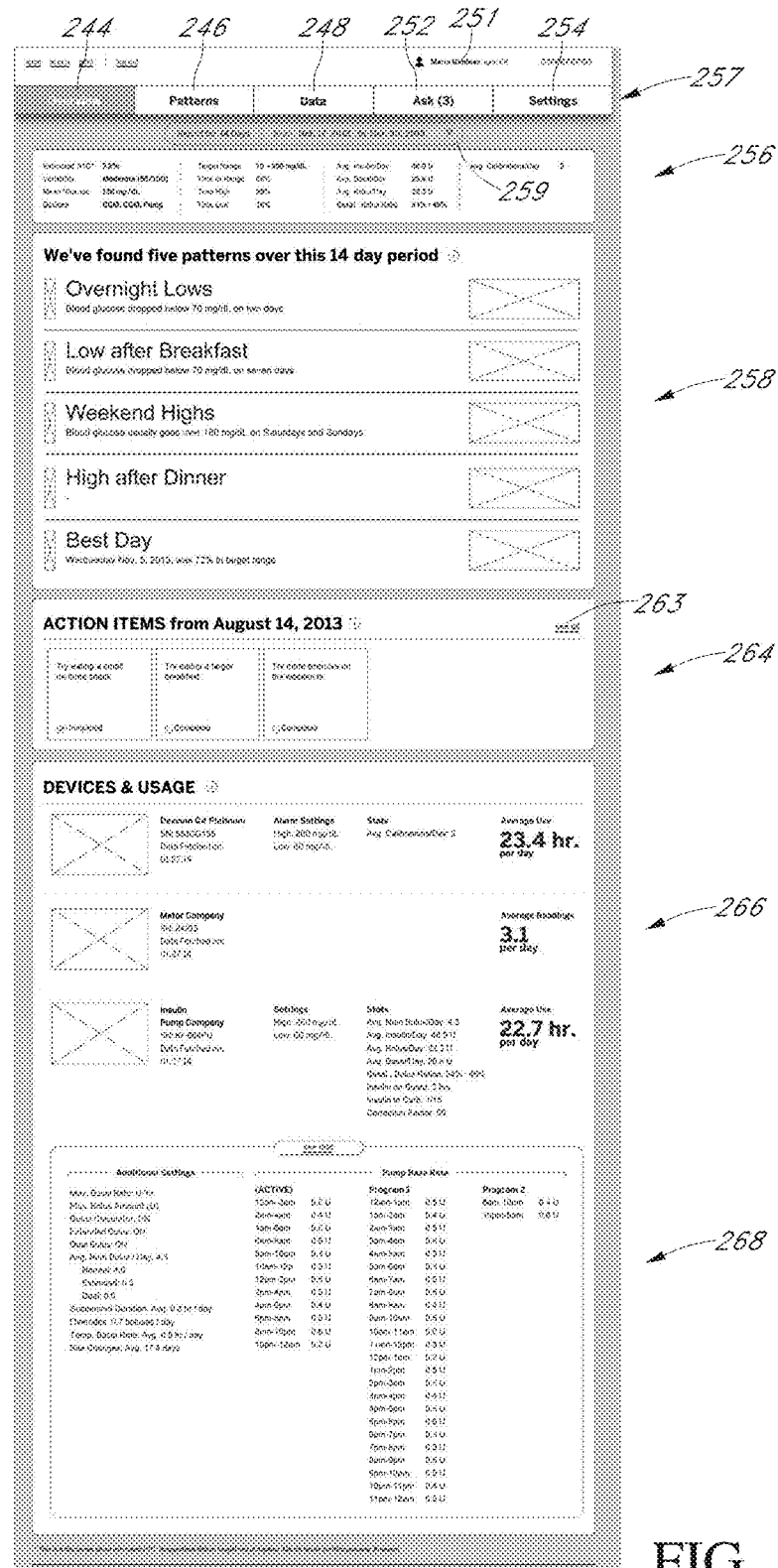
FIG. 5 is an exemplary user interface of a dynamic reporting system according to present principles, showing a CGM overview page including a summary as well as windows pertaining to patterns, action items, and device usage.

The elements described above with respect to the functional blocks in the digital platform are now illustrated below in reference to a number of exemplary user interfaces. One exemplary user interface for the HCP view is shown in FIG. 5, and it will be noted that the patient view may have a similar format.

In the HCP setting, the overview block for a given patient may lead to an overview page 300 in which various aspects are displayed. First, identifying information 251 may be displayed for a patient as well as summary data 256 (described in greater detail below with respect to FIG. 7). A navigation bar 257 may provide links to other page(s) as noted above, including the (same) overview view 244, a patterns view 246, a data or analysis view 248, a questions view 252, and a settings view 254. The patient identifying information, the summary data, and the navigation bar may generally be consistent across views, although the particular data fields and visualizations displayed will change with additional and updated data.

The overview page 300 may also include dynamically generated pattern data 258, which patterns may be dynamically generated based on available data, prioritizations and rankings, or the like. In FIG. 5, patterns shown include overnight lows, lows after breakfast, weekend highs, highs after dinner, as well as a patient's "best day" (which provides positive reinforcement by noting one or more or a pattern of days in which the patient's disease management was under particularly good control). The pattern data may be based on the time period selected by default or by the patient, which time period is displayed in the timeframe bar 259. The timeframe bar 259 identifies the timeframe of data being analyzed, and can be modified to a different timeframe upon user choice. A different timeframe would generally result in an overview page with different data fields and data visualizations displayed. As noted above the time period may be selected by default or by the patient, and may also be determined based on available data. That is, if data is not available for a given time frame, that data may not be displayed (as opposed to, e.g., displaying a blank chart).

By analysis of data, patterns may be identified and selected (or not) for inclusion in the report. Patterns may also be prioritized or ranked such that they appear higher in the report. The selection and ranking may be according to predetermined criteria. For example, criteria may include a prioritized listing of patterns, prioritized by order of seriousness. The patterns, if present, may then be dynamically prioritized according to the list. The list may also weight the patterns according to the degree of excursion outside of target range.

The display patterns may not only be areas for patient improvement, but can also indicate patterns where the patient did well, providing positive reinforcement for the patient, e.g., indicating their "best day" or indicating an improvement such as the patient's glucose value not going high after a meal. Selecting a given pattern on the overview page 300 may cause the pattern view to open, showing the selected pattern in additional detail.

The overview page 300 further illustrates a window 264 for action items. These action items may include specific steps or tips which have been identified by the system as being potentially of use in helping patients manage their disease. The overview block 137 may also be linked to a database or history of prior action items 138 (see FIG. 3). Such may be obtained in the user interface of FIG. 5 by selection or activation of link 263. By providing convenient access to the history of action items, clinicians may be conveniently prompted to discuss patient status and to follow-up with patients on such actions which had been previously set for the patient.

The overview page 300 further illustrates a window 266 related to devices and their usage, as well as a window 268 for additional information about devices and their usage. In this window can be listed devices used within the selected timeframe and associated information, e.g., CGM's, BGs, insulin pumps, and the like. The device usage can include the average number of calibrations per day for devices that need to be or can be calibrated, such as a continuous glucose sensor.

In some implementations, reporting system 150 can also identify and report if device usage guidelines have not been satisfied. For example, if a device is supposed to be calibrated twice a day per usage guidelines, the reporting software 150 can identify if data indicates the device was calibrated less than two times a day, and on which days. One way to do this is for the reporting software 150 identify how often the device is supposed to be calibrated (e.g. once every 12 hours), analyte the data over the report timeframe for calibrations that comply with the requirements (with some acceptable margin, such as two or three hours), and flag and report any day in which the data indicates the usage does not comply.

Figure 6:
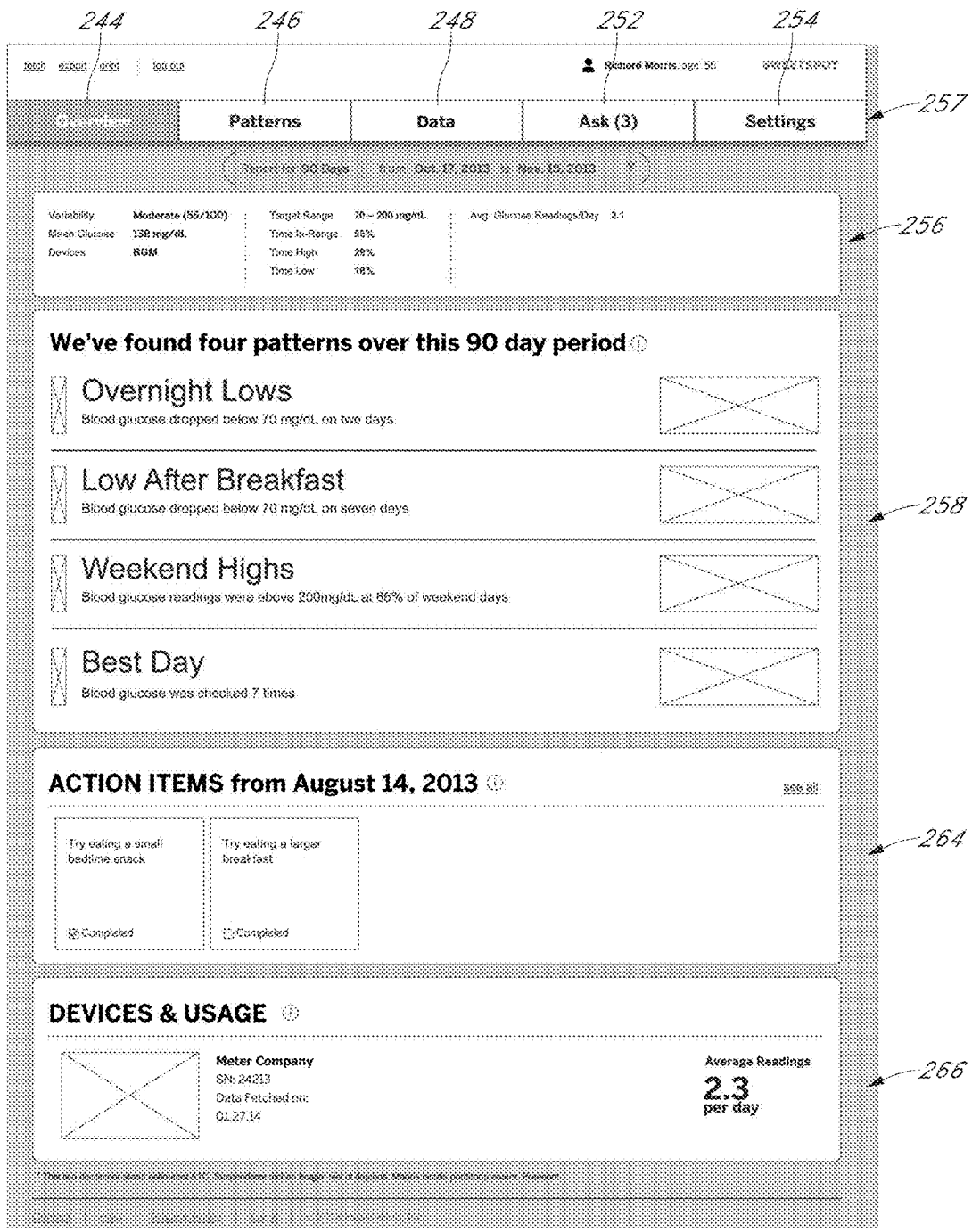
FIG. 6 is an exemplary user interface of a dynamic reporting system according to present principles, showing a BG summary as well as windows pertaining to patterns, action items, and device usage (according to dynamic reporting principles herein, in some cases fewer data fields and visualizations will be shown as compared to reports incorporating CGM data)

FIG. 6 illustrates another exemplary overview page 350, but where only SMBG data is available. The overall structure is similar to the CGM overview page of FIG. 5, but many of the fields that may apply only when CGM data is available are not provided in the SMBG view. However, it should be noted that instead of creating a particular "BG view", the same is rather dynamically generated by consideration of the available data, which may be CGM, BG, or a combination. Where both are available, the dynamic reporting system and method according to present principles may give preference to CGM data, or to SMBG data, or may highlight one versus the other. If only one has data available, that data may be displayed.

As with the CGM data, selection of particular features, such as patterns or action items may lead to additional information being displayed about the selected feature. For example, if the pattern of overnight lows is selected, the displayed result may be one or more charts illustrating traces occurring during nighttime in which the low signal value is seen.

Figure 7:
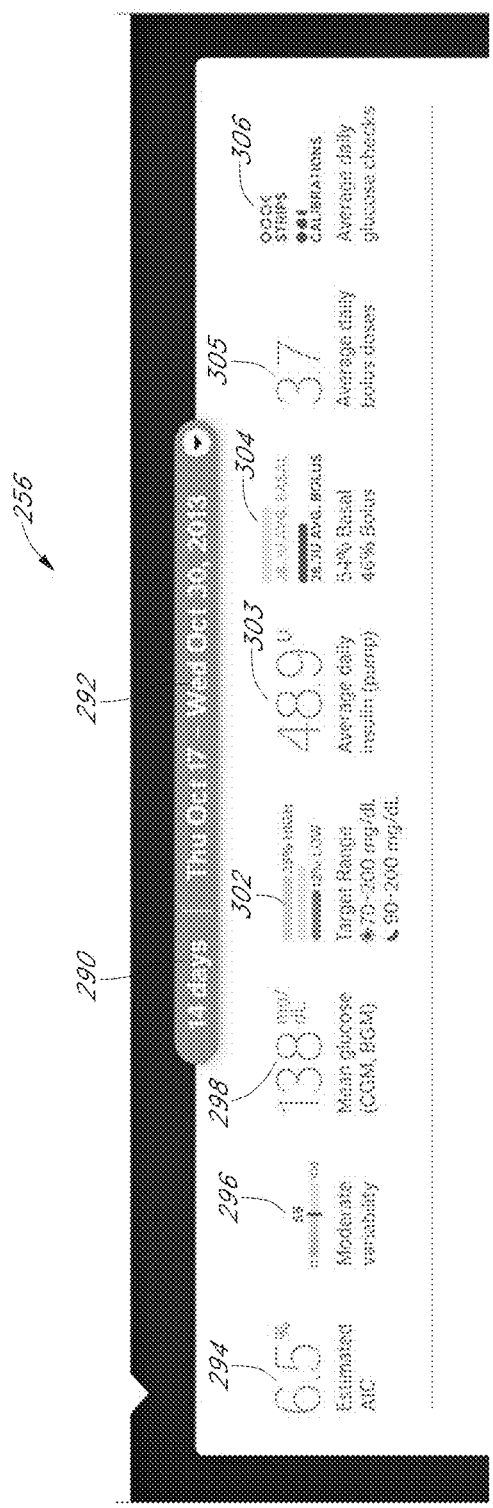
FIG. 7 is a more detailed exemplary user interface of a dynamic reporting system according to present principles, showing a CGM summary.

FIG. 7 illustrates an exemplary summary section or window 256, which includes timeframe information, including a number of days 290 covered by the summary as well as the specific dates spanned by the timeframe 292. The summary section 256 can include a number of different displayed parameters of use to the patient, caregiver, or HCP.

In the specific exemplary implementation of FIG. 7, the summary section 256 includes an estimated A1C value 294. Such estimated A1C values may be calculated from algorithms using CGM data, SMBG data, as well as in other ways. This value provides an overall picture of diabetes management over a period of 2 to 3 months. The summary can also provide an indication of the variability 296, e.g., on a scale of 0 to 100, indicating textually and/or graphically how variable the patient's glucose value has been over the given timeframe, a mean value of such glucose level being illustrated by an element 298.

The summary section 256 may also include a target range element 302, the threshold values of which being input by the patient, a caregiver, or an HCP, or provided by default. The target range element 302 may also include an indication of how often or how much time the patient has been outside of the target range, either generally or specifically, as shown, e.g., by a percentage above the range and a percentage below the range. The target range element 302 may further be displayed in a more granular way, if different portions of the day are provided with different threshold levels, e.g., where nighttime "low" thresholds are specified to be different from daytime thresholds. Generally thresholds can vary, including in an automatic periodic fashion, such as the noted daily variation where nighttime thresholds are different from daytime thresholds. Further, the thresholds can vary by manual changes, such as a user or healthcare practitioner changing one or more thresholds. Thresholds may also be provided with an initial default value or changed to a default value, where the default value is determined based on, e.g., user age, user insurance, user type of diabetes, user glucose control metric, A1C value, user mean glucose value, or user mean glucose variability.

The summary section 256 may also include an element 303 indicating average daily insulin pump usage, e.g., by units of insulin, if such insulin pump data is available. Such data may be accompanied by other related data, including average amounts of basal and bolus insulin 304, as well as percentage breakdown, and average number of daily boluses 305. Also shown is an average daily number of glucose checks 306, where the "strips" visualization relates to the number of non-calibration related SMBG checks performed on average per day (e.g., for dosing or informational purposes), while the "calibration" visualization is the average number of calibrations of the CGM the user performed in a day. It is again noted that the above types of data are those measured within the selected timeframe, and that in each case the above noted data types may be provided by dynamic generation of the report, including omission of such data types in the presentation and display of certain fields and visualizations if such data types are unavailable, are underivable from available data, or do not merit display if dictated by the prioritization or ranking scheme.

Additional data may be used in the calculation of elements within the summary section, or may provide separate elements for display themselves.

Figure 8:
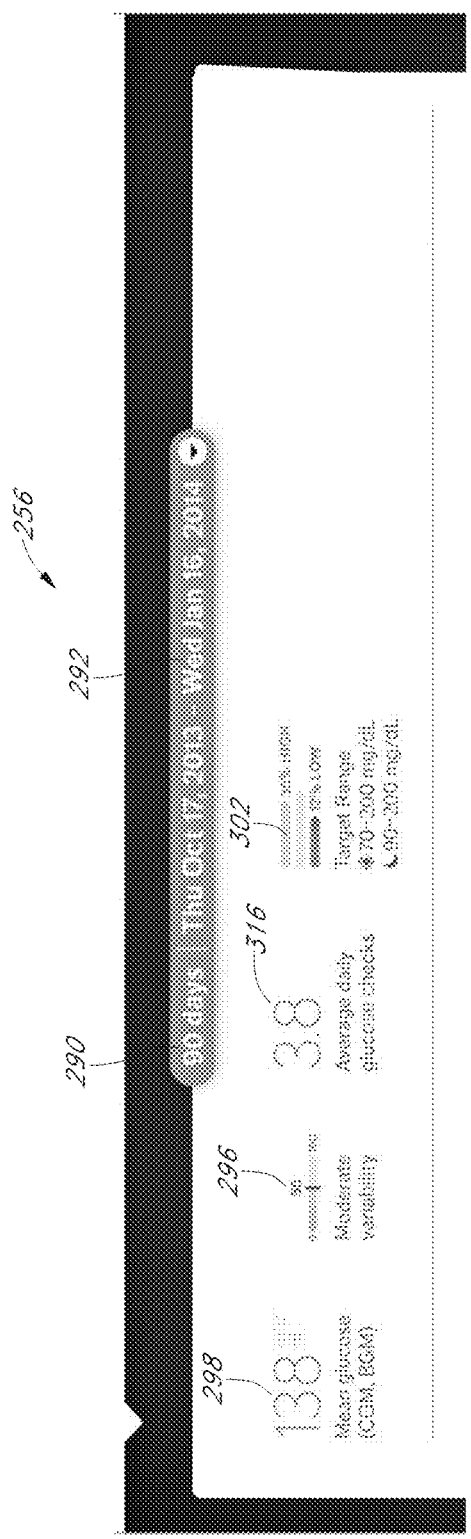
FIG. 8 is a more detailed exemplary user interface of a dynamic reporting system according to present principles, showing a BG summary.

FIG. 8 shows a similar summary section 256, but in the case where CGM data is not available. In this case, e.g., the report dynamically adjusts to include SMBG data, or data derivable from such SMBG data, so that the user can continue to receive some indication of their glucose concentration value. Many of the elements are the same as in FIG. 7, and their description is not repeated here. However, it is noted this summary section 256 includes an element 316 pertaining to an average number of daily glucose checks in the time period, which in this case differs from the CGM summary section due to the discretization and noncontinuous nature of the SMBG data. Moreover, the number of glucose checks per day becomes clinically of significantly heightened importance when CGM data is not available. Thus, the visualization of FIG. 8 dynamically changes relative to that of FIG. 7 due to the heightened importance of this number to the reviewer of the report.

Figure 9:
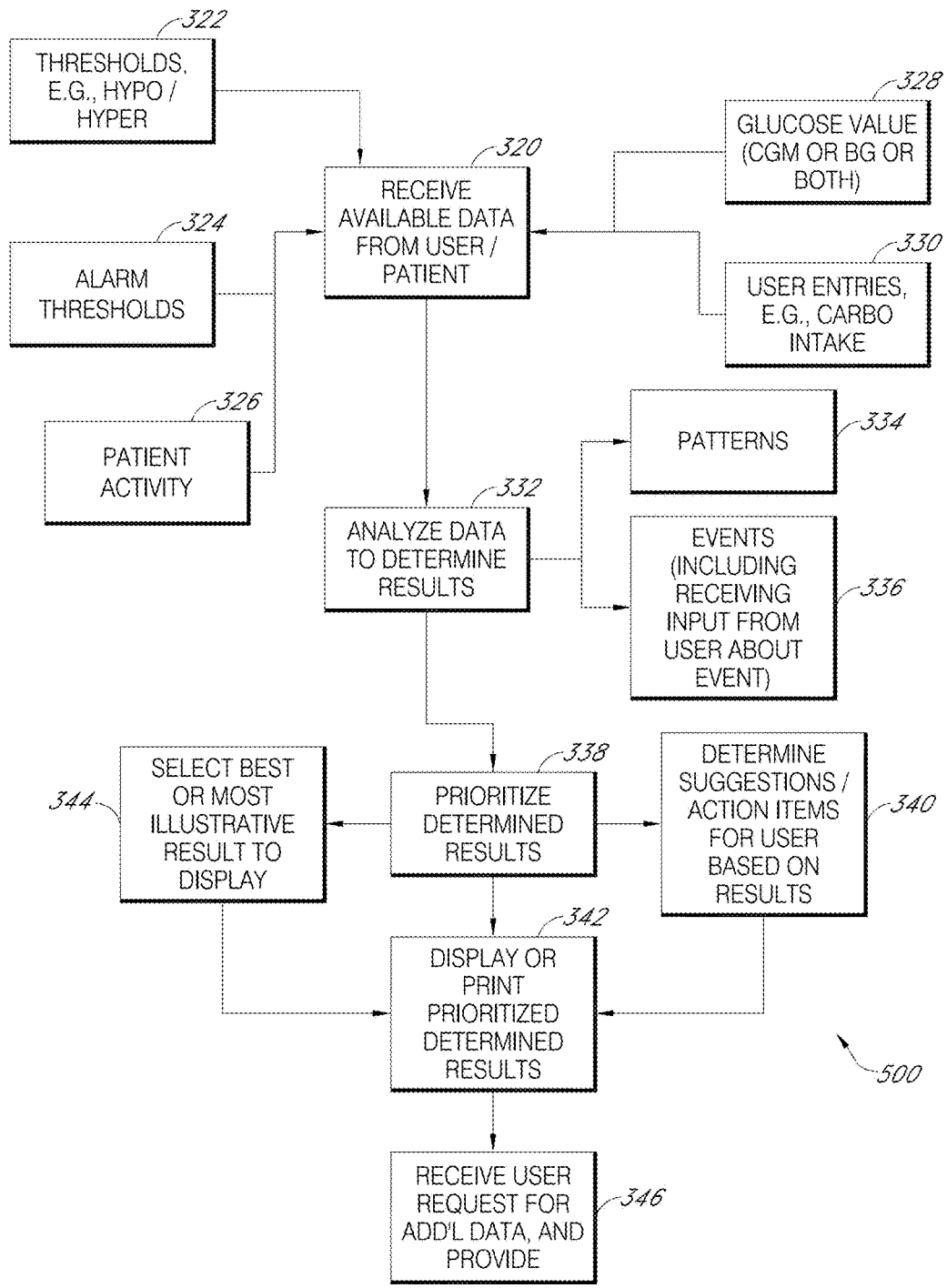
FIG. 9 is a flowchart of a second exemplary method of a dynamic reporting system according to present principles.

FIG. 9 is a flowchart 500 illustrating an exemplary method according to present principles. In a first step, data is received from one or more sources pertaining to the patient (step 320). This received data might include receiving thresholds for what is determined to be hypoglycemia or hyperglycemia for a given patient (step 322) and/or receiving data for alert or alarm thresholds or about (step 324). These types of data may be received from settings within the reporting system, including, e.g., one or more default settings for respective parameters such as thresholds, form data, a questionnaire provided to the patient, caregiver, or HCP, or the like. The receiving available data 320 may further include receiving data about patient activity (step 326), e.g., from an accelerometer or GPS. Certain types of patient activity data may be gleaned from other sources as well, including time of day, e.g., indicating waking activity versus sleeping. The receiving data may further include receiving a glucose value from a sensor (step 328), e.g., CGM data, SMBG data, or the like. Such receiving data may further include calculating or deriving data from the received data, e.g., slopes, accelerations, or the like. Such derived data can then be employed in certain fields and visualizations. A user may further enter information, e.g., about exercise or about meals, e.g., data about carbohydrate intake (step 330).

The data is then analyzed to determine results (step 332). The results may include the detection of patterns (step 334), as well as a determination of events, some or many of which may pertain to the patterns detected (step 336). Such events may be detected and identified as being common to and/or preceding the repeating data arrangements constituting the detected patterns, e.g., having appeared in two or more data arrangements, half the data arrangements, 75% of the data arrangements, or the like. In this sense the term "common" is used to refer to appearing in more than one data arrangement constituting a pattern, and not necessarily common to the user in general. The prevalence of the event may be measured with reference to a predetermined ratio or percentage, such as appearing in at least 25% of the data arrangements constituting the pattern, 50%, 75%, 90%, 95%, or 99%, and so on.

An icon may be displayed on the data visualization, at the time corresponding to the event, to indicate the occurrence of the event. A user-editable field may further be provided such that a user can enter information about the event, if known, so as to better inform the treating healthcare provider. Other data about the event may also be indicated on the data visualization, e.g., the nature of the event, an average amount of time between the event and the start of the pattern, an effect of the event, or combinations of these. In the case where the data corresponds to a glucose concentration value, the identifying the event may include identifying increases or decreases in glucose value preceding two or more of the repeating data arrangements constituting the pattern.

Data may be analyzed to obtain other results, including comparison results as described below, such as to compare the effects of an attempted disease management modification.

The determined results may then be prioritized according to a prioritization or ranking scheme (step 338). The dynamic reporting system, having generated the report based on the available data, may then display or print the prioritized determined results (step 342), or may select a best or most illustrative result for display (step 344) or printing. In another implementation, either instead of or in combination with the above steps, the reporting system may determine suggestions or action items for the user based on the results (step 340), followed by displaying or printing the same. In some cases, a user may desire additional information, e.g., the above noted "drilling down", and so upon user request, the system may provide additional information (step 346). For example, upon selection of a textual description of the pattern, the system may provide a series of daily charts showing the trace data upon which the pattern was determined.

Figure 10:
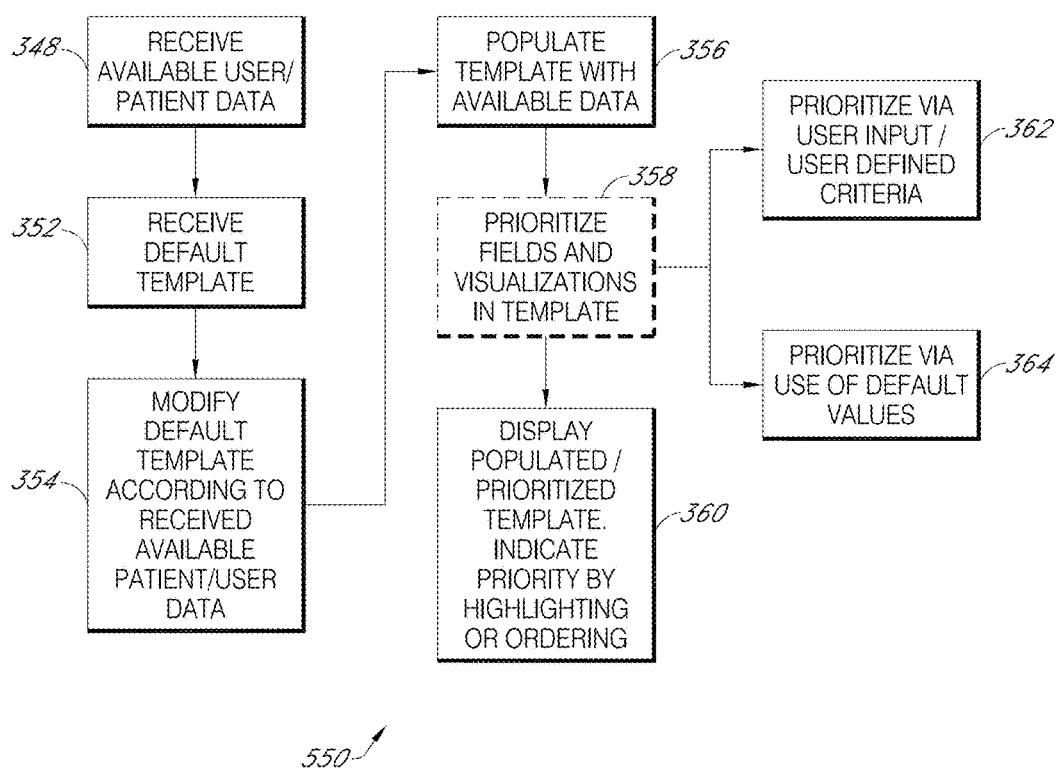
FIG. 10 is a flowchart of a third exemplary method of a dynamic reporting system according to present principles.

FIG. 10 is a more detailed flowchart 550 of a method according to present principles, which, in particular, displays the left side of the flowchart of FIG. 2C. A first step is to receive available patient data (step 348). This step may be performed in the same way as step 320 of FIG. 9. A default template is then received (step 352). The default template indicates various data fields and data visualizations which may be populated and displayed to a user, caregiver, or HCP. The default template is then modified according to the received available data (step 354). For example, data fields or visualizations may be removed or added according to what data is available, as may time periods covering such data.

The template may then be populated with available data (step 356). This step may include constructing the data visualizations, e.g., pattern charts, based on such data, as well as calculating data derivable from the received data for use in such data fields and visualizations (this step may also be performed prior to the populating step).

Besides modifying the default template, an optional step may be performed of prioritizing the data fields and visualizations in the template prior to display or printing (step 358). In this way, data of most interest to the user can be placed in a more prominent position, increasing the chance a user will pay attention to such data. This step may also include removing displayed data fields and data visualizations that have priority below a threshold. For example, depending on the level of detail desired by a user and set by the user in a settings field, a user may not desire to see patterns or pattern data which are deemed of low importance. The prioritizing may be accomplished by user input, by the use of user-defined criteria (step 362), or by the use of default values set by the system (step 364).

The populated and prioritized template is then displayed or printed (step 360). In some cases, the priority of a particular data field or visualization may be indicated by highlighting as well as by an order of presentation.

Figure 11:
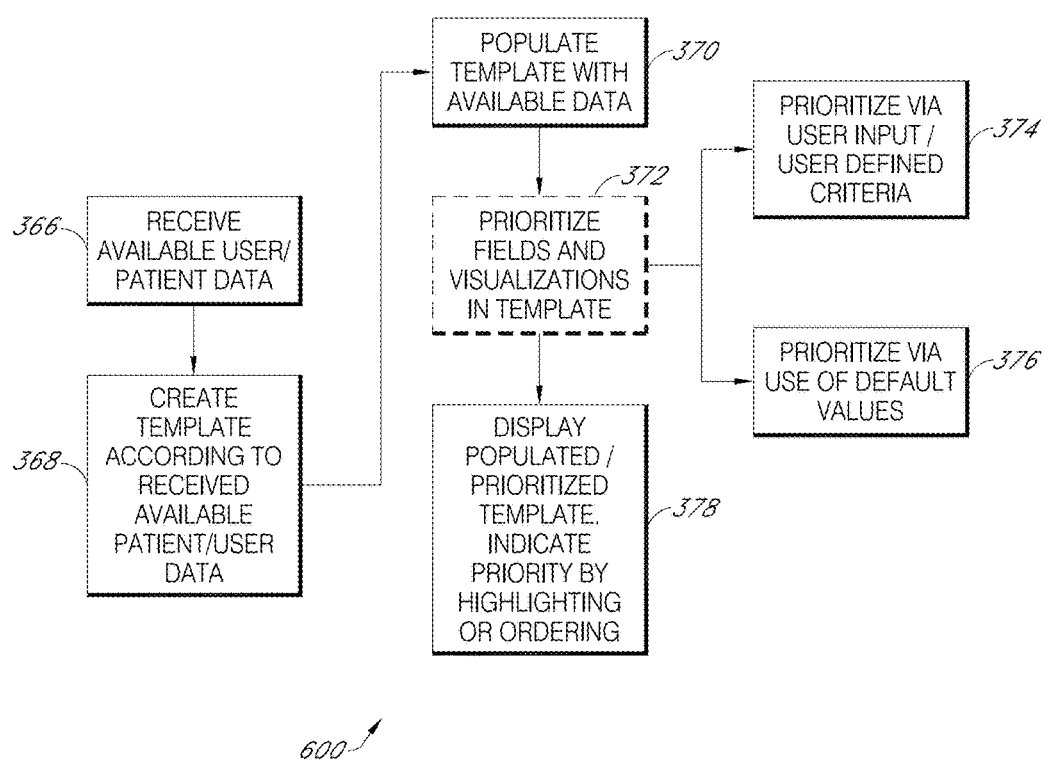
FIG. 11 is a flowchart of a fourth exemplary method of a dynamic reporting system according to present principles.

In yet another way, a dynamically generated report may be created by a method shown, in one implementation, by a flowchart 600 of FIG. 11. This method generally corresponds to the right side of FIG. 2C, and has a similar first step as that of FIG. 10, namely the receiving of available user/patient data (step 366). In this case, however, a template is then created according to the received available data (step 368), and not necessarily by use of a default template. The template is then populated with the available data (step 370).

And in this case, generally, the data fields and data visualizations will not require a "pruning" step as the same have been determined for usage by the availability of the data itself. As with FIG. 10, the fields and visualizations may be prioritized or ranked (step 372), using user input (step 374) or default values (step 376). The populated and/or prioritized template may then be displayed or printed (step 378).

Figure 12:
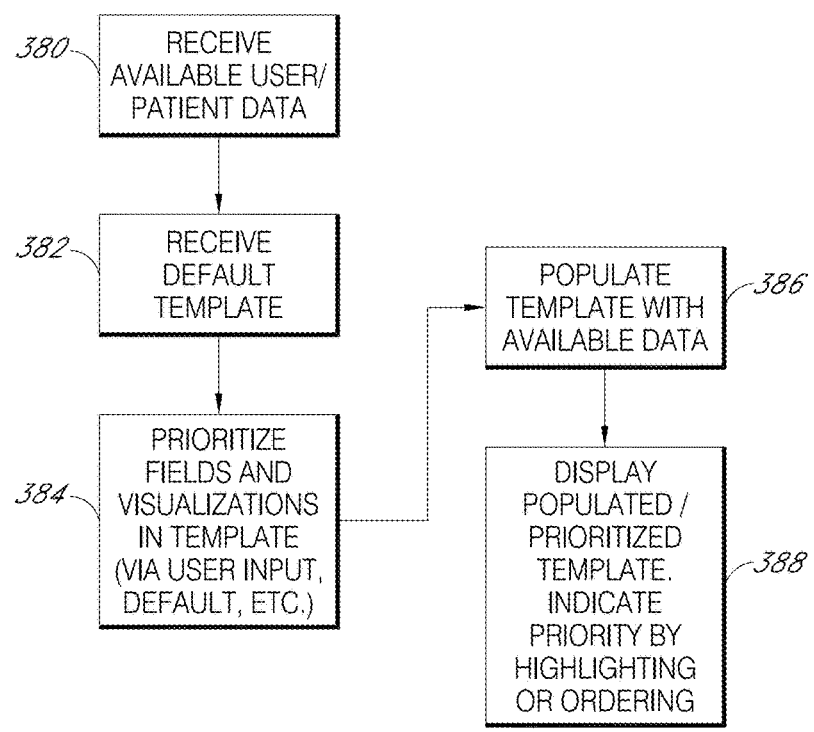
FIG. 12 is a flowchart of a fifth exemplary method of a dynamic reporting system according to present principles.

FIG. 12 is a flowchart 650 according to another exemplary method, in which data fields and visualizations are not necessarily removed, but prioritization is employed to focus the user's attention on particular aspects in the dynamically generated report. Certain steps are similar to those disclosed above. For example, patient data is received (step 380), as is a default template (step 382). According to user input, HCP input, or default settings, or the like, the report is dynamically generated by prioritizing the data fields and visualizations in the template (step 384) so as to put particular focus or emphasis on the fields and visualizations according to the prioritization scheme. The template is then populated with available data (step 386), and the populated template is then displayed or printed (step 388) as a dynamically generated report.

Figure 13:
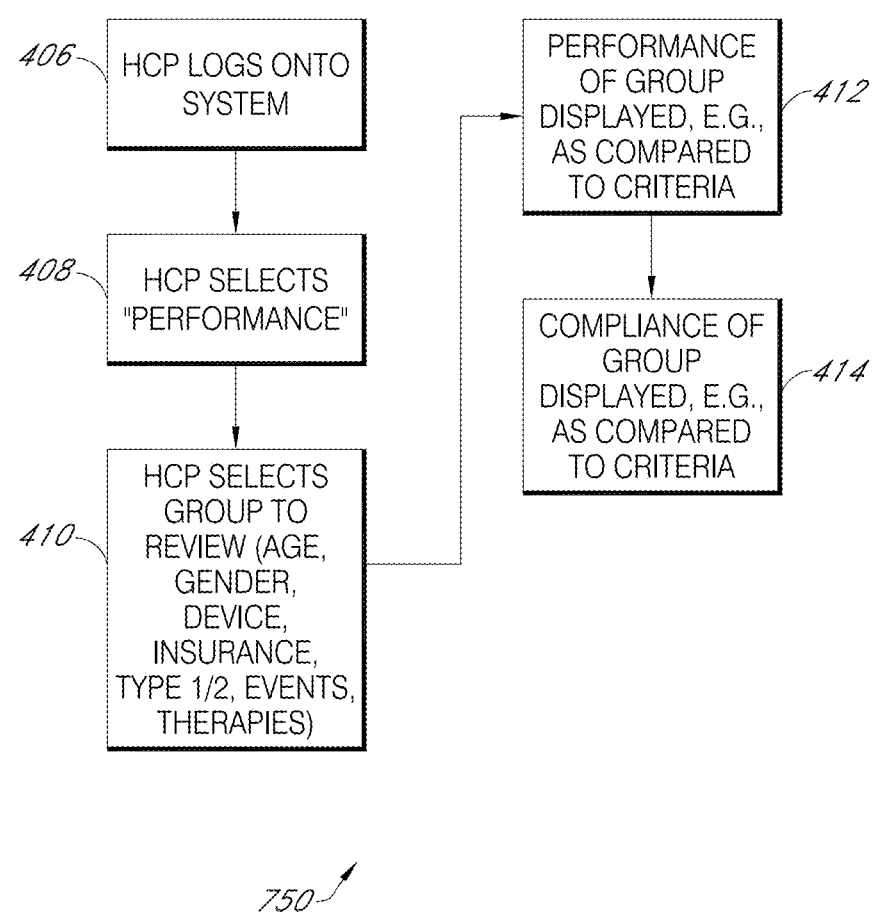
FIG. 13 is a flowchart of a sixth exemplary method of a dynamic reporting system according to present principles.

FIG. 13 is a flowchart 750 of a method which may be performed by an HCP, or in some cases by a caregiver, if the caregiver monitors multiple patients. The method 750 is primarily for use when multiple patients or users are being monitored. A first step is that the HCP logs onto the system (step 406). Upon selecting the performance option (step 408), the system may create and the HCP may view a dynamically generated report showing performance of all patients assigned to the HCP. The HCP may also filter the total list, so as to review a selected group (step 410). The filtering may be, e.g., on the basis of age, gender, device, insurance, type I versus type II, events, types of therapies, or the like. The performance of the filtered group may then be displayed (step 412). In some cases the performance of the group is displayed is compared to a criteria, e.g., a control group. A compliance of the group may also be displayed (step 414). For example, the overall compliance of the filtered group to their desired action items, e.g., the compliance of the group in managing their disease, e.g., by use of A1C values, or the like. Compliance of the patients in terms of meeting requirements laid out by the patients' insurances may also be displayed.

Examples of specific reporting features are now described.

In a pattern view, also termed a pattern block, pattern window, pattern section, or the like, one or more patterns may be displayed to the user as detected by the system. The patterns shown may be exemplary and indicative of patterns described above, e.g., patterns 258 within the view 350 of FIG. 6, and may be accessed by activating the patterns block 139 of FIG. 3. The system that detects the patterns (or otherwise analyzes data) may be the same as, or may be in data communication with, the reporting system. Referring to the pattern section 800 of FIG. 14, a number of patterns 416 are illustrated.

The patterns may be dynamically generated such that the most important patterns are placed first, and the patterns are situated in order of decreasing importance. Each pattern may be illustrated by graphical trace data, in particular illustrated by thumbnails, as well as textual data explaining the pattern. For example, the dynamic generation may result in a prioritization as described with respect to FIGS. 2C, 9, 10, 11 and 12, and resulting in patterns as shown in FIGS. 5 and 6.

The first pattern shown is pattern 417 indicating that the patient experienced a pattern of overnight lows. The pattern 417 is indicated in a thumbnail by illustrating three separate exemplary single day traces showing how the trace went below a threshold for a duration during the overnight time period.

Next shown as a pattern 419 illustrating that the patient experienced a pattern of lows after breakfast. The pattern 419 not only illustrates the low but also illustrates how thresholds may be configured to change depending on daytime versus nighttime or on other bases. In this case, as well as in the other patterns below, only a single trace is shown, but the same may be the trace most illustrative of the pattern, or may be a combination (e.g., an average) of traces illustrating the pattern, or the like. The intent is to indicate the pattern in a way so as to draw the user's attention to the same and provide a high-level visual explanation of the detected pattern. In the pattern 419, the trace descends below the lower threshold, and, as illustrated, the portion between the trace and the threshold may be filled in to indicate even more clearly to the user the drop.

The next pattern 421 indicates that the patient experienced a pattern of weekend highs. The pattern 421 also indicates the use of changing thresholds, as seen by the higher hypoglycemic threshold 402 versus the lower hypoglycemic threshold 404, and indicates the pattern by traversal of the trace above the desired threshold in a number of instances, again with the portion between the threshold and the trace filled in.

The next pattern 423 indicates that the patient experienced a pattern of highs after dinner. As with the above, filling in the portion between the threshold and the trace may help indicate the pattern to the user.

The last chart shown is again of a single trace 425, which indicates the patient's "best day". The pattern 425 may be chosen based on a number of factors, e.g., which day the user had the longest duration without an excursion outside of the lower or higher thresholds. In the case of the trace 425, the patient was within the desired range for approximately 19 hours. While the chart is shown as a single trace, patterns may also be determined from "best day" data. That is, where a patient follows a particular routine, it may be expected that the "best day" will also follow a pattern.

It will be understood that other types of patterns may also be displayed and/or printed, besides those noted above. For example, patterns may be identified or detected based on when highs or lows occur, e.g., nighttime, morning, after certain events such as meals or exercise, or the like. Patterns may also be identified or detected based on the day of the week in which they occur, as many users have different routines based on weekdays versus weekends. Patterns may further be identified or detected based on their relationship to events. Such events include the administration of insulin, exercise, meals, or the like. Patterns may also be identified or detected based on combinations of one or more of the above factors. As noted it may be desirable to identify and dynamically report on patterns noted of good disease management. Such "good job" patterns may be employed to reinforce positive behavior, and further allows users to look back on such notifications of good disease management and try to repeat or emulate such behaviors. In the determination of such patterns, data may be analyzed for where patients are within their predetermined range for significant durations, as well as where patients reversed previously identified "bad" patterns.

FIG. 15 illustrates a dynamic report 850 in which a number of patterns 418 are illustrated based on SMBG data values alone. The patterns shown are similar to those in FIG. 14, but are generally based on less data due to the (noncontinuous) nature of SMBG data. The report 850 includes a pattern of overnight lows 427, a pattern of lows after breakfast 429, a pattern of weekend highs 431, and the report of a best day 433.

Figure 16:
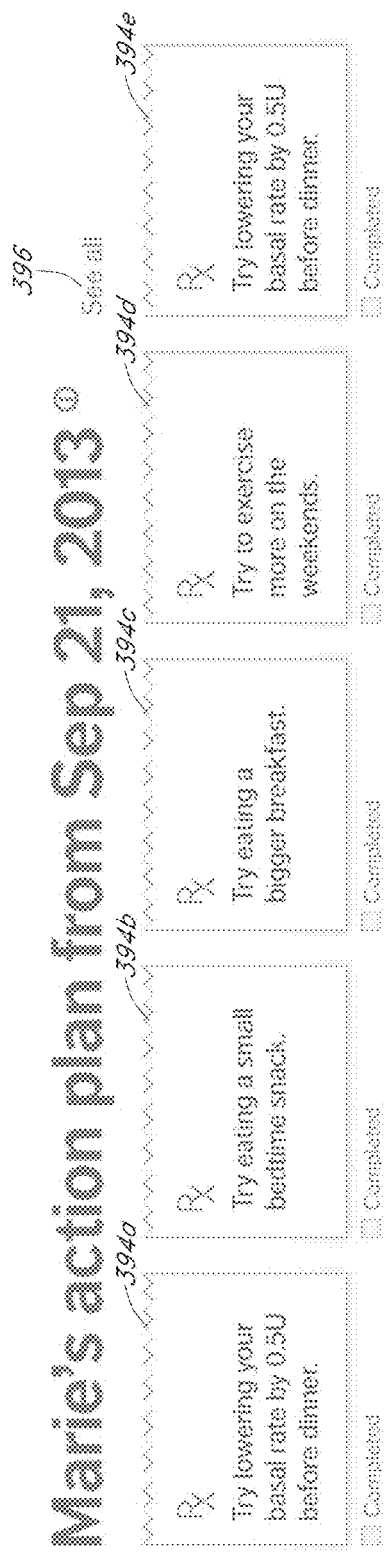
FIG. 16 is an exemplary user interface of a dynamic reporting system according to present principles, showing a set of proposed actions determined from received monitoring data.

FIG. 16 shows an illustrative action plan window 264. A number of specific suggested actions 394a-394e are illustrated, these based on the data received, including patterns detected and other information, and results gleaned from data analysis. Checkboxes may be provided under the action items to allow the user to indicate compliance with the action item, as well as to convey to the user a feeling of accomplishment in finishing the task. A "SEE ALL" button 396 may also be provided, which may lead to a window 950 shown in FIG. 17 indicating a list 422 of action items previously suggested. The list 422 can include a date of suggestion of the action item, a textual indication of the action item, as well as an indication of completion.

Figure 18:
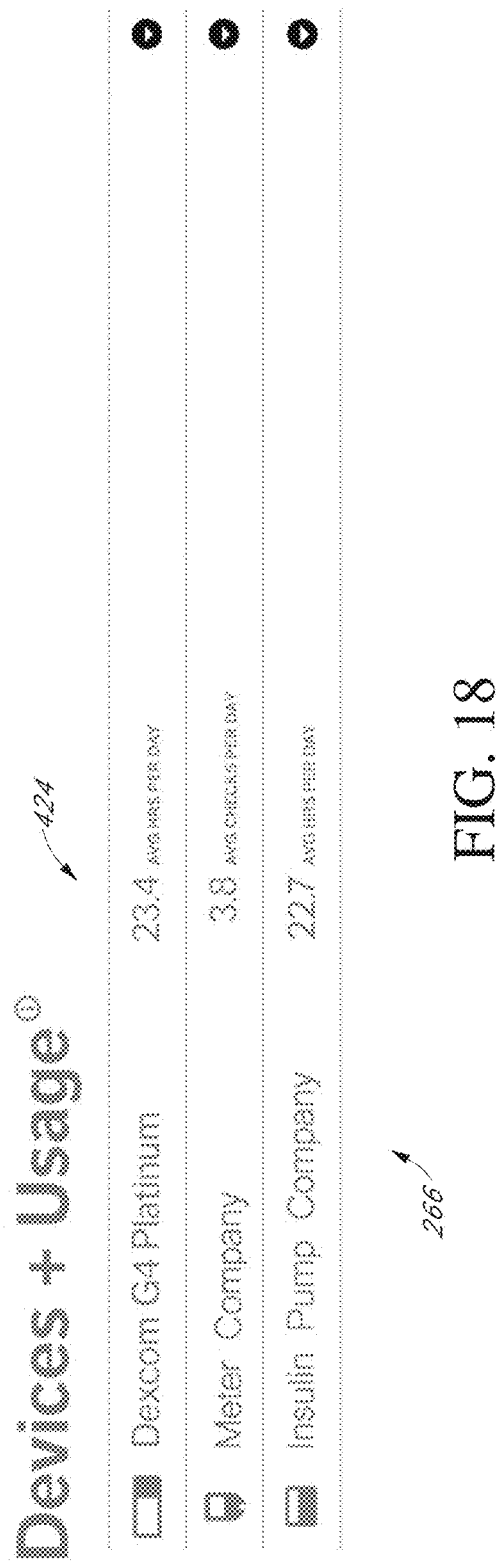
FIG. 18 is an exemplary user interface of a dynamic reporting system according to present principles, showing a displayed set of devices associated with the patient or user being monitored.

FIG. 18 illustrates a greater detail of the devices and usage window 266, which may form a portion of a dynamically generated report and which is a similar window as described above with respect to FIGS. 5 and 6. The window 266 includes a list of devices 424 associated with the user, which devices generally providing data which at least in part makes up the dynamic report. If the devices interface with the reporting system, then generally, any data exposed by the device's API may be used in the report. Such is often the case with pumps that may interface with a CGM. If the user enters data from another device, e.g., calibration data from an SMBG meter, then the data is limited to only that which the user enters, and data derivable therefrom. In the list of devices 424, entries are given for a CGM, an SMBG meter, and a pump. Also shown are amounts of usage of the devices, e.g., how many hours per day they provide service to the patient, or in the case of the SMBG meter, how many checks per day are made by the user. This portion of the report can also be dynamically generated because data or data visualizations can be removed, modified, highlighted, or the like, depending upon importance, or other criteria set by the system or a user.

FIG. 18 generally shows summary information for the devices and their usage.

Figure 19:
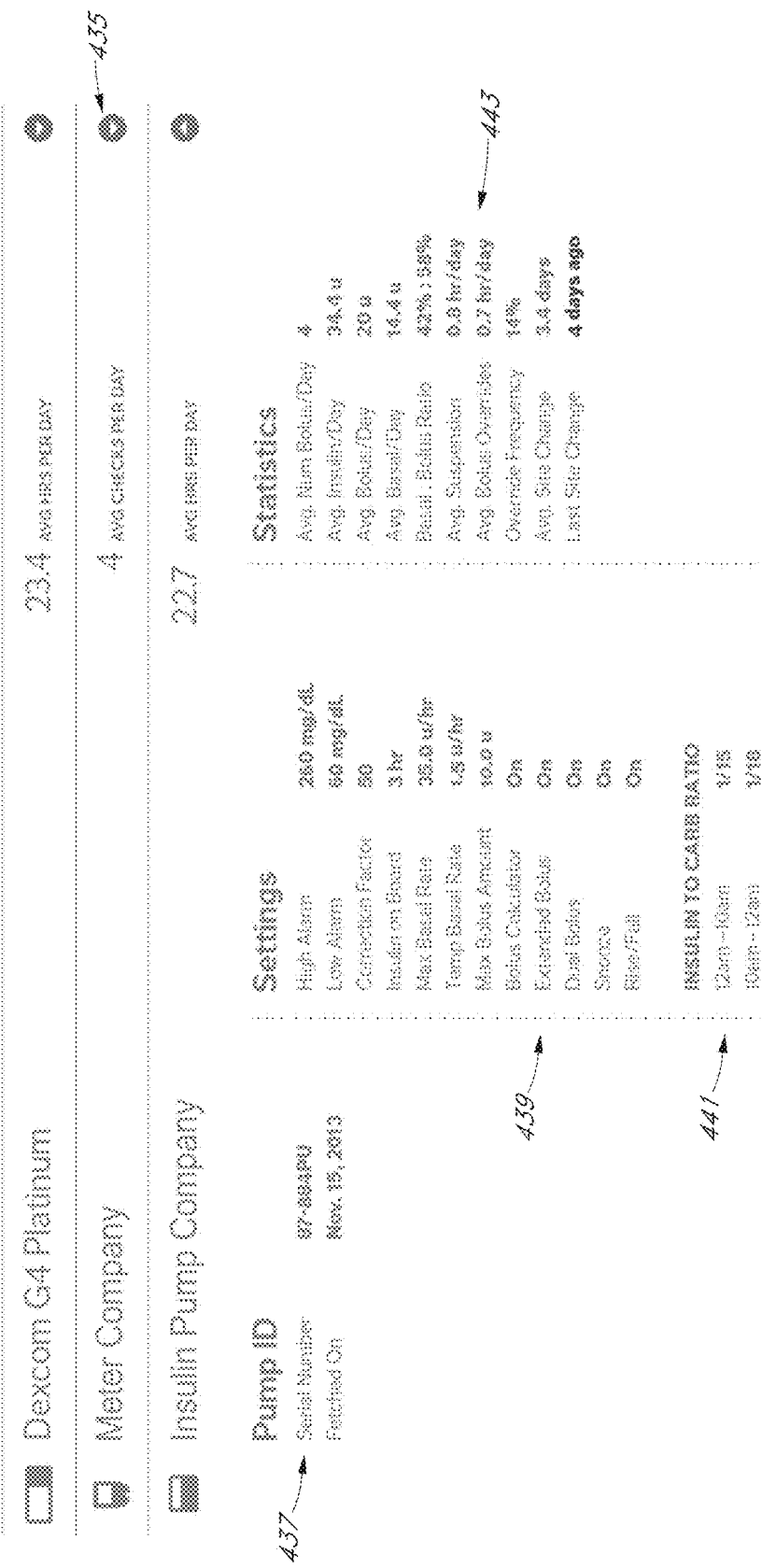
FIG. 19 is a more detailed exemplary user interface of a dynamic reporting system according to present principles, showing a displayed set of devices associated with the patient or user being monitored, with an expanded section providing additional detail about a pump being portrayed.

On the other hand, FIG. 19 shows additional information which may be displayed in a window 268 about one or more of the devices and their usage. In particular, selecting one of the devices can cause expansion of that device's section to a window 268 that provides a significant amount of additional data about the device, in FIG. 19 the pump, as may be available when the pump can interface with the reporting system. Such additional data may include pump identification information 437, pump settings 439, an insulin-to-carbohydrate ratio section 441, as well as statistical information 443. While the expanded window illustrates additional information for the pump, it will be understood that selecting or activating the summary information for other devices will cause a similar expansion to show additional information associated with the usage of that device.

In a dynamic reporting system according the present principles, the data which is not available may be omitted from the report, thereby clarifying the report and focusing the user's attention on fields and visualizations for which data is available. If data for a particular device is not available for the selected timeframe, no data for that device will be shown.

Figure 20:
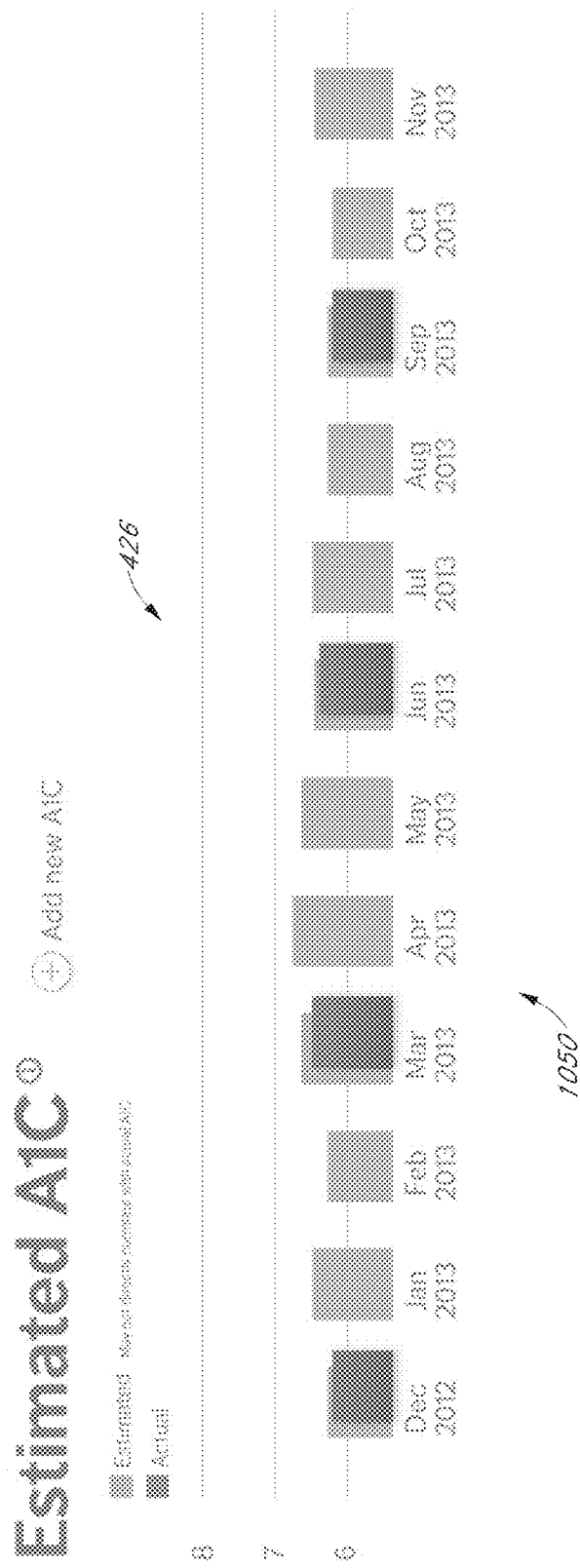
FIG. 20 is an exemplary user interface of a dynamic reporting system according to present principles, applied to the case of glucose monitoring, and showing a displayed set of A1C data.

FIG. 20 shows another window 1050 which may be portrayed in a dynamic reporting system. In particular, the window 1050 shows a series 426 of A1C data, organized by month, and in FIG. 20, spanning a date range from December 2012 to November 2013. Both estimated and actual A1C values (as determined by an A1C test) may be schematically shown, where the estimated values are shown monthly and the actual values are shown quarterly. As above, if data is not available, portrayal of that data in a dynamically created report may be omitted, simplifying presentation of the report. Similarly, if data analysis indicates certain data is of lesser validity, the same may again be omitted or flagged as less reliable. As may be seen, the window 1050 may have a button allowing entry of additional A1C data.

Figure 21:
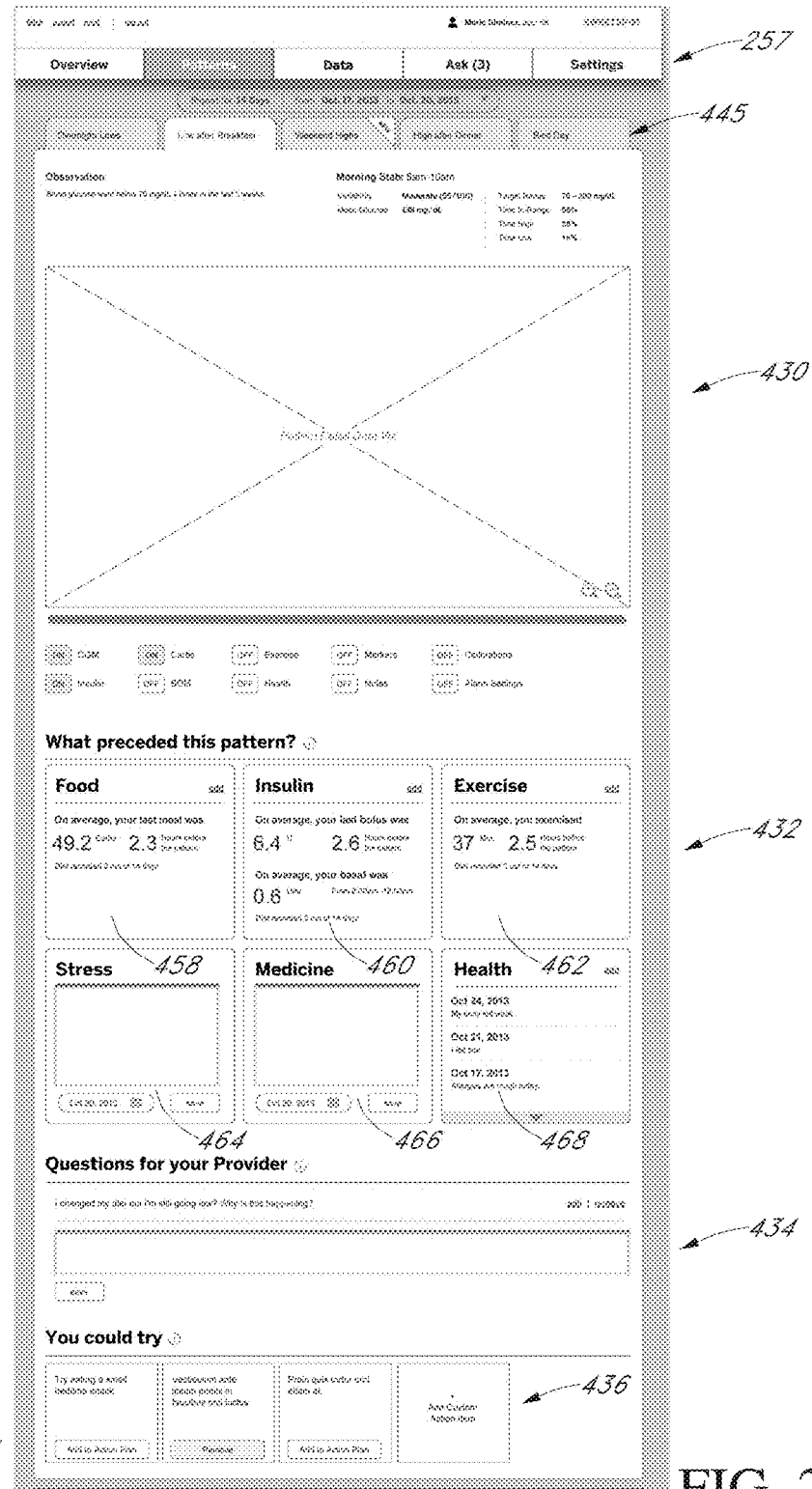
FIG. 21 is an exemplary user interface of a dynamic reporting system according to present principles, showing a view of displayed data, including a window for patterns, events preceding patterns, questions for a provider, and suggestions/tips.

FIG. 21 illustrates another view or window 1100 within the pattern tab of navigation bar 257. In particular, this figure provides a wireframe view illustrating exemplary features. Other features may be portrayed in variations. In FIG. 21, each pattern identified may be listed as a separate tab within pattern tab bar 445. The section may then list pertinent data about the particular pattern identified, including data fields and visualizations. The creation of such presented data may be done in a dynamic fashion, as noted above, taking account of what data is available, as well as prioritization or ranking schemes.

One or more exemplary graphical data visualizations of the pattern may be portrayed in a chart section 430 within the window 1100. Such data visualizations may be as noted above and below, as a multi-day view, as a multi-day view using variability bars, as a series of single day views, or the like. Exemplary visualizations which may be portrayed within the window 1100 include those shown in FIGS. 22, 23, 24, 25, and 27B.

Data available about events that preceded the pattern may be listed in a section 432. This information may include sections such as a food intake section 458, an insulin on board section 460, an exercises section 462, a stress section 464, a medicines taken section 466, a health data section 468, or the like. In some cases, the presented data will be modified to only include available data. In another implementation, the sections 458, 460, 462, 464, 466, and 468 and the like may include editable text boxes allowing a user to enter comments and data about events preceding the pattern. The presented data in section 432 may be prioritized according to that which is most likely to have had an effect on the pattern, e.g., post-meal highs may be particularly caused by prior food intake, and so on. Thus, the especially pertinent data may be dynamically placed first, highlighted, or otherwise called out.

As noted before, a questions section 434 may be provided for a user to pose questions to their HCP about the detected pattern. And a suggestion section 436 may be provided to indicate potential steps the user may attempt to ameliorate or minimize the occurrence of the pattern in the future (or steps to repeat if the pattern is a good one). In some cases, if the user selects a suggestion in the suggestion section 436, the same may be added to the action plan, such as seen on the overview window.

Figure 22:
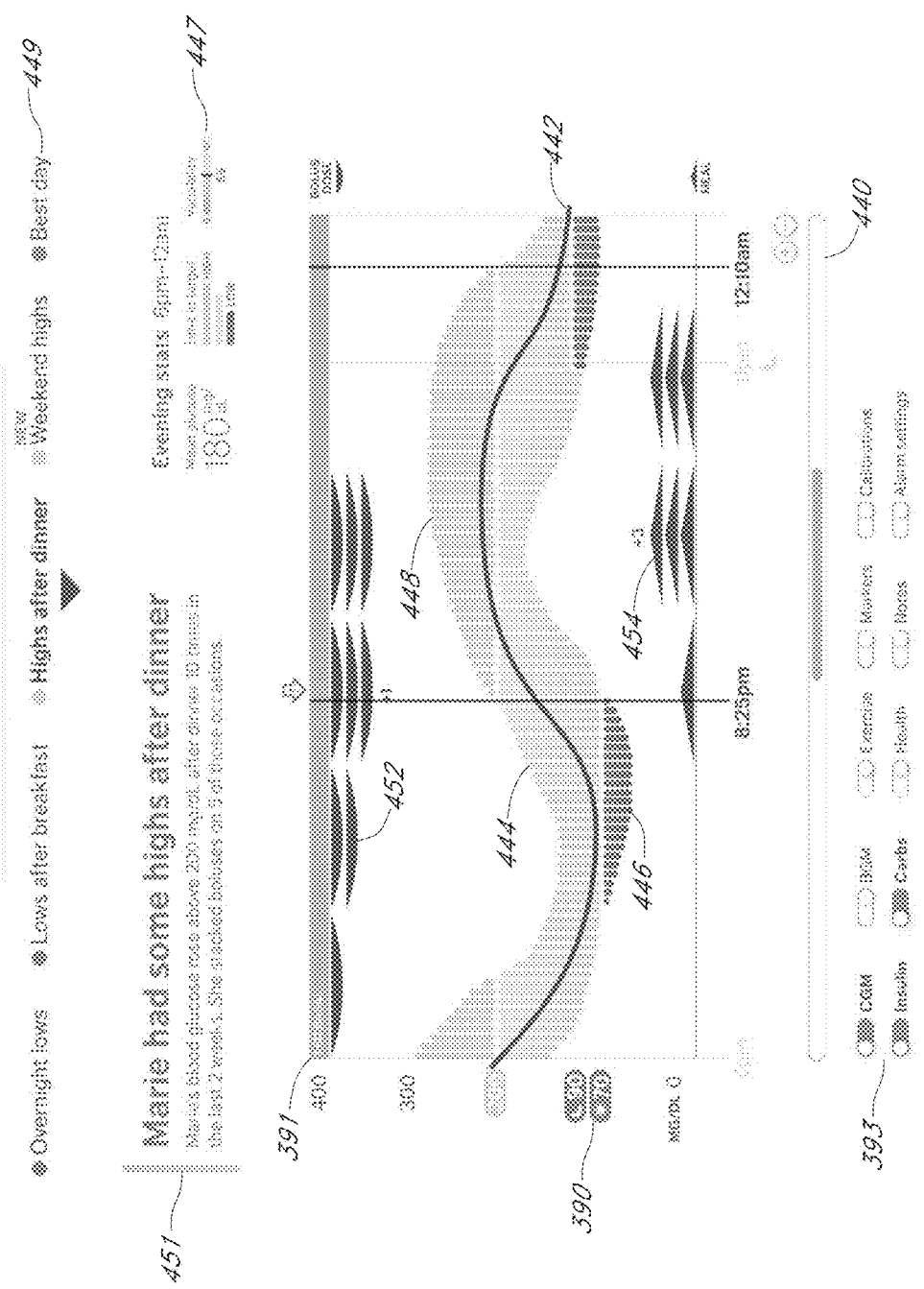
FIG. 22 is a more detailed pattern graph employable with a dynamic reporting system, showing variability bars, as well as indications for insulin/carbohydrate ingestion.

FIG. 22 shows a more advanced pattern chart 1150 which can form a portion of a dynamic report. The pattern chart 1150 can include a textual description 451 of the pattern, telling the user in plain language about the detected pattern. A statistics section 447 may be provided to indicate values such as the relevant time period, the mean glucose value, level of variability, and time within range compared to time outside of range. It will be understood that other statistics may also be provided in this section. Moreover, one or more of the values can be omitted, in a dynamically created report, if data is not available or is deemed less important (e.g., having a priority less than a threshold).

The chart may include a mean value trace 442 indicating the average value of glucose over the noted time period, as a function of time, with the timeframe dynamically selected to illustrate the detected pattern. The timeframe may also be selected to illustrate the pattern, as well as a time before and after the pattern, to assist in determining a cause of the pattern or to determine, e.g., how a patient rebounds from the pattern. For example, for lows experienced during nighttime, a time frame may be selected including some time preceding the night timeframe. In this example, the time frame chosen may be selected to include dinner so as to include the effect of meal ingestion on the nighttime low. In one particular example, for a common event of a rebound high, a time frame may be selected so as to visualize the low, the rebound high, as well as subsequent user efforts to address the same.

An indicator 390 may be disposed on the chart showing varying or dual low threshold values, e.g., a daytime value and a nighttime value. Varying or multiple thresholds may be set for other reasons as well. For example, there could be multiple thresholds for low glucose concentration conditions and multiple thresholds for high glucose concentration conditions. Thresholds could be set (and varied) for regular meal times and/or regular exercise times. One or more thresholds could also be set to dynamically and automatically adjust for given conditions. For example, one or more set thresholds could be triggered by certain events, i.e., upon the occurrence of an event, the threshold is controlled to that value. For example, upon the occurrence of a pattern being recognized for regular meal times or exercise, systems and methods according to present principles may prompt the user to set or edit a threshold within the settings block or devices block, and in some cases may even suggest thresholds to set. Moreover, the threshold need not be a straight horizontal line. Rather, the same may take the form of the curve and may reflect the biological processing of insulin or carbohydrates within a host, e.g., the user, particularly if personalized data such as insulin sensitivity are known to and modeled by the system and method. Again, the thresholds may be for alerting purposes, alarming purposes, determining potential delivery of a bolus, and so on.

The thresholds may be set by the user in the settings block 147, as well as in other ways. For example, the devices block 149 may have editable threshold fields associated with each listed device, and in other cases users may set thresholds using other blocks including patterns block 139. Thresholds may also be set by being received from other devices including SMBG meters and pumps. The indicator 390 may reflect one or all of these different thresholds. A slider bar 440 may be included to allow the user to view adjacent time periods, and zoom buttons may also be employed to expand or reduce the displayed timeframe.

While the mean value is indicated by trace 442, the overall pattern is indicated by the use of variability bars, indicating graphically how values varied above and below the mean. It should be noted that indicating variability may be performed in a number of other ways as well, including the use of an envelope surrounding the mean value, where the envelope represents a standard deviation, and so on. A portion 444 indicates the duration of time when the patient was within the target range, a portion 446 indicates the duration of time when the user was below the target range, and a portion 448 indicates the duration of time when the user was above the target range. As the pattern relates to highs after dinner, a particular timeframe has been set apart by vertical bars, e.g., 8:25 PM to 12:10 AM, over which (on average) the high occurred.

The variability bars may change in color for portions of the bar that fall within areas of the charts delimited by the thresholds (e.g., areas above, between and below high and low thresholds), and the same is true for signal traces in general, such as in FIGS. 14, 15, 23-25, 27B, 35-37, and 39-47. Where the signal traces are displayed as discrete elements, the format of the elements may change above, between and below given thresholds.

The chart 1150 may also include other information. In one implementation, the chart 1150 includes information about medicament administration. In the case of diabetes management, the medicament administration may include information about administration of insulin, e.g., pump usage, as shown by a horizontal bar having a height indicating a basal rate 391 (which generally is constant, at least over shorter periods of time) as well as an indicator of boluses applied 452. Each bolus is indicated by an icon, and the number of icons can indicate the number of boluses. By placing the icons indicating boluses at this location within the pattern chart 1150, i.e., above the graph, the boluses appear to "push down" on the glucose value, thus intuitively indicating to the user the effect of the insulin delivery. In the same way, carbohydrate intake may be indicated by icons 454, and their placement below the chart may be so as to appear to "push up" on the glucose value, again, intuitively indicating to the user the effect of carbohydrate ingestion. As shown, a numerical indication may be provided to indicate the number of boluses or units of carbohydrates. In other implementations, described below in the context of FIGS. 42 and 46, the icon can have a particular shape, indicating a "tail", giving greater detail on the effect over time of insulin or meals on a patient's glucose value. In particular, the tail reflects as a function of time (and with an amplitude axis pointing downward, such that the "drip" shape of the tail represents positive values) the amount of active insulin in the user, also termed "insulin on board", The amount of insulin on board may be determined algorithmically, and such algorithms may be in some cases "personalized" to the patient, where after time and history a given patient's insulin sensitivity is used to uniquely determine, or predict, the insulin on board and even the shape of the tail.

A navigation bar 449 can be placed adjacent the pattern chart so as to enable convenient navigation by the user to other patterns. A series of toggles or other indications 393 may be displayed and employed to indicate to the user the types of data displayed on the chart.

Figure 23:
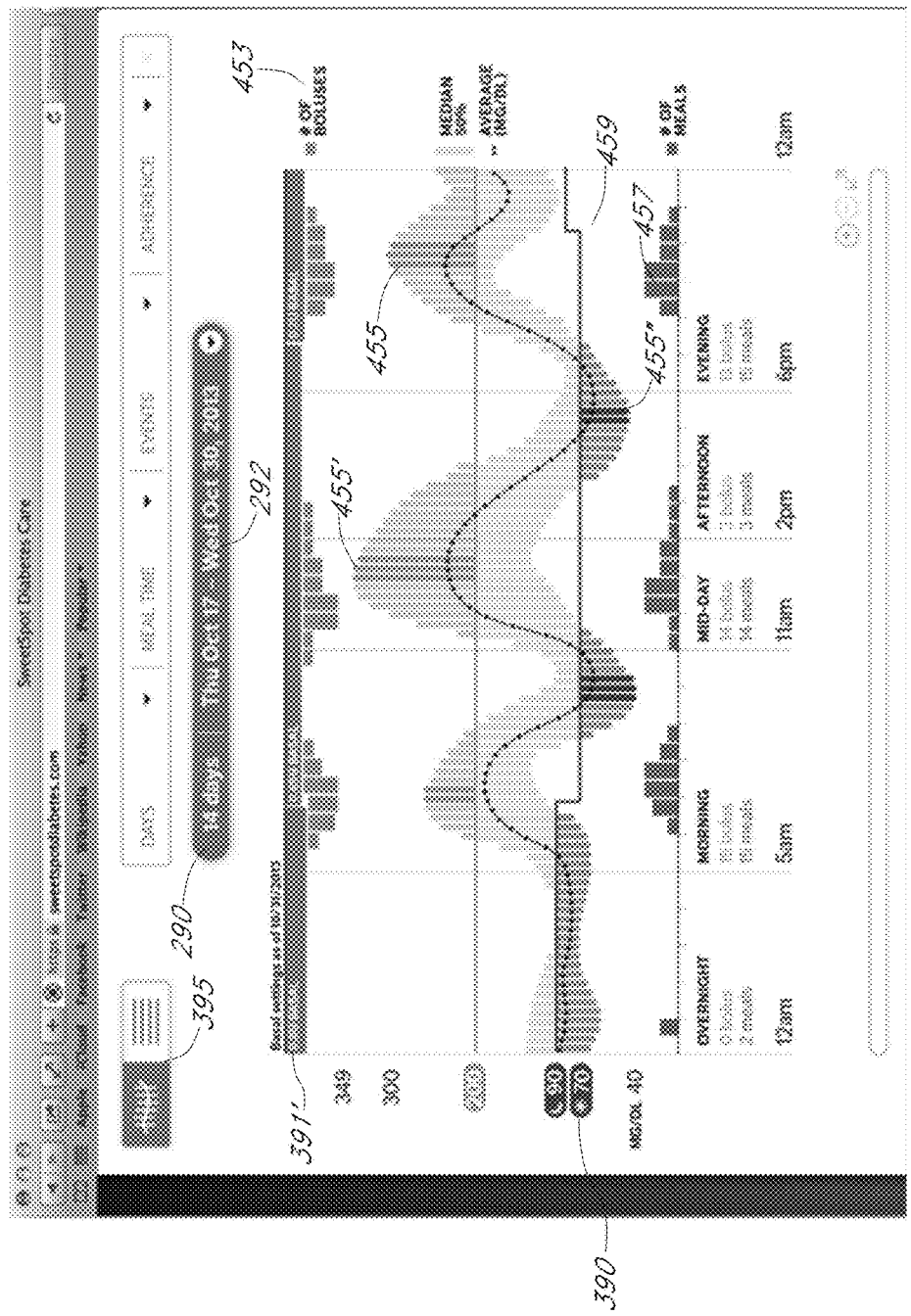
FIG. 23 is another more detailed pattern graph employable with a dynamic reporting system, showing variability bars, as well as indications for insulin/carbohydrate ingestion.

FIG. 23 illustrates another form of chart 1175, and in particular a "day view" chart, developed using data from the time shown in field 292 (a two-week time period). This chart provides various information about patterns, as will be described below in the context of the bolded variability bars.

The chart 1175 may be displayed upon, e.g., a user selection of a particular pattern within a list of pattern/pattern thumbnails, such as shown by patterns 416 of FIG. 14 or patterns 418 of FIG. 15. Selection from the thumbnail or descriptive text may lead to a depiction like FIG. 23, in which greater and additional detail about a pattern is provided. Such may be displayed on its own or in conjunction with the display of other patterns. In one implementation, the chart 1175 occupies the place of the wireframe place holder 430 in the view 1100. The pattern 416 may be derived from a number of parameters, including the stored glucose concentration data, the selected time periods, data about devices and usage, and in some cases other data as may be available and which is relevant to the selected time periods, such as user entered data, e.g., about illnesses or subjective indications of how they feel, and other like data.

This chart includes certain elements as noted previously, and their description is not repeated. The pattern chart 1175 also includes buttons 395, which may toggle the display of the chart from indicating a multi-day pattern using variability bars versus indicating a multi-day pattern using a series of displayed single day charts. The user may choose which style of chart, or the same may be automatically chosen by the system depending on how best to illustrate the pattern. As with FIG. 22, FIG. 23 employs variability bars. In addition to coloring, indicated by crosshatching, specific horizontal lines are drawn showing the target range with upper and lower thresholds (the lower threshold 459 varying according to daytime versus nighttime).

In FIG. 23, bolus information is indicated by a histogram 453, rather than the quantized bolus units shown in FIG. 22. The same is true of carbohydrate intake information 457. FIG. 23 also shows a varying basal rate 391'. The basal rate 391' may vary based on a number of factors, a key one being that a user may have varied the rate in order to address a particular event, e.g., a hyperglycemic event. The basal rate 391' may also vary based on other factors. As one example, a user may program the same to vary based on the time of day. Other reasons or causes for varied rates will also be understood.

Variations are seen not only in the bar height, but also by numerical indicators. Variability bars are shown which may represent a range of values encountered over a common time period, a standard deviation, or other statistical measure of variance of the measured glucose concentration value. Certain of the variability bars, and in particular the bars 455, may be displayed which are bolded to indicate that a pattern has been detected. For example, in FIG. 23, the bolded bars 455' in the midday range may indicate a lunchtime high, while the bolded bars 455" just prior to the evening range may represent an afternoon low. Other patterns will also be understood.

Figure 24:
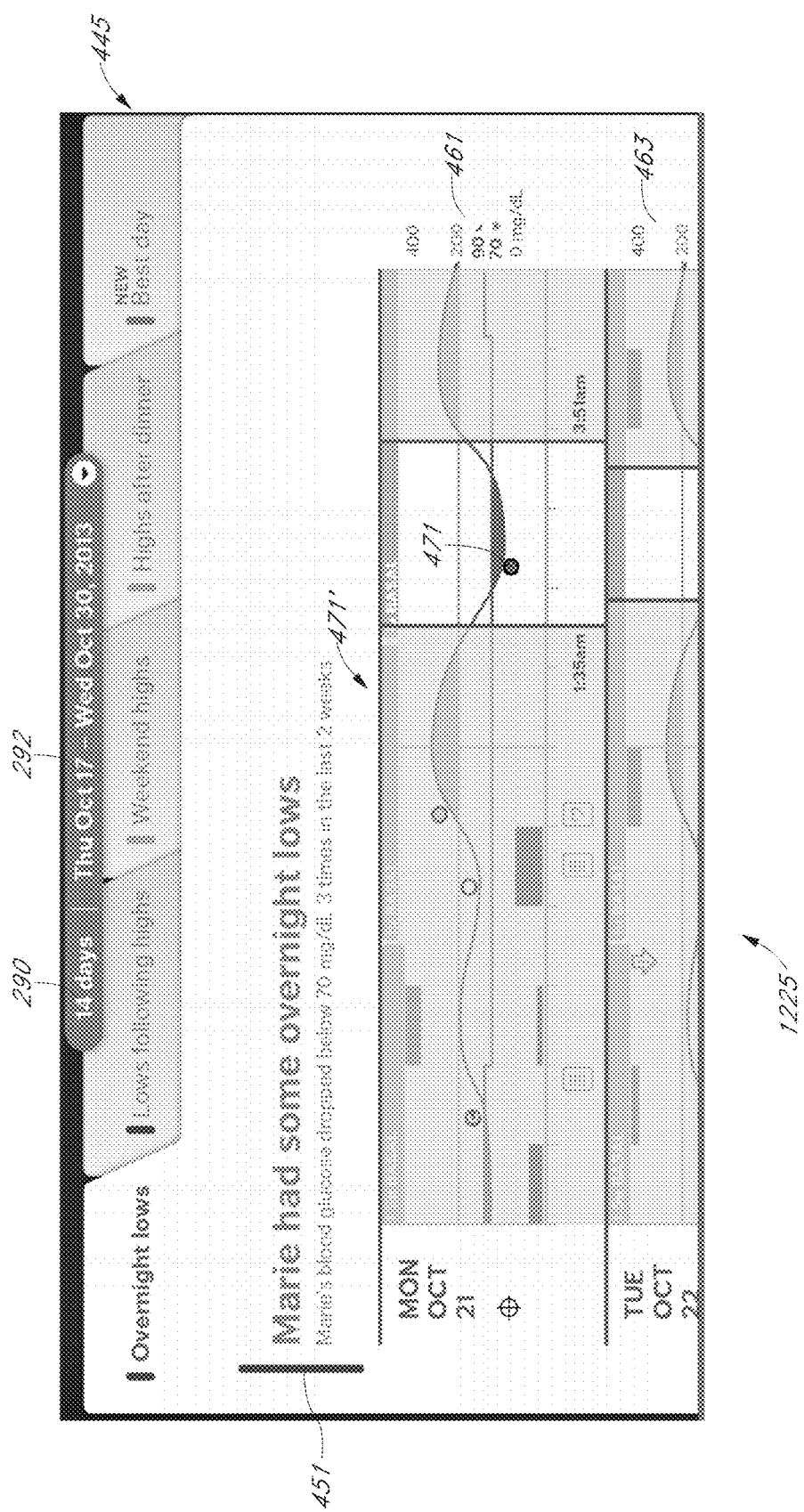
FIG. 24 is another more detailed graph employable with a dynamic reporting system, showing a trace for a single day, and illustrating events associated with a pattern.

FIG. 24 illustrates a pattern chart 1225 in yet another form, in which a series of single day traces 461 and 463 are portrayed one above the other. While the traces are separated by different days, each trace need not represent an entire day, but rather a selected timeframe in order to better illustrate the pattern. Certain days are illustrated, generally those determined to best illustrate the pattern over the analyzed timeframe. However, other ways of choosing the illustrated days are also possible, including choosing days that illustrate a diversity of ways in which a pattern may manifest itself. For example, post-meal highs may be illustrated by a pattern occurring after dinners, a pattern occurring after lunches, and so on.

In more detail, while various aspects are shown in the diagram relating to other glucose excursions, a portion in which the noted pattern is seen, i.e., overnight lows, is dynamically highlighted in the trace 461 as well as in the trace 463. For example, in the single day traces 461, the same is seen by a dot 471 (indicative of a single point SMBG measurement) near the beginning of the low period as well as in a graying out of the non-low portion 471' of the trace 461. Similar highlighting may be provided in traces for other patterns noted in pattern bar 445, e.g., in highs after dinner, or the like. In such a way, a user can compare the different detected patterns, as well as events which preceded each pattern. Such analysis is believed to provide valuable insight into diabetes management, and in particular to guide patients, through the use of historical pattern data, to learn how to better manage their diabetes in the future.

Figure 25:
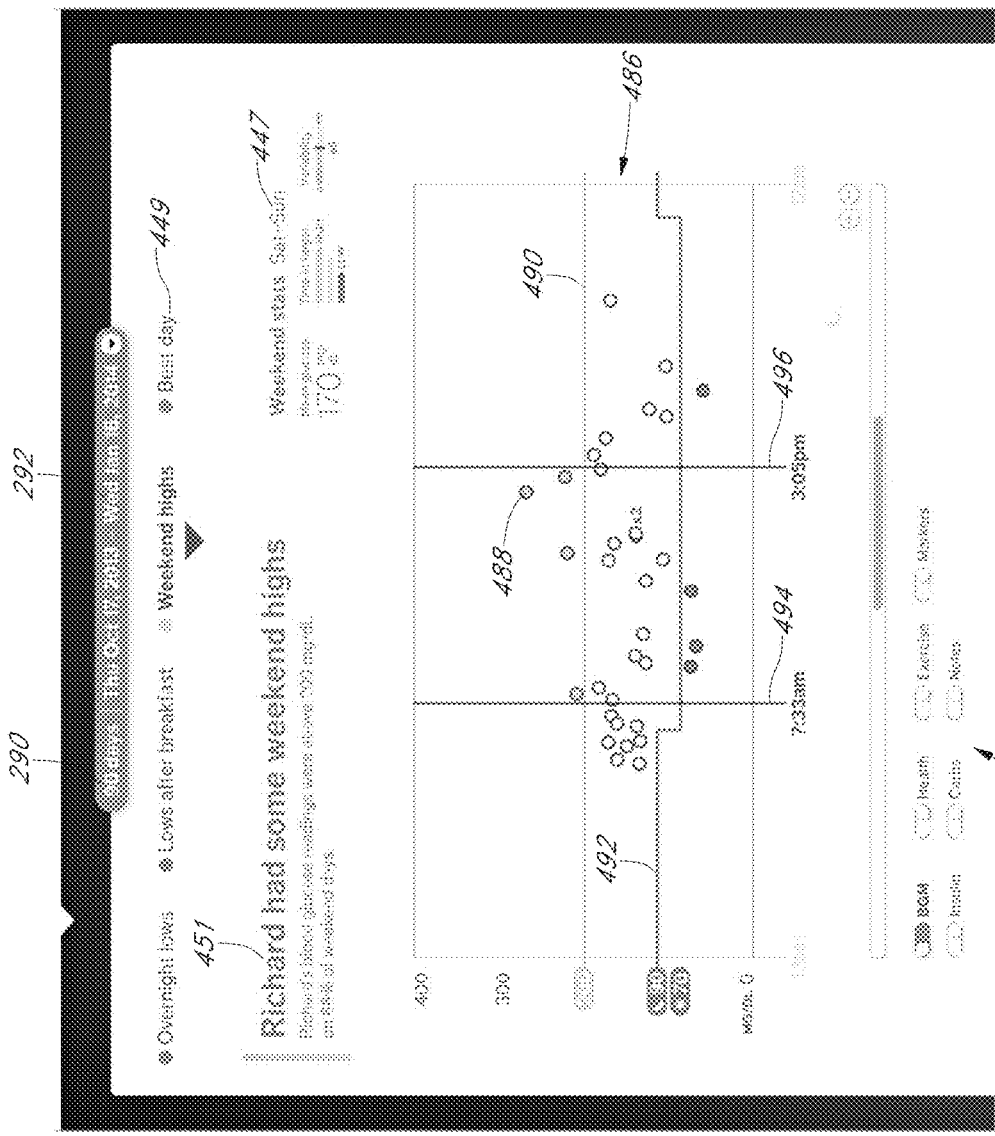
FIG. 25 is an exemplary user interface of a dynamic reporting system according to present principles, showing data patterns for BG data over a weekend period of time.

FIG. 25 illustrates a pattern window 1300 in which a pattern chart 486 is displayed dynamically created from just SMBG data. As with the CGM data, a high threshold 490 and a low threshold 492 (the low threshold varying) are illustrated in the chart 486, along with a number of data points 488. Other elements are shown, which have been described above. The pattern is indicated by the textual description 451, and can be seen in the chart by a number of points appearing above the high threshold at a certain common period of time, e.g., during the day on a weekend. Such may be illustrated by dots having a common color with the high threshold. A time period over which the highs occurred is dynamically indicated by displaying lines 494 and 496 between which the high occurred.

Figure 26:
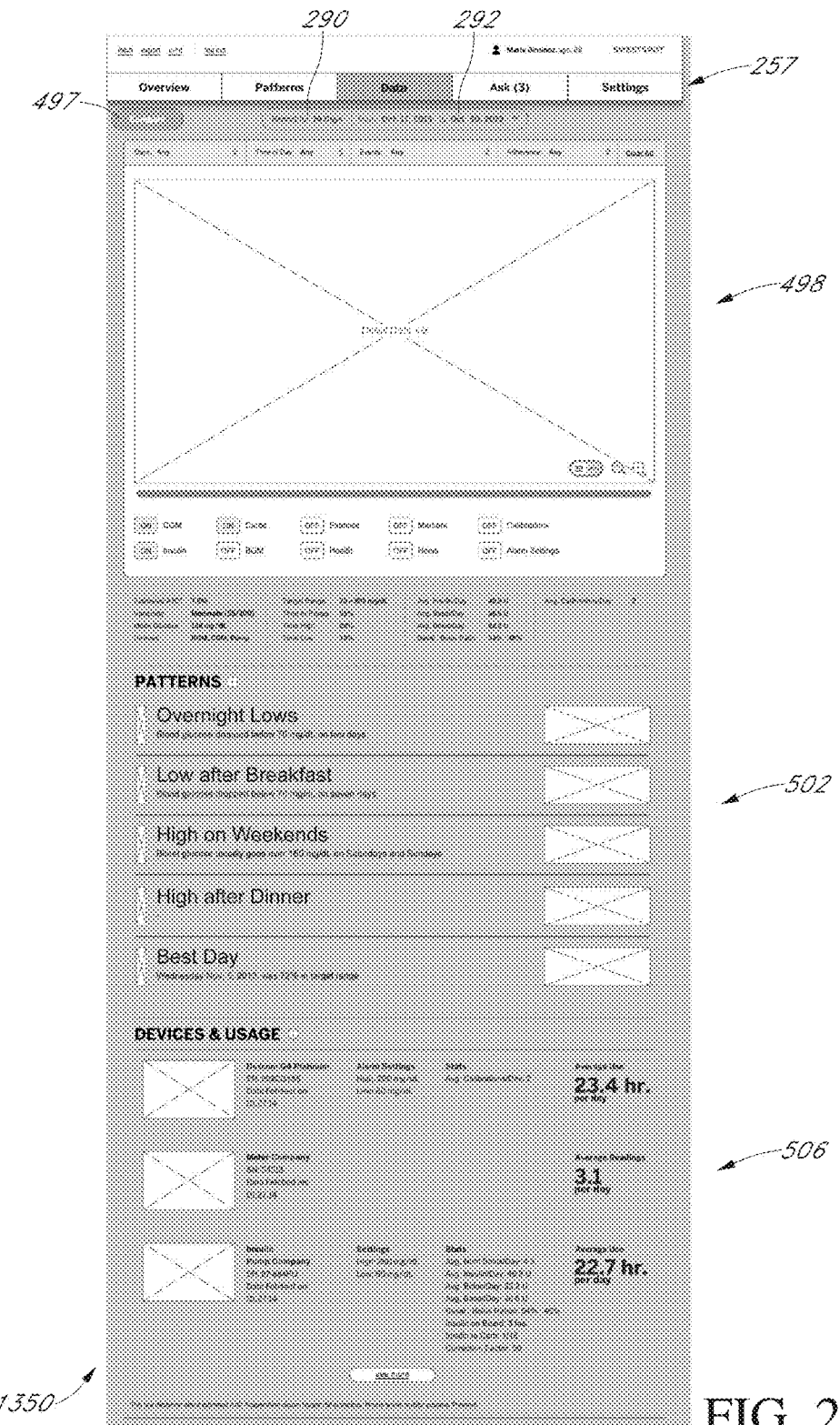
FIG. 26 is an exemplary user interface of a dynamic reporting system according to present principles, including expandable windows for patterns and device usage.

Turning to data analysis, FIG. 26 illustrates an initial view 1350, in wire frame form, of a data portion of a dynamic report, the data portion being selected from the navigation bar 257. In general, the data view allows a user to drill down into the data to obtain additional information about the same, such as more detailed pattern data, information about devices and usage, and so on. The user may further modify time frames to obtain information about devices and events occurring over various periods of time.

In the data view 1350, which has certain similarities to the pattern view, a portion 498 may be reserved for data analysis as will be described. As with the pattern view, a series of patterns may be provided in a pattern window 502. A devices and usage section 506 may be provided to indicate to a user the devices used in from which data may have been received in the data analysis and the creation of the dynamic report. Using timeframe indicators 290 and 292, as described above, a user can select a particular time period and view data associated with that time period. Such data may include fields as noted above including patterns for the selected timeframe, device usage over the time frame, comments entered by the user, and so on. A button 497 allows a user to view data associated with multiple time periods, such as for purposes of comparison.

Figure 27A:
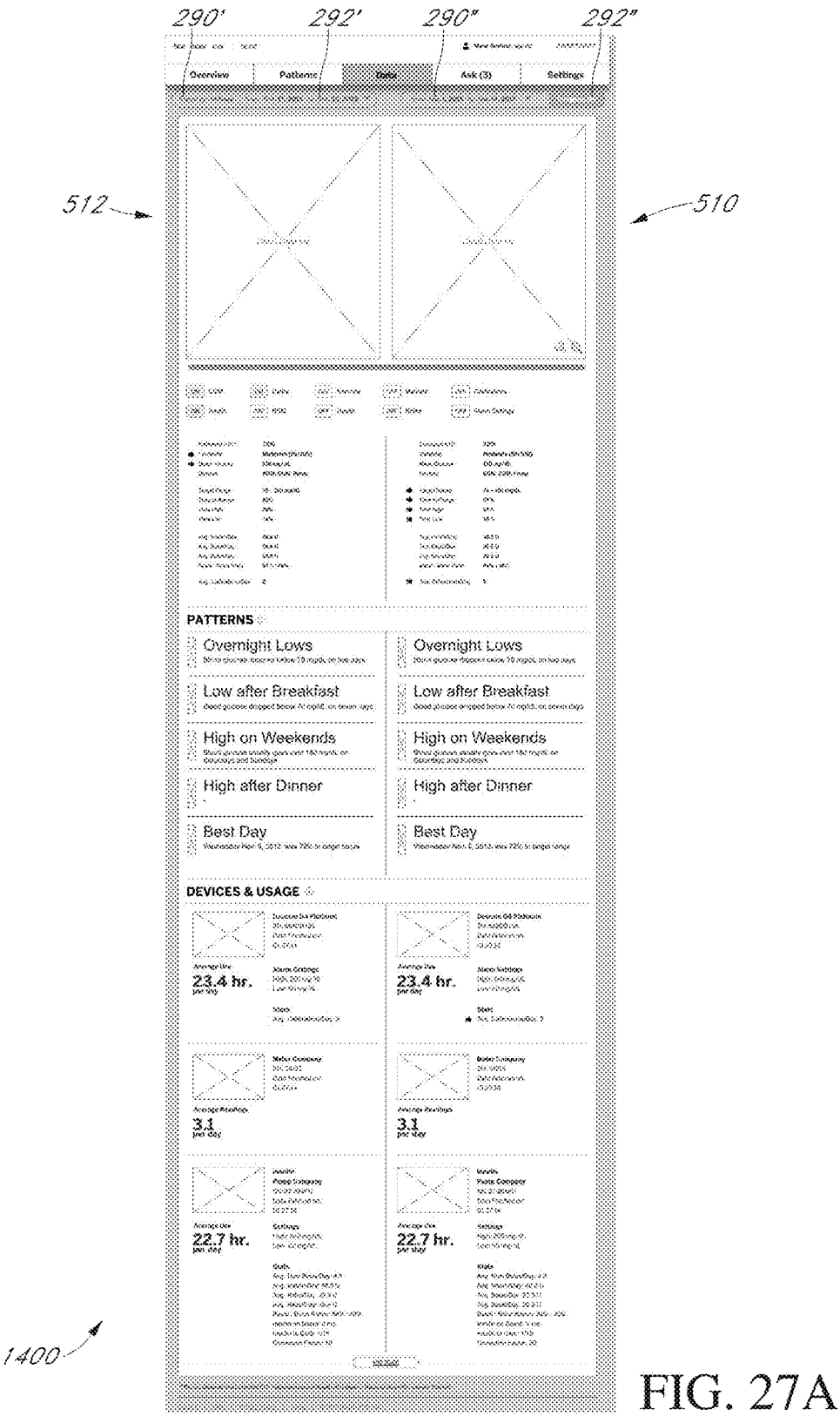
FIG. 27A shows an exemplary user interface of a dynamic reporting system illustrating a comparison of patterns over different periods of time.
Figure 27B:
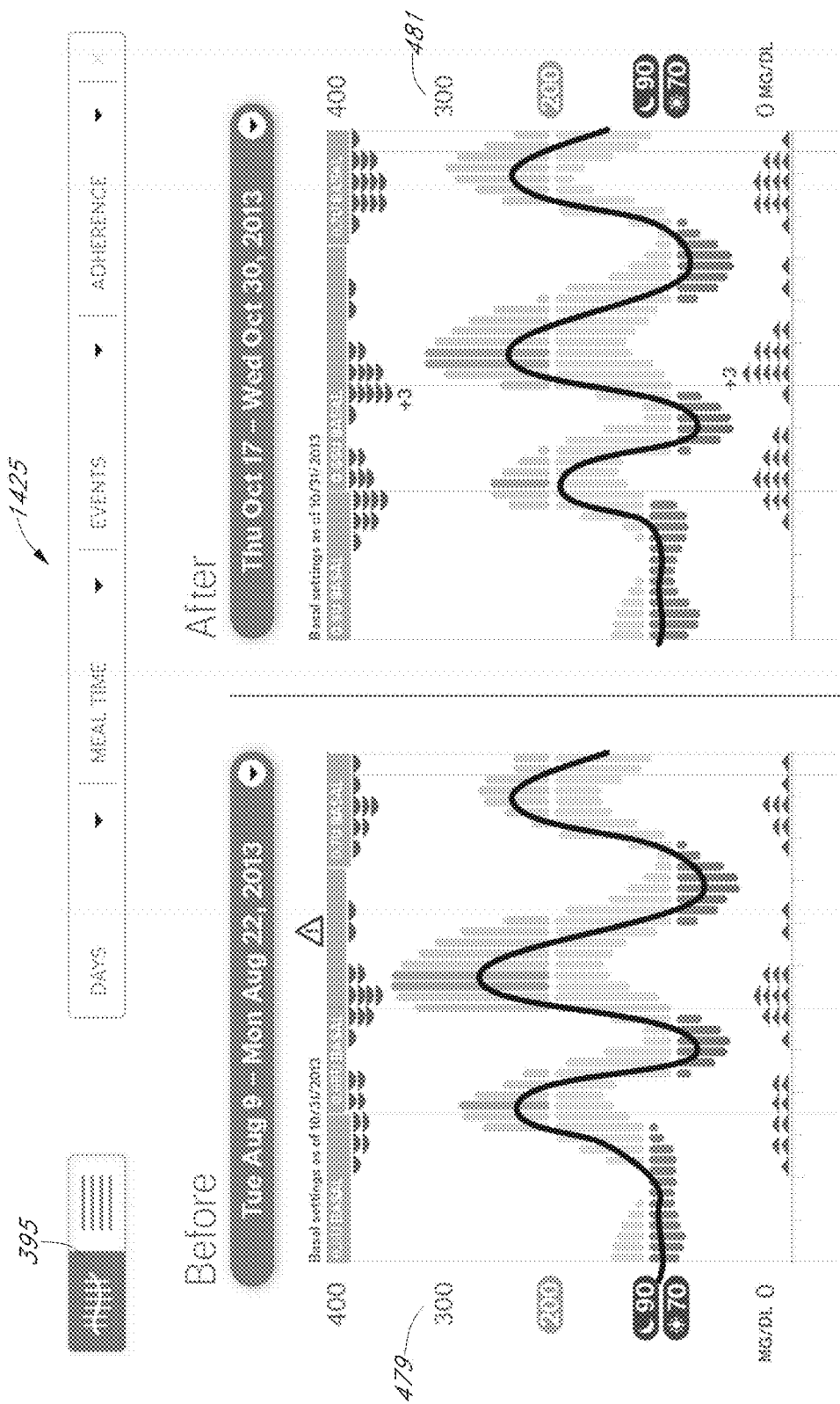
FIG. 27B shows another exemplary user interface of a dynamic reporting system illustrating a comparison of more detailed patterns over different periods of time.

In more detail, FIG. 27A illustrates the "compare" functionality accessed by the button 497 of FIG. 26. In this aspect, the exemplary data analysis portion 498 is replaced with data from two time periods 510 and 512, which are to be compared. The user can select the time periods using selection tools 290', 292', 290", and 290"'. The time periods shown can be "sliding windows" of time, and can thus be adjusted in duration and starting point (equivalently, ending point). While the compared time periods are arbitrary, the user can select the same so as to illuminate the effects of various modifications or events. For example, the user may modify the time periods to illuminate the effects of a medical intervention, attempted lifestyle changes, or the like. For example, the user may find it informative to compare the week/month before a doctor's appointment and the week/month after, or the user may compare a workweek versus a weekend, a week before and after a holiday, or successive weekends to gauge improvement, and so on. While in some cases the time periods compared are equal in duration, in other cases the durations will vary.

In a specific implementation, when data is compared before and after doctor visits, the date of the doctor visit may be retrieved from the doctor's calendar, e.g., as may be available from the multi-patient management portal 128, and in particular from administration block 220. Such data may also be available from a user's calendar.

The systems and methods according to present principles may then, upon entry of a new time period or periods, automatically employ the existing data, e.g., base glucose concentration data, the time period data, event data if any (either entered or previously recognized for the time period), device usage data, user-entered data, etc., in a recalculation and potential re-recognition of patterns and other parameters, e.g., derived variables, appropriate to the entered time periods. The systems and methods may further be configured to, upon recognition of patterns, display the pattern and/or compared patterns as described above.

As can be seen, charts may be compared as may be patterns detected during the time frame encompassed by the different charts, and further as may be the devices and usage employed during the timeframe encompassed by the different charts. Various statistical data are also illustrated for comparison below each chart, and the same can include, e.g., estimated or actual A1C, variability, mean glucose value, target range, time in range, time out of range (high), time out of range (low), average insulin per day, average basal rate per day, average number of boluses per day, a basal/bolus ratio, average carbohydrates per day, and so on. An exemplary comparison window 1425 is illustrated by the pattern charts 479 and 481 in FIG. 27B.

Figure 27C:
FIG. 27C shows another exemplary user interface of a dynamic reporting system illustrating a comparison of patterns over different periods of time.

FIG. 27C shows additional detail about an exemplary comparison 1475 of textual indications of pattern lists 487 and 489. As may be seen, the pattern of "highs after breakfast" in patterns list 487 is no longer present, as indicated by a strikethrough of element 491, in pattern list 489. On the other hand, a new pattern 493 has been identified and thus added to a pattern list 489, this pattern indicating "highs after meals". The use of a strikethrough as applied to a noted pattern can be employed to give helpful encouragement to a user, pointing out a clear "success" achieved by the user and recognized in a dynamic fashion by the systems and methods according to present principles. The system (and thus, user) visualizes the pattern and also visualizes that the pattern was addressed and overcome. Of course systems and methods disclosed may similarly note the negation of good patterns as well as bad ones.

While the displayed time period or time frame can be selected by default, the same can also provide a useful tool for users, caregivers, and HCPs. For example, time periods can be selected based on an event, where the event is a doctor's appointment, an adjustment in therapy, or the like, and the comparison tool used to determine the effect of the altered situation on the patient's status.

Figure 28:
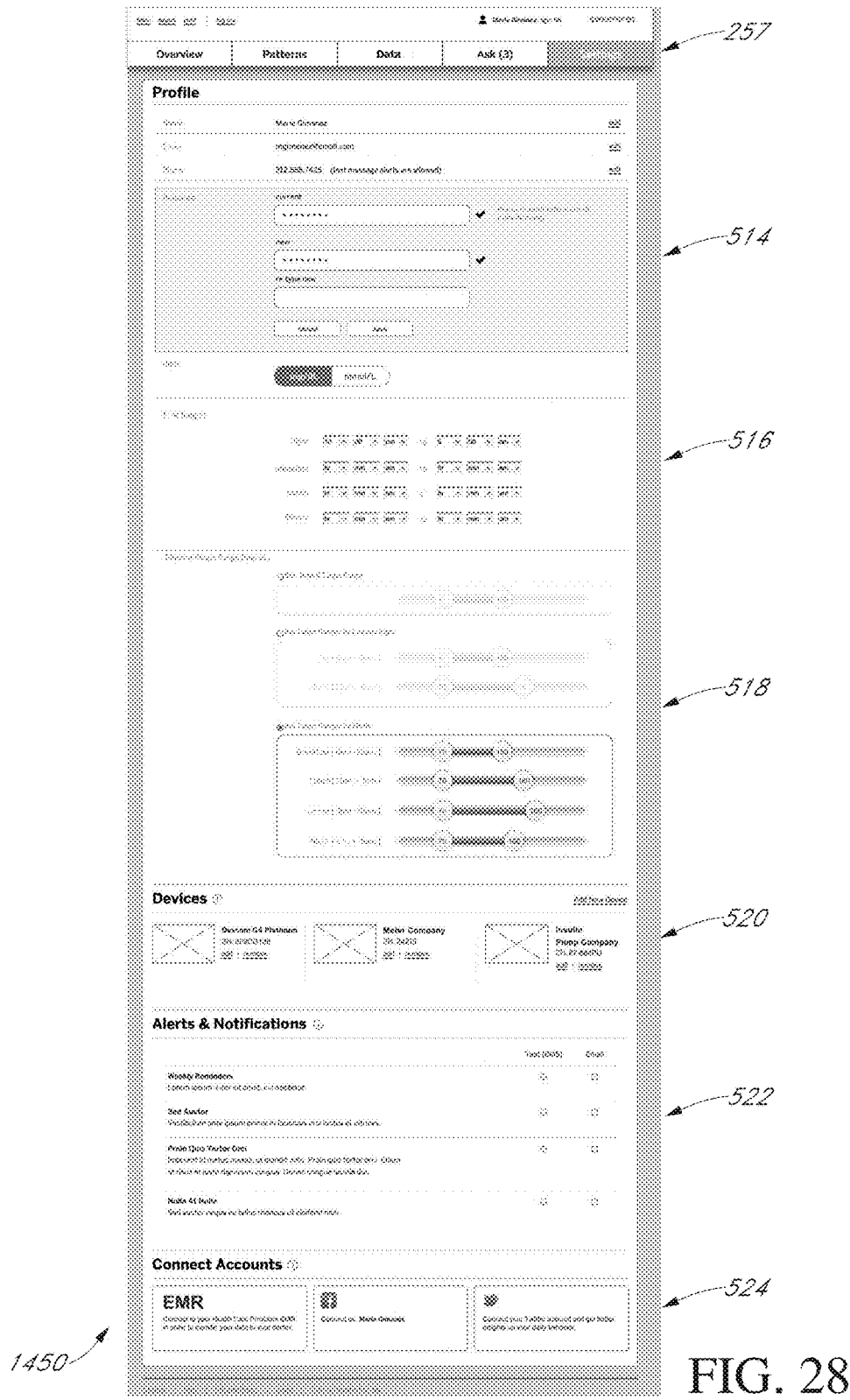
FIG. 28 shows an exemplary user interface of a dynamic reporting system, and in particular a profile edit screen.

FIG. 28 shows a "SETTINGS" landing page including a user profile (see also FIG. 2B at blocks 147, 148, and 151; and FIG. 3 at the same blocks as well as blocks 149, 158, 162, and 166). Patient identifying information, including e-mail address, username, and password, may be entered in section 514. The user may choose whether they wish to see glucose values in mg/dL or mmol/L. Default or usual time periods for meals may be entered in section 516. Target ranges may be entered in section 518, including overall target ranges and target ranges after meals. Targets may also be independently set for different time periods, e.g., for the low threshold, e.g., a daytime value and a nighttime value. Devices employed by a user may be entered in section 520. Alerts and notifications may be set in section 522, and the same may include settings for text messages or e-mails for weekly reminders, alerts or alarms for the user, as well as for caregivers or clinicians, and the like. A section 524 may be provided to allow the user to link the reporting system with various accounts, including EMR accounts and social networks. Settings may be configurable by the user, a caregiver, or an HCP, as appropriate, with permissions given to certain users to edit certain fields.

Figure 29:
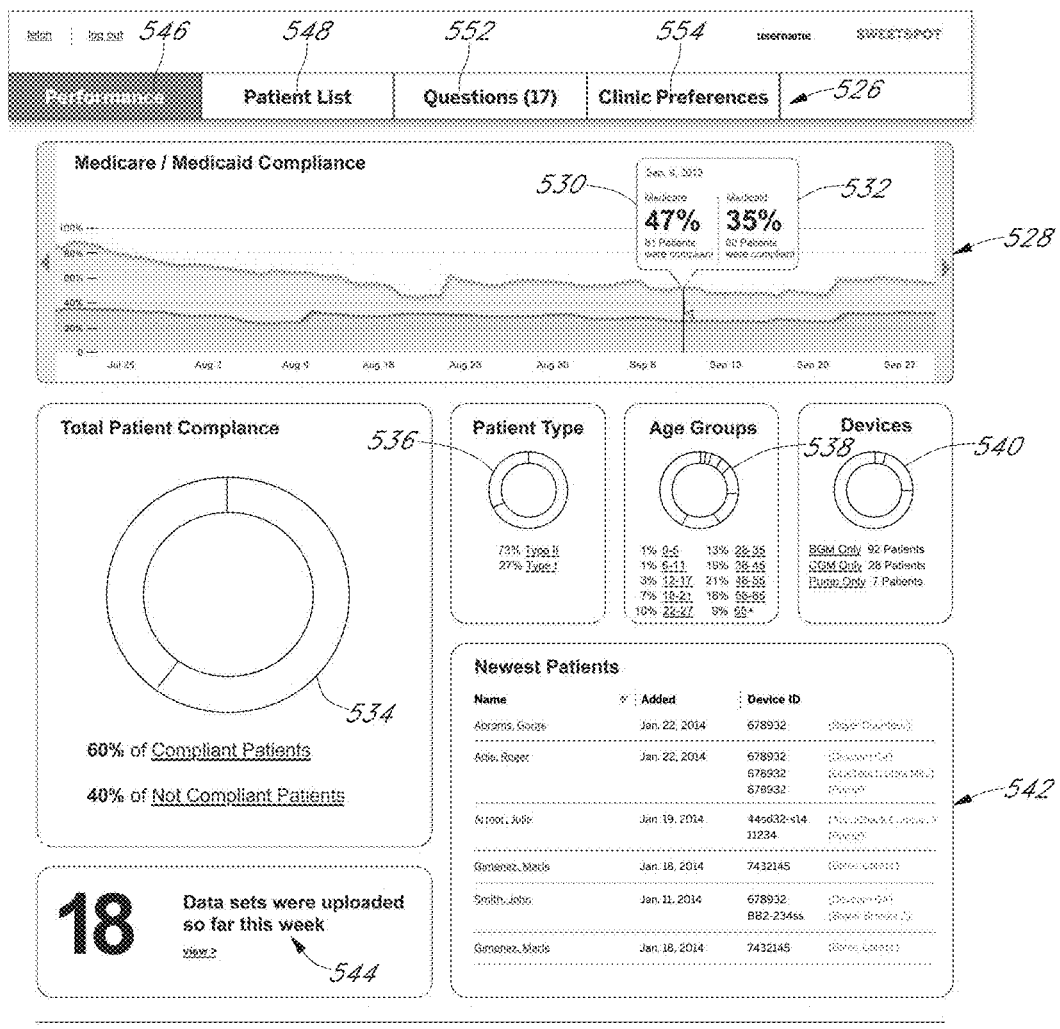
FIG. 29 shows an exemplary user interface of a dynamic reporting system, and in particular for use by an HCP, for monitoring a group of patients.

Certain aspects particular to an HCP view were described above in connection with FIG. 4. These aspects are described in greater detail below with respect to FIG. 29, which shows a view accessed upon selection of a multi-patient management block 128 (see FIGS. 2B and 4). First, activation or selection of a PERFORMANCE tab 546 on a navigation bar 526 may lead to performance view 1500. Other tabs may be provided, such as to access a patient list 548, a list of questions by patients 552, and clinic preferences 554.

The performance view 1500 may have a number of aspects, including an insurance compliance section 528, a total patient compliance section 534, an indicator of a breakdown of patient type 536, an indicator of patients by age group 538, an indicator of patients by devices used 540, a list of newest patients 542, and an indicator of a number of data sets uploaded 544. It each case, selecting a field may serve to navigate the user to a view containing more information associated with that field.

The insurance compliance section 528 may include a chart showing patient compliance with various insurances as well as percentage breakdowns 530 and 532 per insurance type. The total patient compliance may indicate, as a pie chart and/or by percentage, the number of patients that are compliant versus non-compliant. The patient type section 536 may indicate by a percentage the number of patients who are type I versus type II diabetes. The age group section 538 may indicate by a pie chart and percentages age ranges of the patients treated by a clinician or clinic. The devices section 540 may indicate by pie chart and percentage which patients are using particular devices, or combinations of devices.

The list of newest patients 542 may indicate the names of newly added patients, as well as one or more summary details about the same. The indicator 544 may indicate new data sets added to the reporting system. Such data may alert the HCP that reports created for patients with new data sets will generally be "new" in the sense that the dynamic reporting system will generally show new results.

In general, the performance view can be dynamically generated based on new data from patients, as well as being based on a ranking or prioritization scheme instituted by a physician, or clinic. That is, the position or clinic may edit settings, such that reports about multiple patients are dynamically generated in a way that pertinent data, i.e., especially important data, about the multiple patients is brought to the forefront, commanding the clinician's attention. Exemplary factors may include, e.g., a degree to which diabetes is in control or out of control, calendaring data, e.g., all patients to be seen on a given day, a degree to which patients are compliant or noncompliant, a list of patients who have had significant glucose concentration value excursions, and so on.

Figure 30:
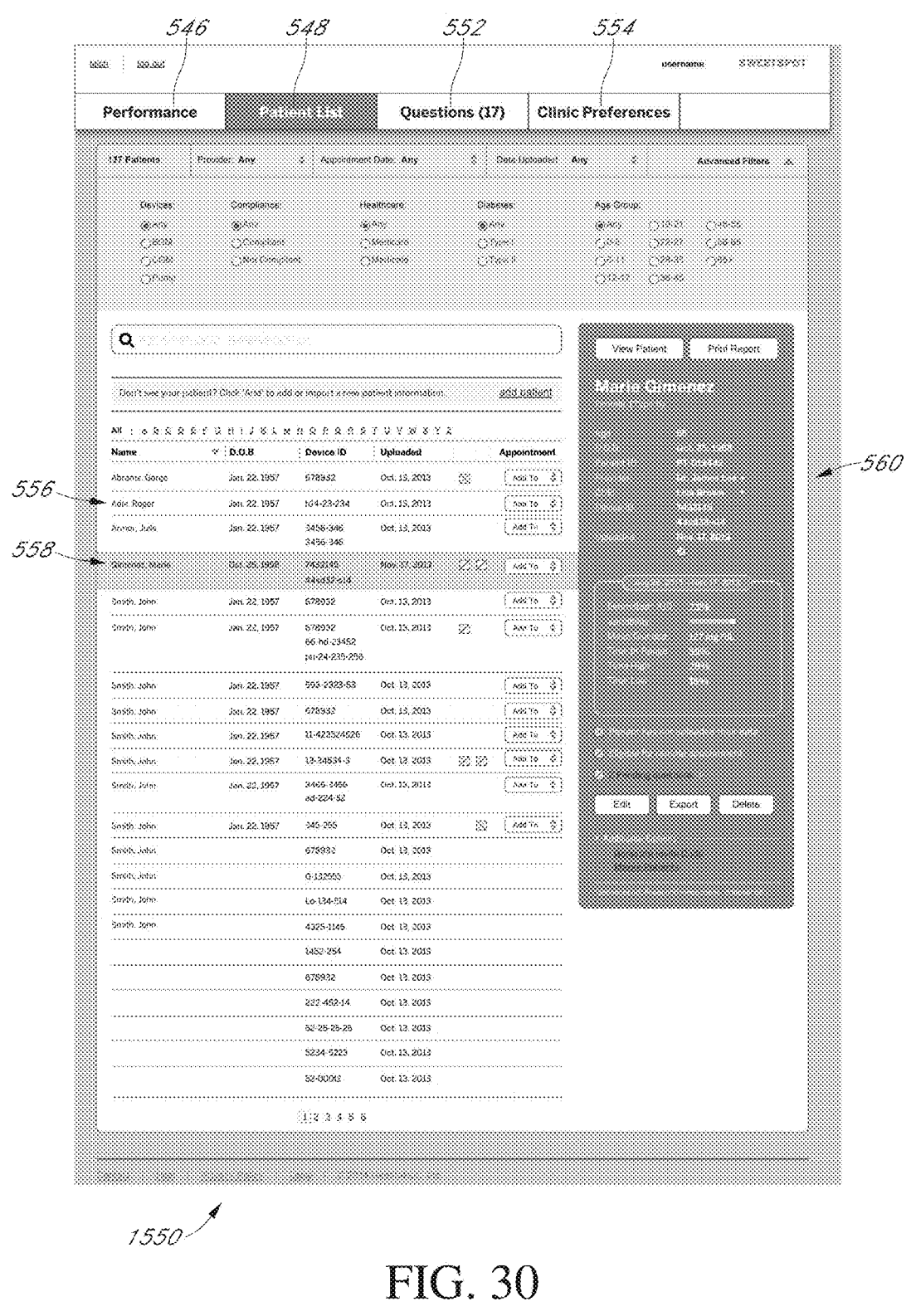

Selecting or clicking on the patient list tab 548 generally brings up a list of patients 556, shown by the window 1550 of FIG. 30. The list 556 may be sorted in a number of ways, including alphabetically. A search field may be provided to search for particular patients by name, or by information associated with a patient. In using search or other filtering techniques, the system may receive one or more criteria related to patient data, and compare the received criteria against data records in a database comprising a set of patient records. The system may then determine and display for viewing in the user interface one or more patient records that meet the received criteria. The criteria may include, e.g., age, weight, gender, insurance, length of time as a patient, type of malady, devices used to monitor or treat a malady, events associated with the patient, a therapy regime, criteria related to user malady treatment performance, or combinations of the above. Other criteria will also be understood.

The same techniques may also be employed to determine and display data about patient compliance, and in this case the criteria may be related to patient compliance with a therapy regime, e.g., accuracy of device usage, overall time of device usage, accuracy of calibration measurements with respect to a suggested calibration time, number of calibrations, user acknowledgment of alarms, accuracy of medicament administration, or combinations of the above. Other criteria will also be understood.

The view 1550 may include the patient name, date of birth, device ID, the last time data was uploaded, appointment status, or the like. A particular patient may be highlighted, as shown by highlight 558. In this case, additional or expanded information may be displayed about the patient in a sidebar 560. Additional information may include their clinician, insurance information, whether they have questions pending, or the like. Within the sidebar 460, clicking on a VIEW PATIENT button may lead to additional information being displayed about the patient, including a view in which only information about that selected patient is displayed, e.g., the overview view, pattern view, data view, questions/comments view, settings view, and the like, discussed herein.

Figure 31:
FIG. 31 shows another exemplary user interface of a dynamic reporting system, for use by an HCP, for monitoring a group of patients, showing filter options.

Referring to the view 1600 of FIG. 31, a filter section 562 may be displayed and employed to examine a chosen group of patients. By clicking on one of the radio buttons 563*i* provided, the list of patients may be filtered to only include and display patients fitting the criterion noted with the radio button. Particular radio buttons may include, e.g., whether the patient uses a SMBG meter (563*a*) or a CGM (563*b*), whether the patient uses a pump (563*c*), patient compliance, insurance, patient type (type I (563*d*) versus type II (563*e*)), age group, or the like.

Selecting or clicking on the questions tab 552 leads to a listing of pending and/or answered questions, which the clinician may answer as a group or may filter by patient to address a particular patient's questions all at one time. Other variations of ways to organize the answering of questions will also be understood.

Figure 32:
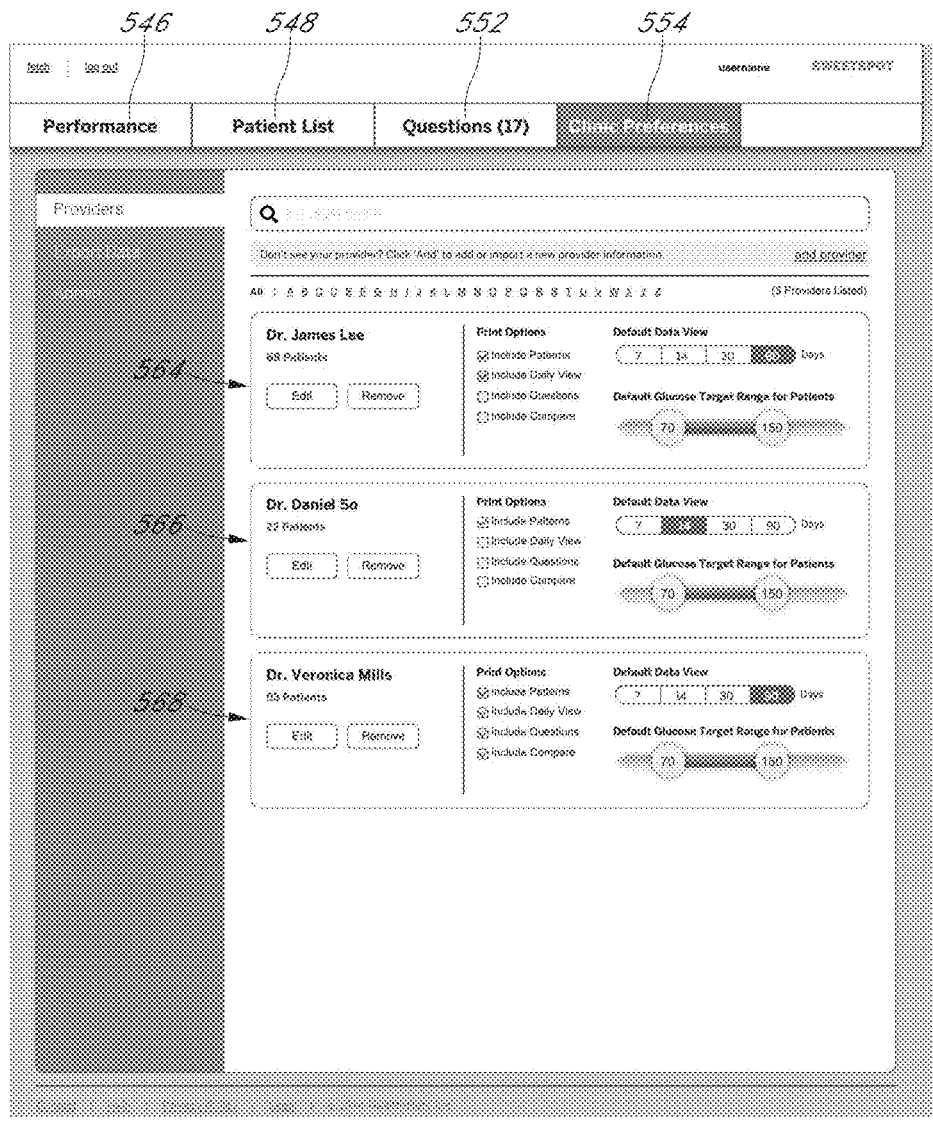
FIG. 32 shows another exemplary user interface of a dynamic reporting system, for use by an HCP, for monitoring and editing information about clinicians within a clinic.

Selecting or clicking on the clinic preferences tab 554 brings up (see FIG. 32) a window 1650, which may list, among other items, clinicians 564-568 associated with a given clinic, and their respective preferences. For example, each section may list a number of patients associated with the clinician, the particular print options the respective physician prefers, e.g., whether to include patterns, questions, comparisons, or the like. Clinicians may be enabled to select a default data view, e.g., a number of days to be covered, a preferred default glucose target range for one or more patients, and so on.

Figure 33:
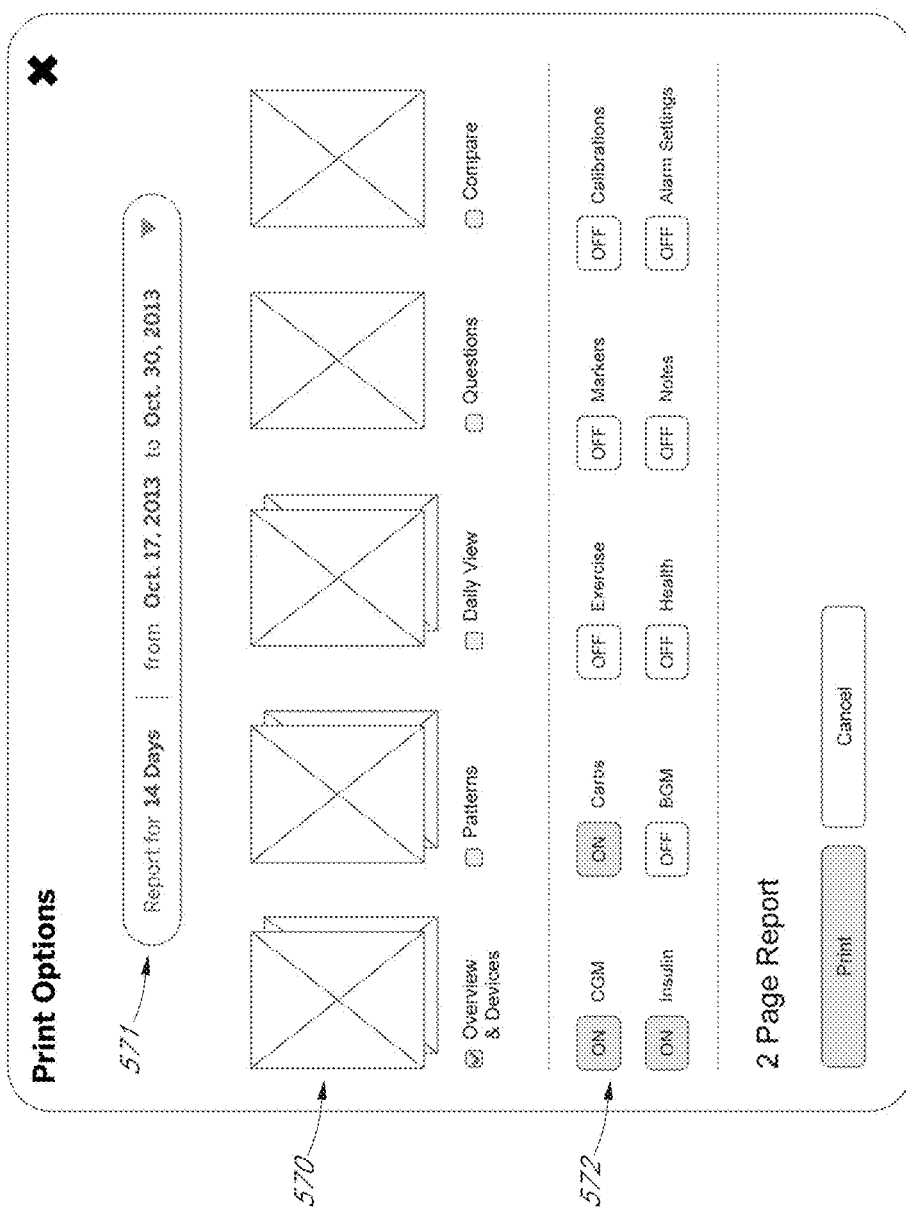
FIGS. 33 and 34 illustrate the setting of print options for dynamic reports according to present principles.

To provide specific options for printed reports, a print options view 1700 may be employed as shown by FIG. 33. The print options view 1700 may include a date range for printout 571, a list of various default print options 570 (shown in wire frame in FIGS. 33 and 34), and buttons 572 to allow selective inclusion of various particular parameters. The default print options may include any number of combinations of views described. In the example of FIG. 33, the print options view 1700 can provide specific options 570 for overview and devices, patterns, data, questions, and comparisons. The specific parameters in the embodiment of FIG. 33, which may be selectively displayed in the dynamic report using buttons 572, include data about CGM, SMBG monitoring, carbohydrate ingestion, exercise, health, insulin delivery, calibrations, alarm settings, and notes. The result of inclusion of the data in a report may be subject to the dynamic creation methods described above, e.g., based on availability of data, prioritization/ranking schemes, and so on. The user may also be enabled to create their own print options, according to their needs.

Figure 34:
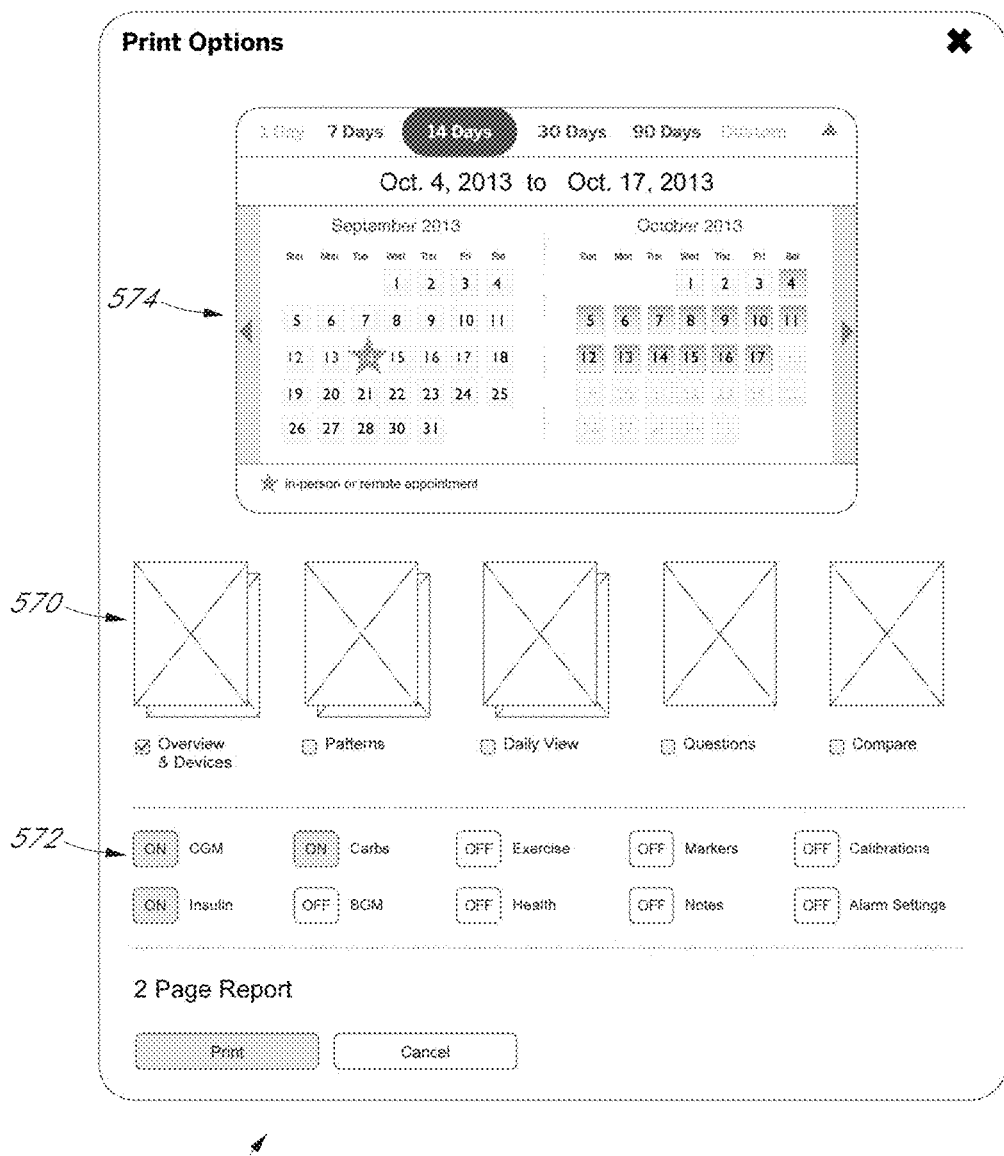

FIG. 34 shows a similar print options view, but the print options view 1750 in this figure includes a calendar interface 574, by which the user can conveniently select dates for inclusion in the dynamic report. The calendar interface 574 may indicate, e.g., by way of a star on a particular date, the next appointment date with a clinician. If data within such the selected date range is not available, the same may be omitted or data fields and visualizations based on such may be placed in a lower priority, according to present principles.

Figure 35:
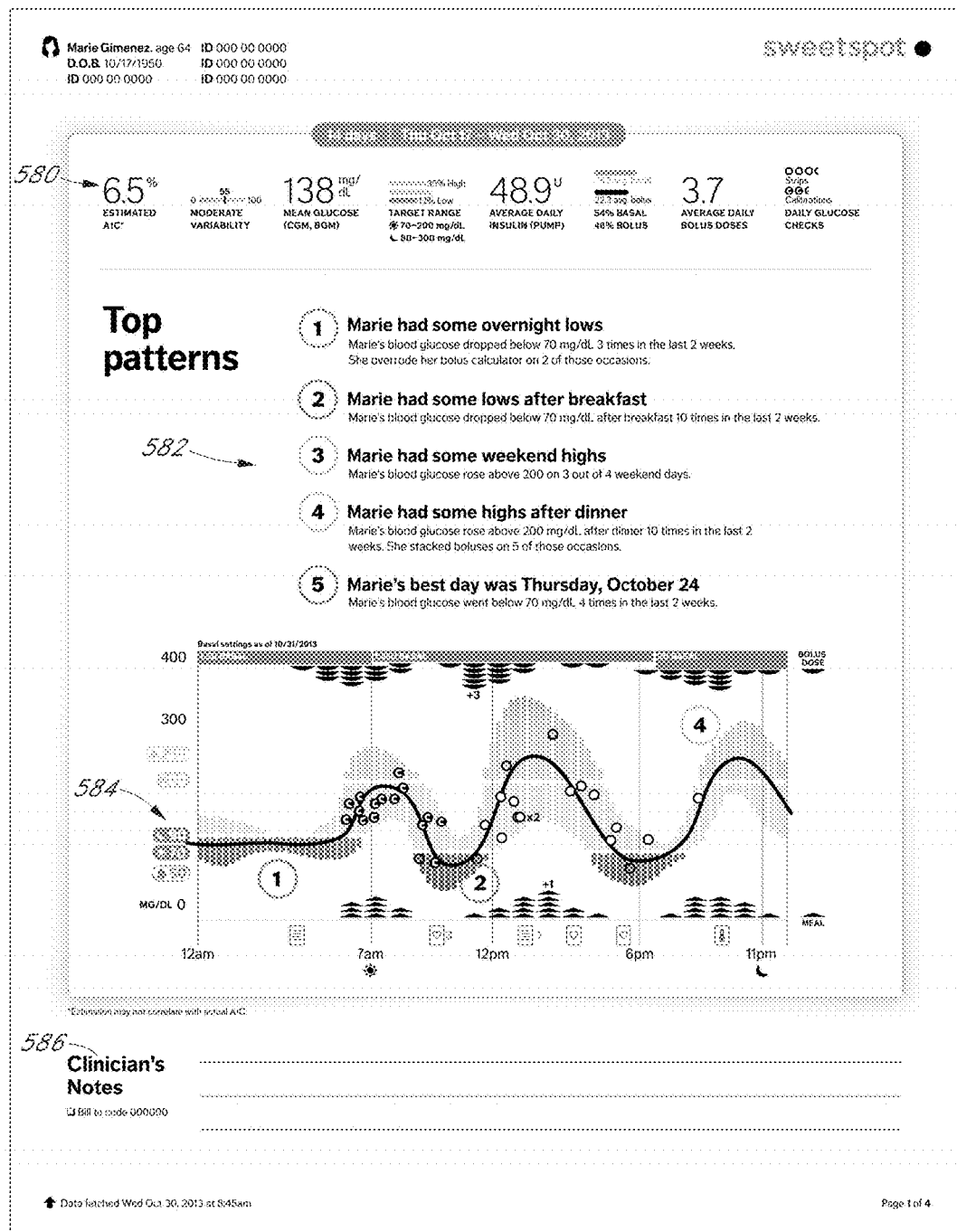
FIG. 35 illustrates an exemplary printed dynamically generated or created report of CGM and other data according to present principles.

FIG. 35 shows a printed dynamic report 1800 that may be particularly useful to guide a doctor-patient conversation. It is noted that such reports, described here with respect to their printed form, may also be displayed on a GUI for similar purposes, with a similar such summary graph 584. The data fields and visualizations within the report are dynamically generated to quickly focus on aspects important to the patient and are further dynamically generated to exhibit in a concise manner, e.g., one or a few pages, topics for discussion. A summary section 580 is provided to give the clinician and patient an immediate examination of the current status of the patient. A pattern section 582 textually indicates patterns of relevance to the patient in a way not only the clinician but also the patient can understand. The textual information further includes specific numbers, time frames, measurements, or the like, which gave rise to the identified pattern. A pattern chart 584 is provided to backup the identified patterns, and to indicate to a user in a graphical and quantitative way how the patterns are occurring, and such may accompany any of the patterns charts described herein, e.g., those in FIGS. 5, 6, 14, 15, 21-27, 35-37, 39-41, 45, and 46. A notes section 586 may be employed by the clinician to write or jot down notes during the doctor-patient conversation, which may later be stored in the patient file, either using the printed report 1800 itself or a scanned-in version. In many cases, the same is helpful if not required in requests for insurance reimbursement.

Figure 36:
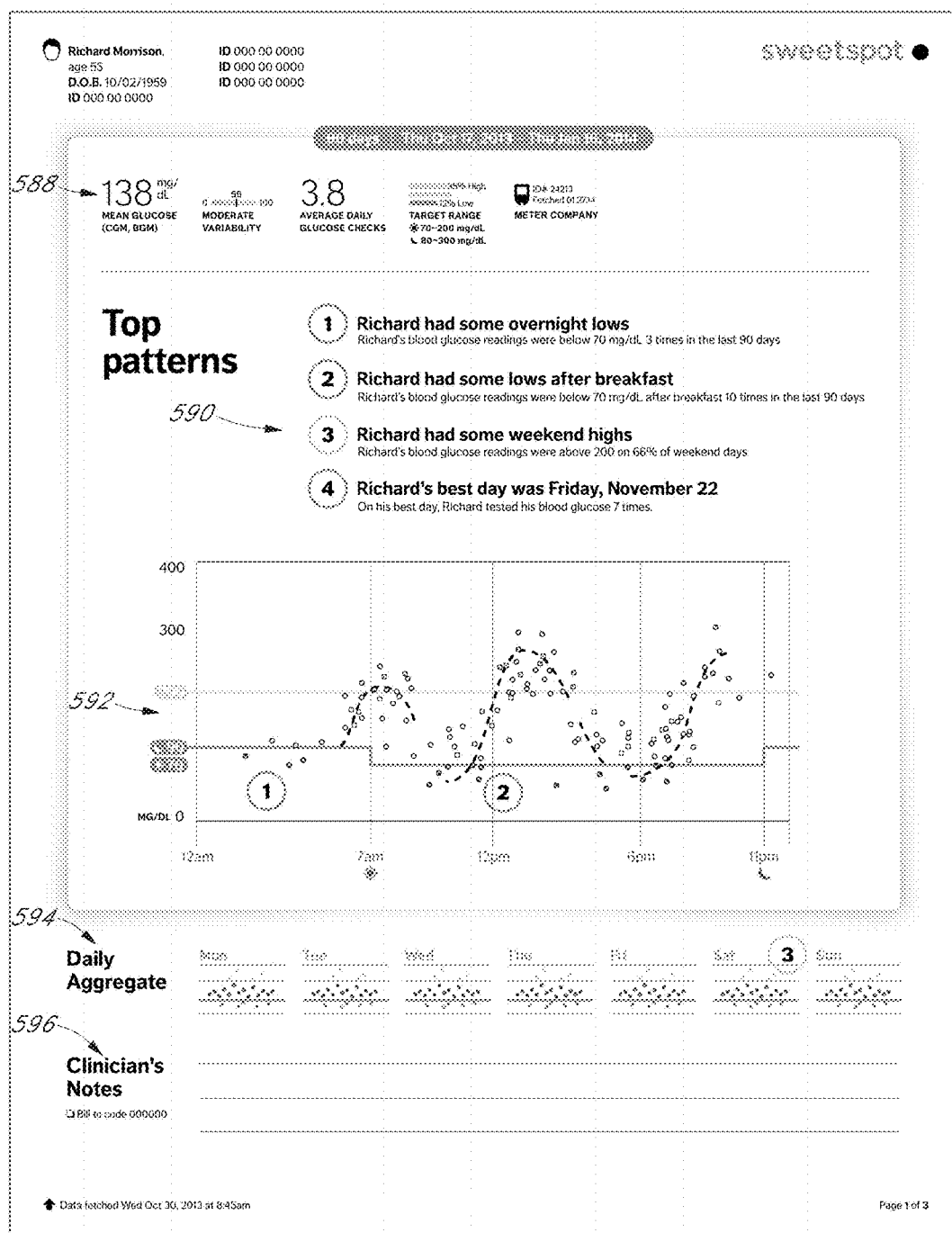
FIG. 36 illustrates an exemplary printed dynamically generated or created report of BG and other data according to present principles.

FIG. 36 shows a similar printed report 1850, but where a user selected to only display SMBG data, (or where only SMBG data was available), and thus the dynamic reporting system only included the same. As with the CGM report, the SMBG report 1850 includes a summary section 588, a pattern section 590, a chart section 592, and a notes section 596. The printed SMBG report 1850 may also include a daily aggregate of data 594, showing a scatter plot of data for each day, organized by day of the week, within the time period. The patterns may be enumerated, and corresponding numbers may appear in the chart or daily aggregate at locations where such patterns may be particularly evident.

Figure 37:
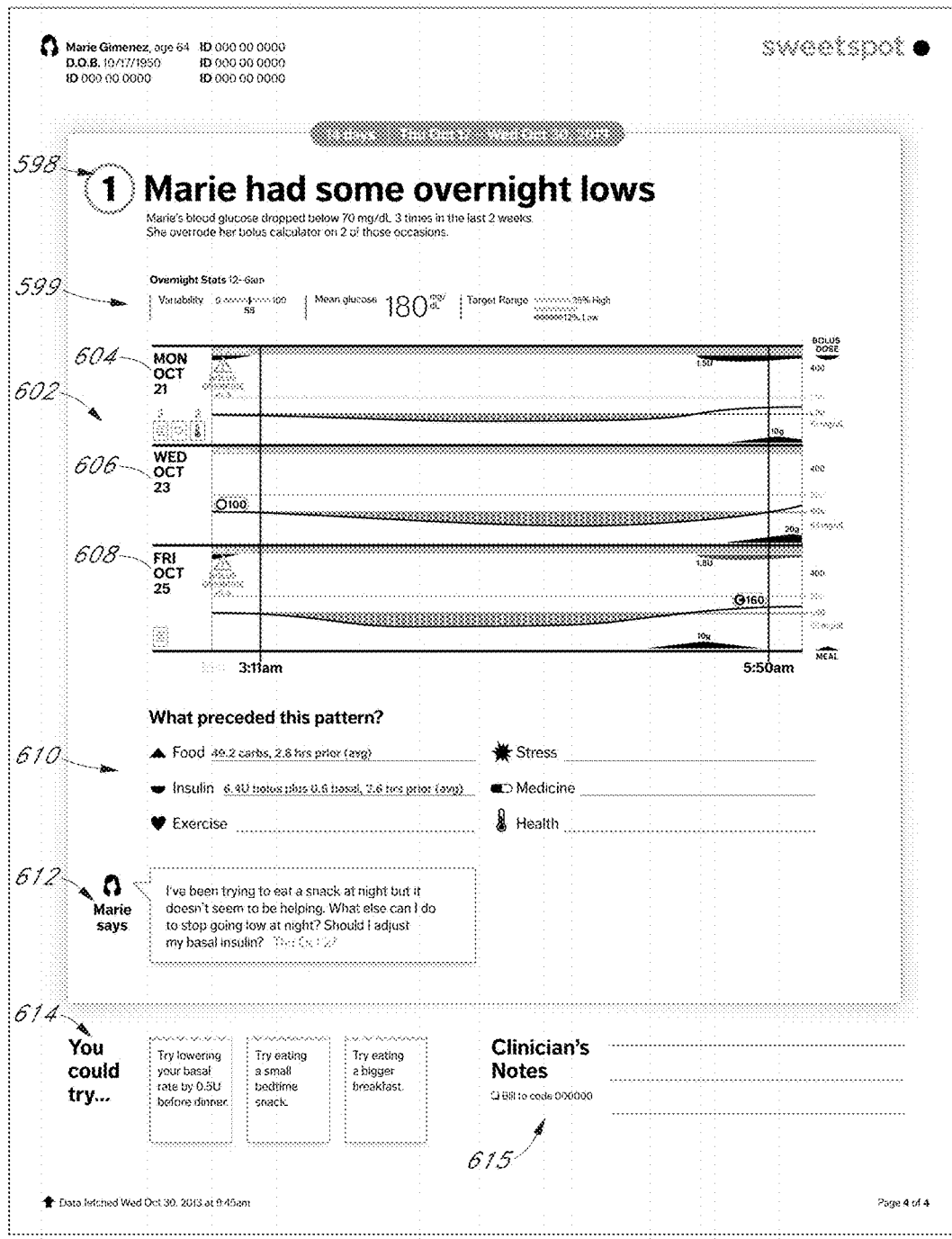
FIG. 37 shows an exemplary printed dynamic report, illustrating a particular pattern within the monitored data, in a set of single day views.

FIG. 37 shows another dynamically created or generated CGM report 1900, where a particular pattern has been "drilled down" to illustrate additional information about, in this case, a pattern of overnight lows. For example, selecting this pattern in the displayed version of report 1800 of FIG. 35 may cause the report 1900 to be generated. In this case, the pattern is illustrated by representative single day view examples 604, 606, and 608. Above the single day views are certain statistics about the pattern, including a mean glucose level, a variability, and durations within and outside of the target range.

FIG. 37 also shows a section 610 for comments, and in the case of section 610 the same prompt for comments by listing certain parameters that may bear on the pattern, e.g., food, insulin, exercise, stress, medicine, and health. In this exemplary figure, the user "Marie" inserted comments about food and insulin, which the HCP may then employ to determine more about the pattern and its causes, as well as potential ways to ameliorate such deleterious patterns in this patient. Suggestions are given in section 614, and the same may or may not be based on the comments provided by the patient. A section 615 for clinician's notes is again provided, where the clinician may typically jot down notes about their conversation with the patient about the pattern or other aspects of disease management.

FIG. 38 shows a report 1925 in which information is provided about devices and usage. In particular, a section 617 shows information about a CGM, a section 619 shows information about a SMBG meter, and a section 621 shows information about a pump. A number of other parameters are displayed about the pump, as may be available. It will be understood that the information provided in the devices and usage section may vary in a number of ways, and that the report 1925 is purely exemplary. In many cases, especially pertinent data may include the usage of each device, i.e., how much or how often each device was used over the chosen or set time period of display. Such may generally be in the form of hours (and fractions thereof) for CGM and pump data, and a number (absolute or average or as a frequency) for SMBG data. In some implementations, data of a secondary priority may include device settings. Settings information may be employed to provide recommendations for the charts, such as, e.g., a recommendation to adjust a basal rate at a certain time, e.g., to lower the basal rate at night. Device settings may be employed for the creation of charts as well, e.g., the display of basal rate as in FIGS. 22-25.

Figure 39:
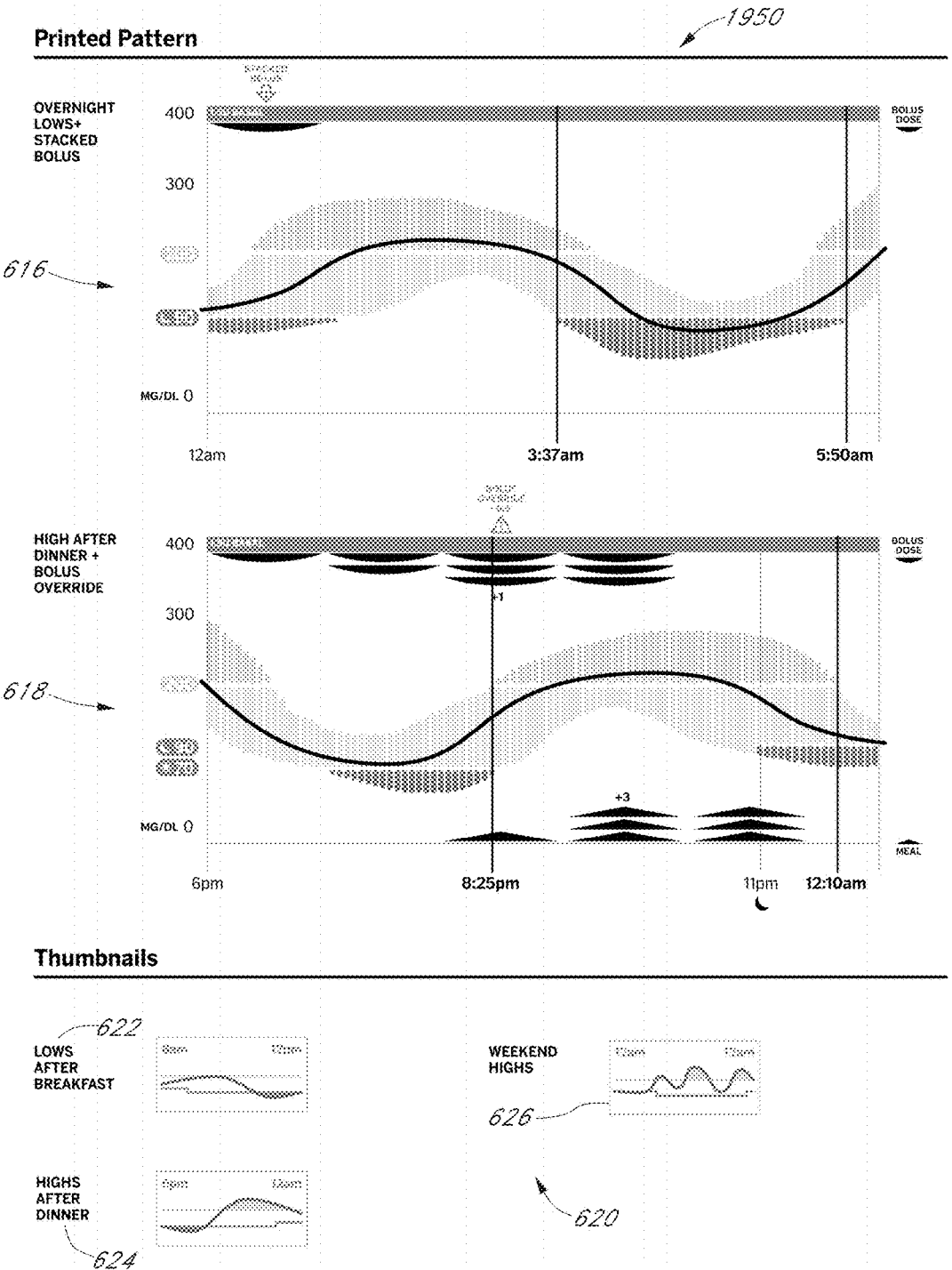
FIG. 39 shows an exemplary printed dynamic report, in particular illustrating patterns within the monitored data.

FIG. 39 shows a printed version 1950 of a report similar to that displayed in FIG. 22. Two larger charts 616 and 618 corresponding to identified patterns are shown in considerable detail, and a series of thumbnails 620 are illustrated for other detected patterns. The chart 616 provides information about overnight lows; the chart 618 provides information about the identified pattern of highs after dinner; thumbnail 622 indicates lows after breakfast; thumbnail 624 indicates highs after dinner; and thumbnail 626 indicates weekend highs. By clicking on any of the thumbnails, the identified and selected pattern may be displayed in greater detail, such as in the larger charts above the thumbnails. The description of aspects of the charts themselves may be seen with reference to the description of FIG. 22.

Figure 40:
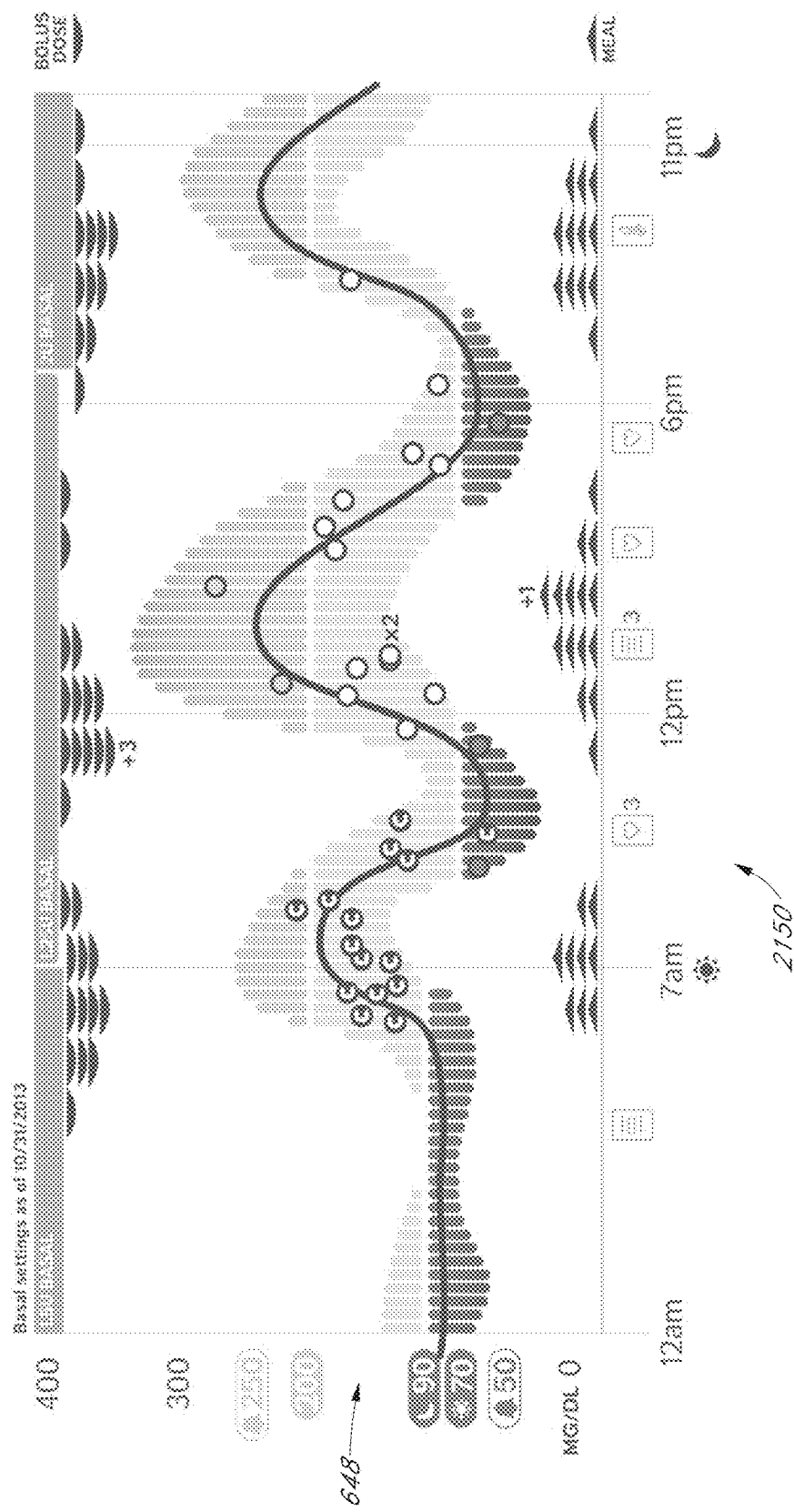
FIG. 40 shows a similar printed dynamic report as FIG. 39, but this chart including calibration points.

FIG. 40 illustrates a similar printed report 2150 including a chart 648, but where this chart further includes a number of calibration points (those marked with a 'C' within the point) as may be determined by SMBG measurements taken for purposes of CGM calibration.

Figure 41:
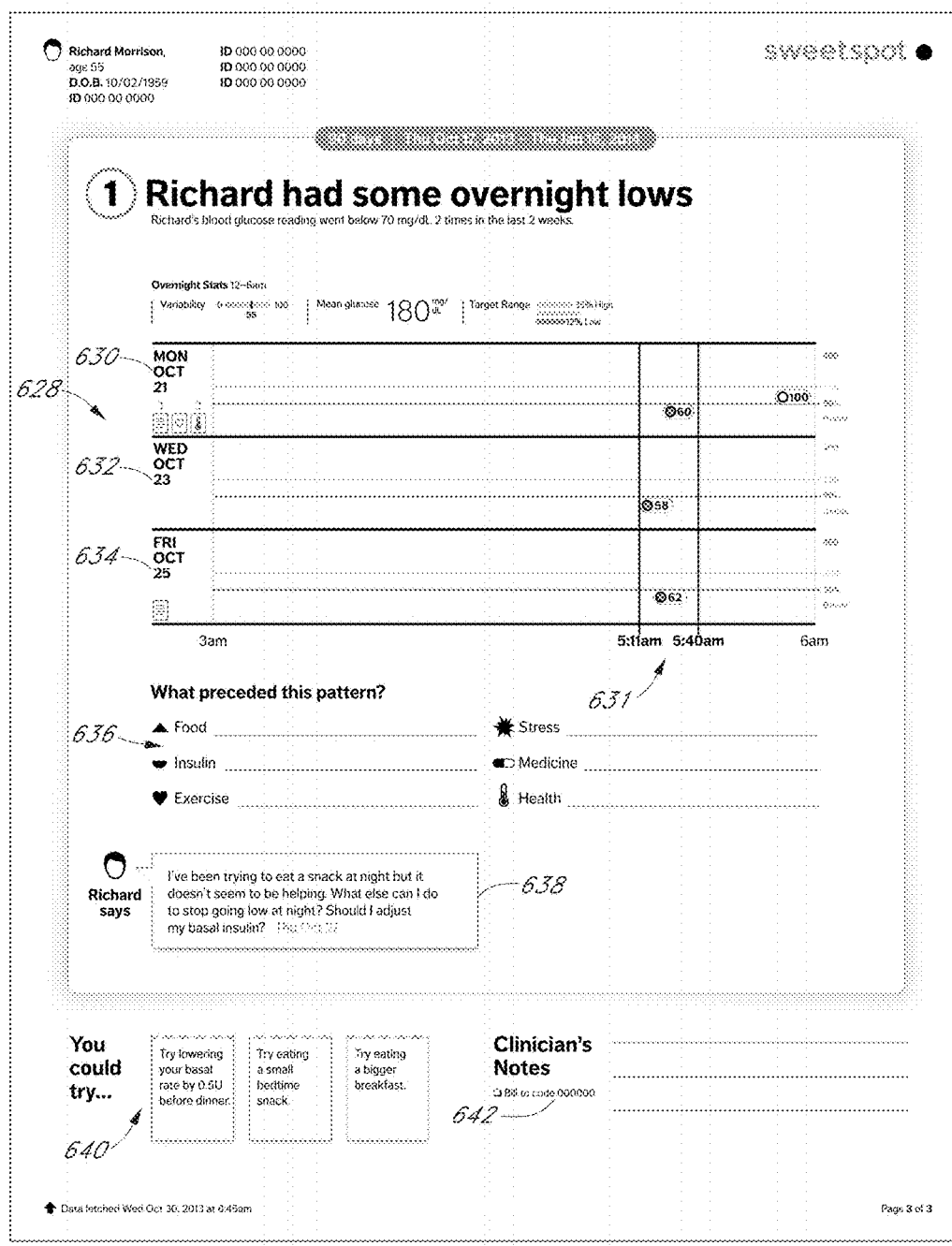
FIG. 41 shows an exemplary printed dynamic report, illustrating a particular pattern within the monitored data.

FIG. 41 illustrates a report 2000 that is generally similar to FIG. 37, but where only SMBG data was selected to be displayed and/or analyzed (or was available), and thus the dynamic reporting system focused on such. In particular, a chart section 628 illustrates three single day plots 630, 632, and 634, which illustrate a low, as evidenced by blood glucose measurements taken within a common time period 631. The report 2000 can include a section 636 for the patient to write notes about what preceded the pattern, as well as a section 638 in which notes, a user entered into the reporting system in attempts to address the pattern, are recorded and reproduced, e.g., for later discussion with an HCP.

Suggestions may be given to the user in section 640, and a section 642 may be provided for a clinician to record notes, such as during a doctor-patient conversation.

Figure 42:
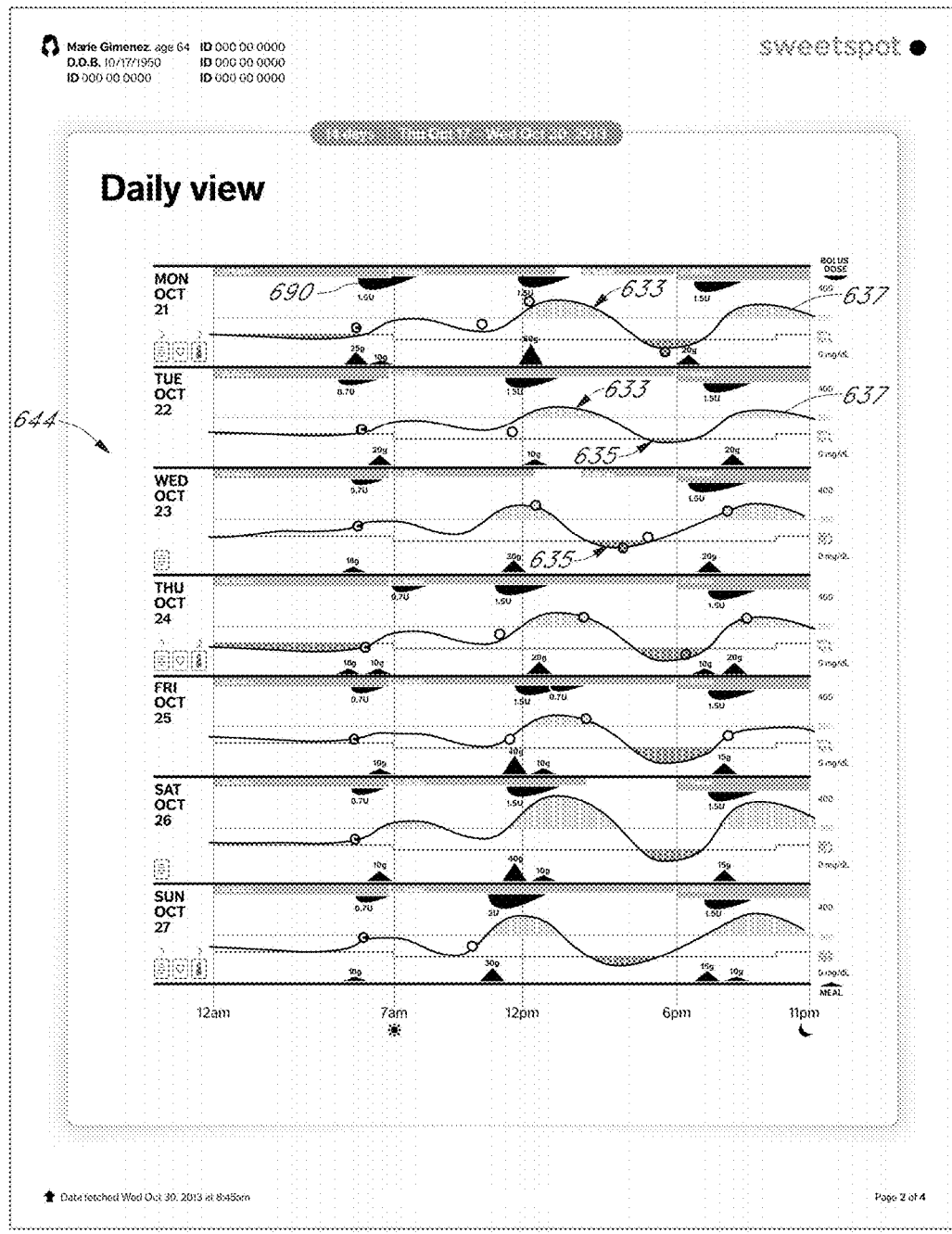
FIG. 42 shows an exemplary printed dynamic report, in particular illustrating a view of a week's worth of monitored CGM trace data.

Dynamically created reports may also be provided in other formats. Referring to FIG. 42, a printed report 2050 may display a plurality of single day views 644, along a common time axis, indicating visually to a user, the occurrence of common patterns. For example, at point 633, a post-meal (lunch) high may be seen as a common pattern. Similarly, an afternoon low may be seen at point 635. Finally, a post-dinner high may be seen at point 637.

FIG. 42 also shows how adjustments can be made to the icons, e.g., their shape or size, to better reflect the effect of insulin or meals on the patient, i.e., the effect of each over time, e.g., by the use of "tails" as described above and as illustrated in the figure as bolus tail 690. A default "effect" value can be employed until better calculations are achievable based on knowledge of a particular user's insulin sensitivity.

Figure 43:
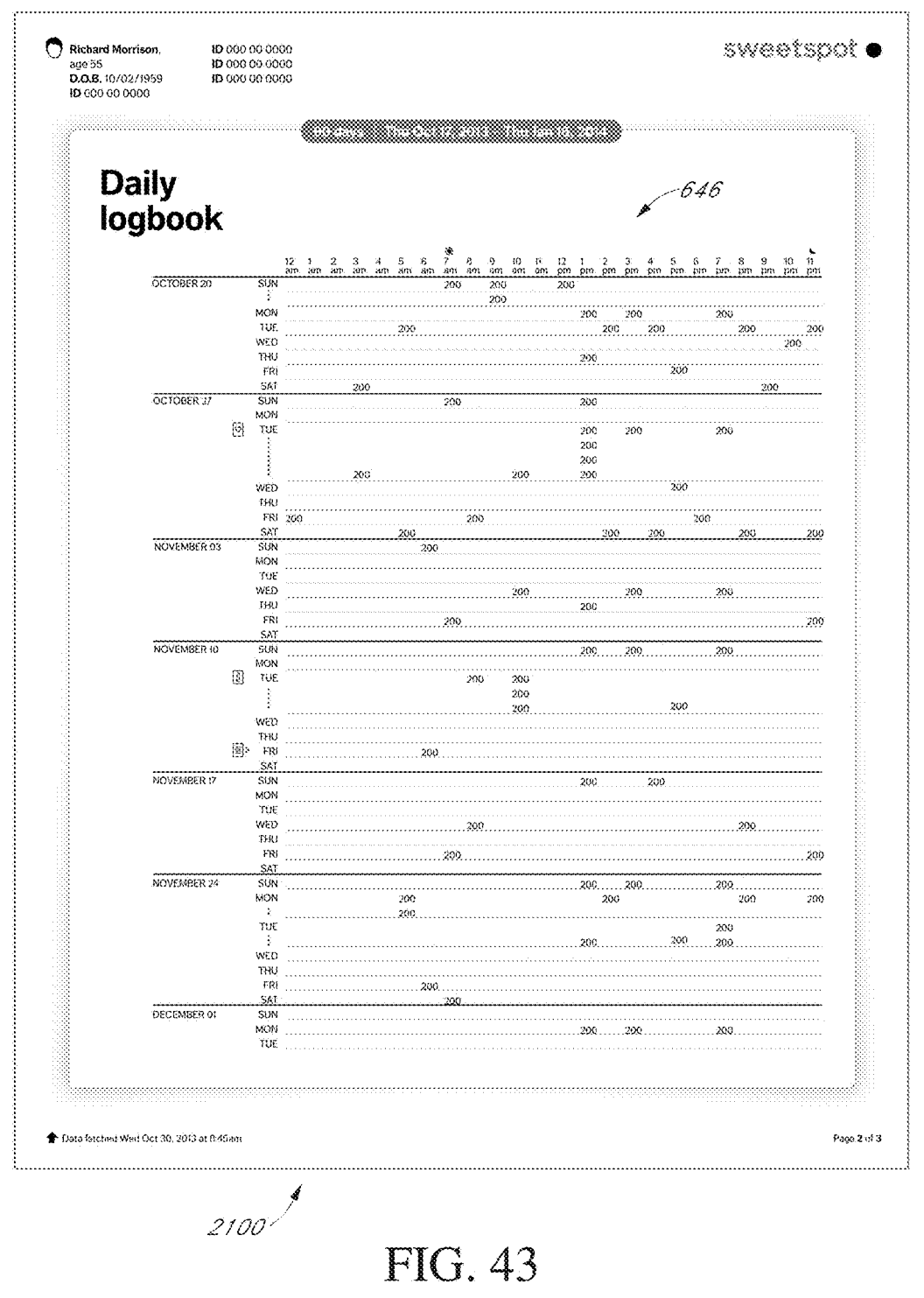

FIG. 43 illustrates a similar printed report 2100, but where only SMBG data is available. The printed report 2100 includes a series of daily views 646. As with the SMBG data in FIG. 39, numerical designations may accompany data points so as to allow a visual indication of the value. Such may be particularly important when the report is printed on a black and white printer, and thus where color cannot be used to indicate high or low values.

Figure 44:
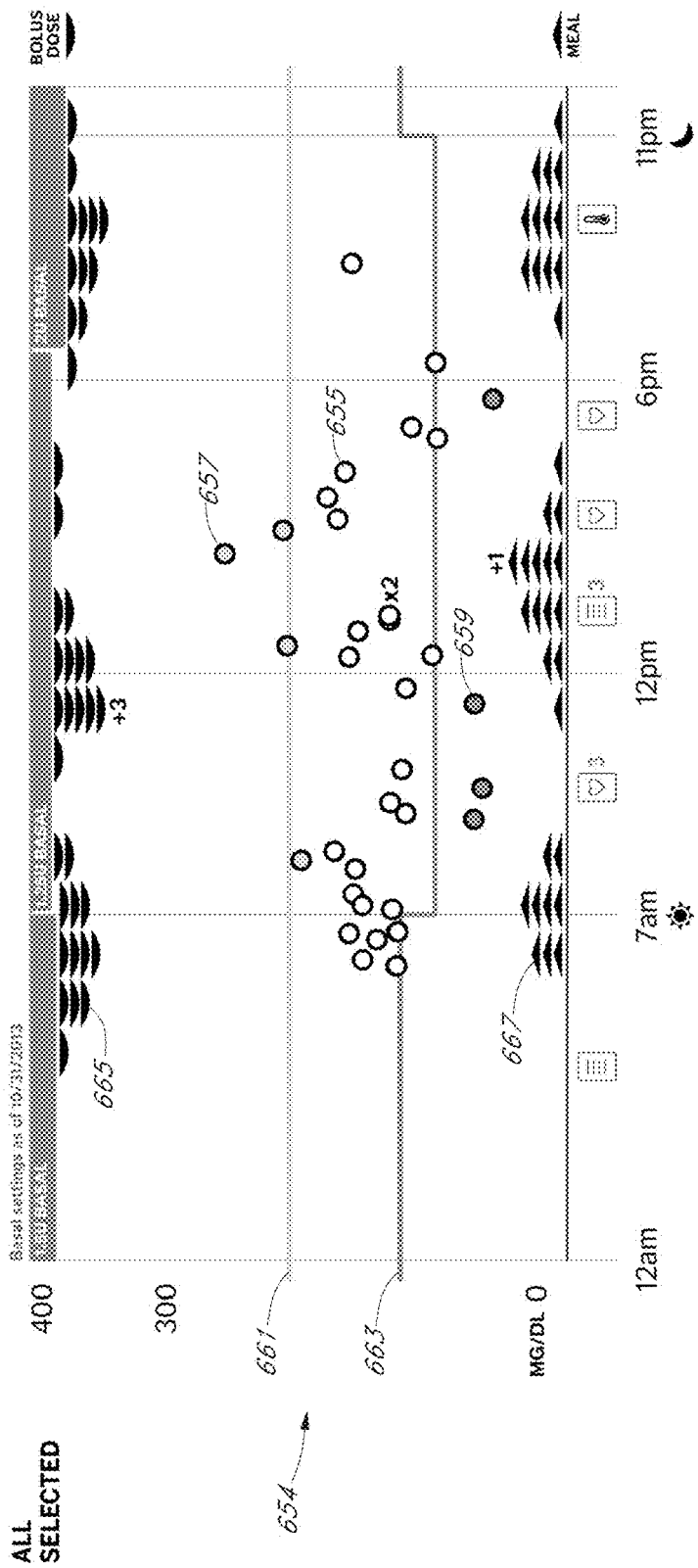
FIG. 44 shows an exemplary printed dynamic report, in particular illustrating BG data.

FIG. 44 illustrates another printed report for SMBG data, in which a chart 654 includes an upper threshold 661 and a lower threshold 663, as well as a number of points 655 within the target range, points 659 below the target range, and points 657 above the target range. As with prior figures, stacked boluses 665 may be seen, and the same adjacent to a basal level to indicate the additive or cumulative nature of a bolus above a basal rate. Carbohydrate ingestion or other meal intake is indicated by icons 667, which may be stacked according to their level and amount.

In both CGM and SMBG data, stacking icons corresponding to boluses and meal intake can help the user visualize the amount of each administered. In multi-day views of the same, stacking icons corresponding to boluses and meal intake (or providing histogram views of the same) may be accomplished by averaging the boluses and meal intake over the course of the multi-day time period. In single day views, the icons corresponding the boluses and meal intake can represent the amounts actually administered.

Figure 45:
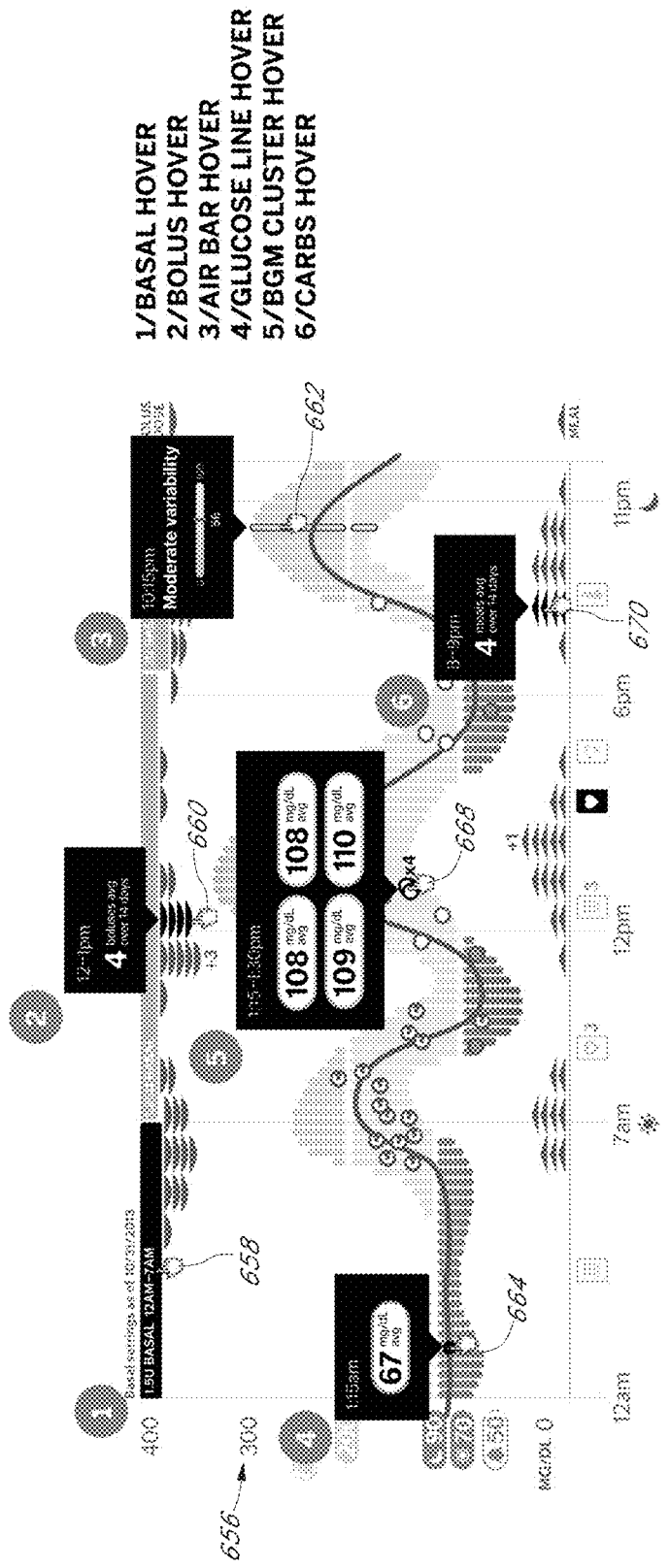
FIG. 45 illustrates an exemplary hovering process to obtain additional data within a dynamically generated or created report.

FIG. 45 shows a chart 656 within a report 2300 similar to that shown in FIG. 40, but where additional detail may be obtained in a displayed report by hovering over one or more points or areas. For example, hovering over area 658 may provide additional information about a basal rate of insulin, e.g., a particular rate over a relevant time period. Hovering over an area 660 may provide additional information about boluses provided, e.g., an average number of boluses per day. Hovering over area 662 may provide additional information about the variability indicated in the variability bars. Hovering over an area 664 may provide additional information about the mean glucose trace value at a given point in time. Hovering over an area 668 may provide additional information about SMBG measurement values if several are clustered in the hovered-over area. Hovering over an area 670 may provide additional information about carbohydrate ingestion as evidenced by a set of stacked icons.

Figure 46:
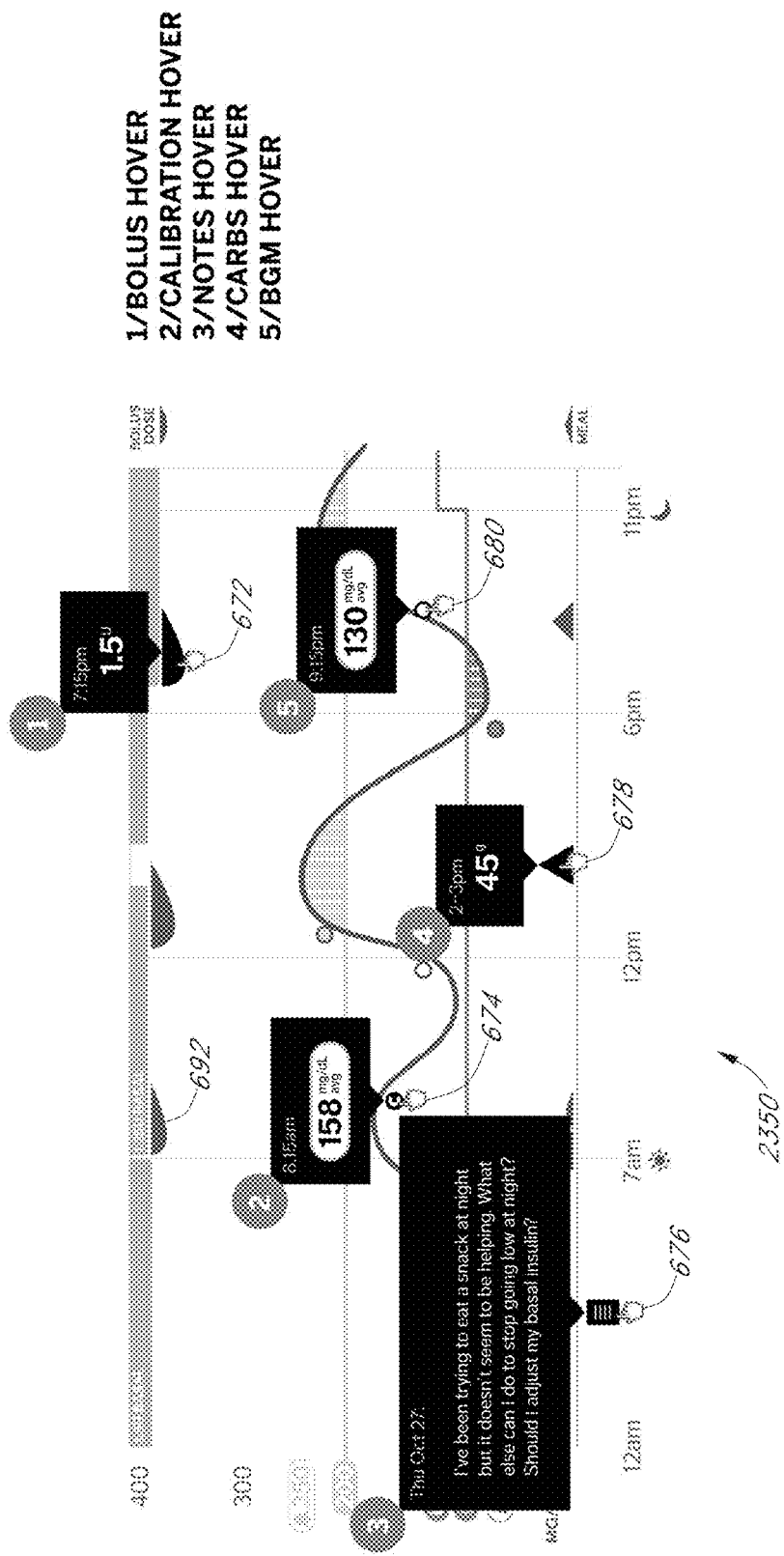
FIG. 46 illustrates another exemplary hovering process to obtain additional data within a dynamically generated or created report.

FIG. 46 shows a chart 2350 within a dynamically created report, again where additional information may be obtained by hovering over one or more points or areas. Hovering over an area 672 may provide additional information about boluses, e.g., an amount delivered in a particular bolus delivery episode. Hovering over an area 674 may provide specific information about a SMBG calibration value measurement, the same previously only having been displayed via a point on the chart. Hovering over an area 676 may provide a pop-up of a note written by a patient. Hovering over an area 678 may provide additional information about an indicated carbohydrate or meal intake, such as the time of day of ingestion, and amount ingested. Hovering over an area 680 may provide additional information about a particular blood glucose measurement, e.g., a measurement value. Note that in this case, the SMBG measurement is being used as a particular data value and not as a calibration for CGM. FIG. 46 also shows a bolus data in the form of an icon 692 having a tail as described above.

It is further noted that in all of the dynamic reports various events can be reflected in the charts by icons, and switches, such as radio buttons, may be employed to turn such icons and portrayed events on and off.

It is further noted that various charts may have a certain amount of data with which to populate data fields or create or generate data visualizations, but that there may be a gap in the data, or an outlier. In these cases, attempts may be made to smooth the data, e.g., using interpolated or predicted values, to allow the data visualization to still be dynamically generated. In some cases, using interpolated or predicted values may be indicated on the chart by a dotted line or other indicator to show that the same is not based (or only partially based) on actual data. Alternatively, a curve may simply be broken if the same is missing more than a predetermined number of consecutive data points. Such a predetermined number can be based on a timeframe being illustrated, e.g., for larger timeframes, a higher number of consecutive points can be missing. For shorter time frames, a lower number of consecutive points can be missing and still be portrayed in a data visualization.

Further to gaps in data, it is recognized that it can be problematic to detect patterns in that that contain data gaps. In particular, how should reporting system 150 treat data gaps when detecting patterns? Should the data gaps be considered as not contributing to a pattern, or assigned a value in some manner? In some implementations, reporting system 150 infers values of missing data, so as to be able to identify more patterns. A particular implementation of reporting system 150 uses a two-step process for inferring values of data gaps, described below.

First, reporting system 150 identifies data gaps and determines if the data gap is "span-able." "Span-able" can mean whether enough data exists to infer sufficiently reliable values for that missing data. Whether a gap is span-able can be based on a variety of criteria, including the number of missing data points, the reliability of the data points adjacent to the data gap, the clinical significance of the data points adjacent to the gap, and the like.

If the gap is determined to be span-able, then the reporting system 150 infers data values for the missing data values. A variety of statistical methods can be used to infer the missing values. In one implementation, a cone of possibilities is used to infer the missing values. That is, the data before and after the gap of data are used, in addition to rate of change information, to infer the most likely values of the missing data.

The inferred values of the missing data may then be used to detect patterns, as discussed herein. Further, the values may be displayed either as gaps or as values in reports. In some implementations, a user can select a filter that either allows the display of inferred, missing data points, or prevents the display of missing data points. Further, the missing, inferred data points can be visually displayed differently than non-missing data points, such as in a grey color instead of a black color.

System 150 can also analyze the inferred data to determine if the inferred data may be clinically significant. For example, whether inferred data changes a clinically significant detected pattern, system 150 can decide to not use the inferred data, include a message to a user of the report that the detected pattern is based on inferred data and/or modify the inferred data to provide a more conservative diagnosis. In some implementations, the clinical significant determination can be based on whether other possible inferred interpretations (e.g., using a cone of possibilities analysis) of the missing data would change the clinical significance of a determination (e.g. detected pattern). As a non-limiting example, system 150 may, under a first inference using a cone of possibilities analysis, infer data points in a missing-data gap that result in no detected night-time low pattern, but, in a second, different inference using the cone of possibilities analysis, results in an identification of a reoccurring night-time low pattern. In such a situation, the system may use the more conservative inferred data that results in the detected night-time low pattern detection and/or include a message in the report that the missing data affected the pattern detection analysis.

Automatic Generation of Reports and Notifications

As can be appreciated, the above described reports can be extremely valuable to a patient or health care provider in managing a patient's diabetes or other health condition. However, a patient or healthcare provider may not remember to view reports on a periodic basis, or be aware of a time when viewing a report could add particular value to managing the patient's condition. Accordingly, some implementations of reporting system 150 automatically generate a report and/or notify a user (e.g., patient or health care provider) to view a report.

In some implementations, a user of reporting system 150 can use settings 147 (FIG. 2B) to trigger reporting system 150 to send a notification (such as via SMS text message, email and the like) to user regarding a report. The report can be a report pre-designated by the user; for example, a one-week or one-moth report. The reporting system 150 can trigger the notification automatically based on a reoccurring timeframe (e.g., once every week, once every month, a time period before an event, such as a meal, doctor's appointment or calendared vacation), or automatically based on reporting system 150 detecting one or more patterns or other conditions based on the patient's data. The notification can comprise an electronic version of the designated report (e.g., a PDF) that the user can view, or can contain an electronic link that, when selected by a user, launches an application running on the user's device causing the report to be displayed on the user's device. The notification can alternatively or additionally include a textual description describing a result of the report, such as "Congratulations, you have fewer detected nighttime lows this week than last week!", should reporting system 150 detect such a situation.

As one non-limiting, illustrative example, a user can first generate a report using reporting system 150 comparing a current week's data to a previous week's data. Reporting system 150 then allows the user, through settings 147, for example, or at the time of printing the report, as another example, to select an option to set up automatic reoccurring notifications. The automatic reoccurring notifications can further allow the user to select a timeframe, such as once a week. If automatic, reoccurring notifications are enabled, then reporting system automatically notifies the user via the user's preferred notification method (provided in settings 147) of the report. The notification can also include an electronic version of a newly generated report comparing the now current week's data to the now past week's date, which are both now one week later than the originally generated report discussed earlier.

As further illustrative example, a user can use reporting system 150 to set up a notification based on a detected pattern, such as nighttime lows. Here, reporting system 150 can automatically send a notification to the user if a predetermined number of nighttime low events are detected over a predetermined amount of time, such as two nighttime low events over a one week period. The notification can include a textual explanation of the detected pattern as well as an electronic version of a report illustrating the events or an electronic link to the report.

General Description of a Glucose Monitoring System

While the systems and methods according to present principles may be employed within any number of health monitoring environments, one particular embodiment may be employed in glucose monitoring and the dynamic generation of reports therefore. Other types of analytes which may be monitored are listed elsewhere in this specification. A particular monitor system for the analyte of glucose is described below.

A glucose sensor may be employed that measures a concentration of glucose or a substance indicative of the concentration or presence of the glucose. In some embodiments, the glucose sensor is a continuous device, for example a subcutaneous, transdermal, or intravascular device. In some embodiments, the device can analyze a plurality of intermittent blood samples. The glucose sensor can use any method of glucose measurement, including enzymatic, chemical, physical, electrochemical, spectrophotometric, polarimetric, calorimetric, iontophoretic, radiometric, and the like.

The glucose sensor can use any known method, including invasive, minimally invasive, and non-invasive sensing techniques, to provide a data stream indicative of the concentration of glucose in a host. The data stream is typically a raw data signal that is transformed to provide a useful value of glucose to a user, such as a patient or clinician, who may be using the sensor.

Glucose Sensor

The glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., clinician), who may be using the sensor.

Although much of the description and examples are drawn to a glucose sensor capable of measuring the concentration of glucose in a host, the systems and methods of embodiments can be applied to any measurable analyte, a list of appropriate analytes noted above. Some exemplary embodiments described below utilize an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. Patent Publication No. 2008/0119703, U.S. Patent Publication No. 2008/0108942, and U.S. Pat. No. 7,828,728. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

Details of sensors, sensor electronics, and signal receiver and display components may be as described in the applications incorporated by reference above, as well as in, e.g., US Patent Publication No. 2013/0078912, incorporated by reference in its entirety.

Receiver/Monitor

Figure 47:
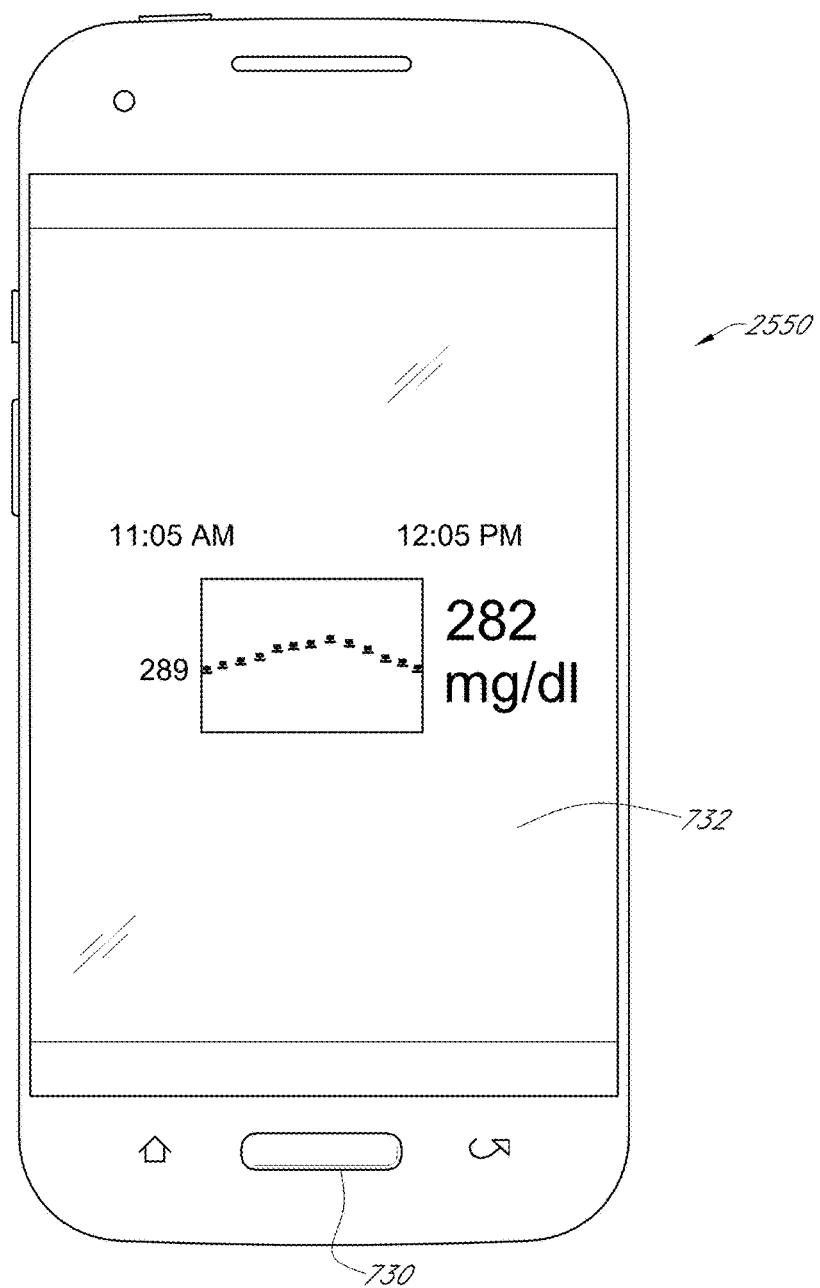
FIG. 47 is a schematic view of a receiver or host (or caregiver/patient) monitor, in the form of a smart phone.

FIG. 47 is a schematic view of a receiver or monitor 2550 including representations of estimated glucose values on its user interface. The monitor 2550 comprises systems to receive, process, and display sensor data from the glucose sensor (e.g., 2450), such as described herein. Particularly, the monitor 2550 can be a mobile phone type device, for example, and comprise a user interface that has a physical button 730 and a display screen 732, as well as one or more input/output (I/O) devices, such as one or more buttons and/or switches, which when activated or clicked perform one or more functions. In the illustrated embodiment, the electronic device is a smartphone, and the display 732 comprises a touchscreen, which also functions as an I/O device. In some embodiments, the user interface can also include a keyboard, a speaker, and a vibrator. The functions of the monitor or smart phone can also be implemented as functions within an application running on a tablet computer, laptop computer, desktop computer, or like device. In other embodiments, the receiver may comprise a device or devices other than a smartphone, such as a smartwatch, a tablet computer, a mini-tablet computer, a handheld personal digital assistant (PDA), a game console, a multimedia player, a wearable device, such as those described above, a screen in an automobile or other vehicle, a dedicated receiver device, etc. In any case, the display screen of such computing environments may be employed to display dynamically created reports, and the computing environment may further be employed to print the dynamic reports noted herein.

Figure 48:
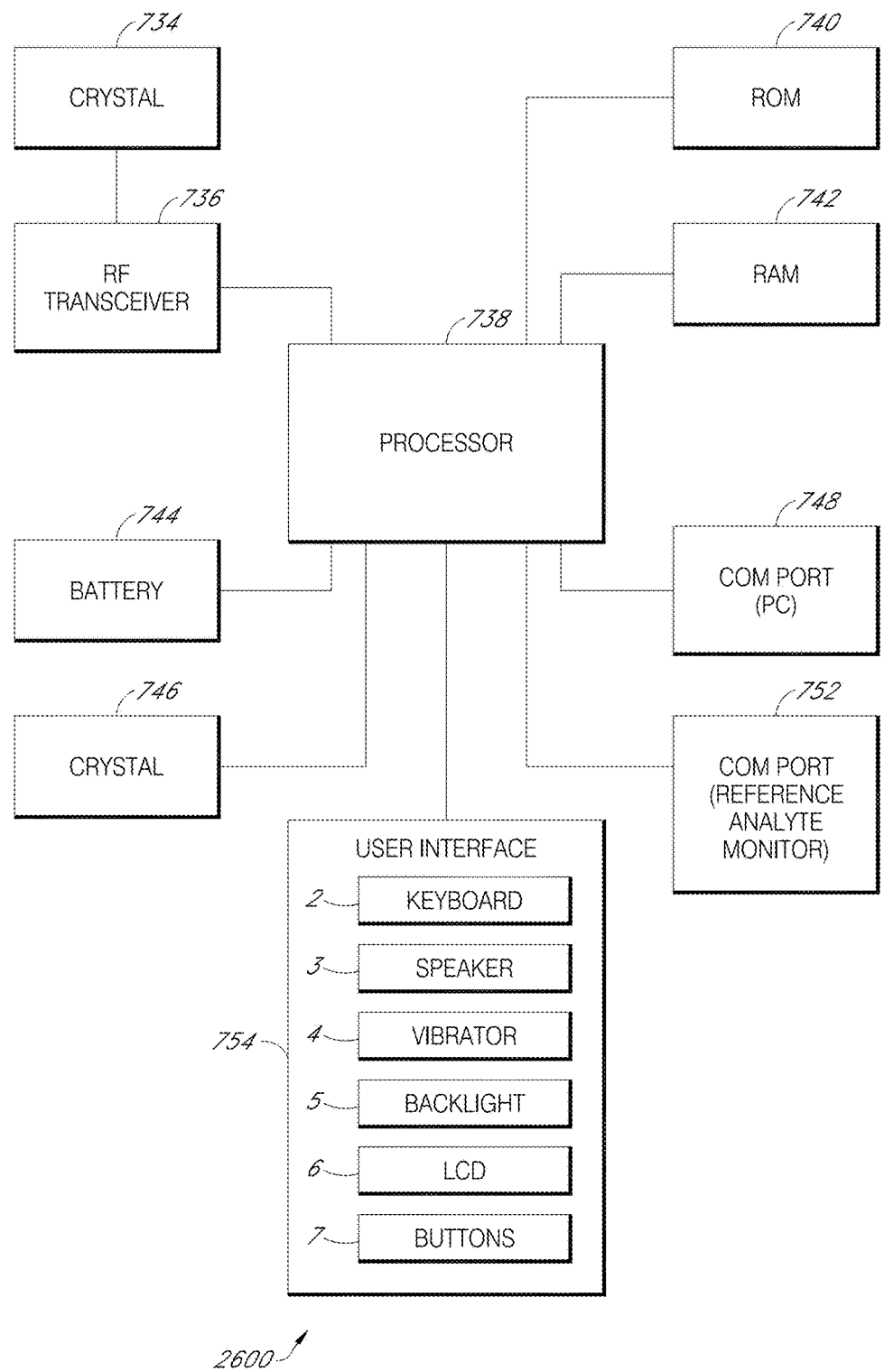
FIG. 48 is a block diagram of receiver electronics in one embodiment.

FIG. 48 is a block diagram that illustrates one possible configuration of the monitor electronics, e.g., a smart phone. It is noted that the monitor can comprise a configuration such as described with reference to FIG. 47, above. Alternatively, the monitor can comprise other configurations, including a desktop computer, laptop computer, a personal digital assistant (PDA), a server (local or remote to the receiver), and the like. In some embodiments, the receiver can be adapted to connect (via wired or wireless connection) to a desktop computer, laptop computer, PDA, server (local or remote to the receiver), and the like, in order to download data from the receiver. In some alternative embodiments, the monitor and/or monitor electronics can be housed within or directly connected to the sensor (e.g., 2450) in a manner that allows sensor and receiver electronics to work directly together and/or share data processing resources. Accordingly, the receiver's electronics can be generally referred to as a "computer system."

A quartz crystal 734 is operatively connected to an RF transceiver 736 that together function to receive and synchronize data streams (e.g., raw data streams transmitted from the RF transceiver). Once received, a processor 738 processes the signals, such as described below.

The processor 738, also referred to as the processor module, is the central control unit that performs the processing, such as storing data, analyzing data streams, calibrating analyte sensor data, predicting analyte values, comparing predicted analyte values with corresponding measured analyte values, analyzing a variation of predicted analyte values, downloading data, and controlling the user interface, e.g., generating dynamic reports, by providing analyte values, prompts, messages, warnings, alarms, data fields, data visualizations, and the like. The processor includes hardware and software that performs the processing described herein, for example flash memory provides permanent or semi-permanent storage of data, storing data such as sensor ID, receiver ID, and programming to process data streams (for example, programming for performing prediction and other algorithms described elsewhere herein) and random access memory (RAM) stores the system's cache memory and is helpful in data processing.

In one exemplary embodiment, the processor is a microprocessor that provides the processing, such as calibration algorithms stored within a ROM 740. The ROM 740 is operatively connected to the processor 738 and provides semi-permanent storage of data, storing data such as receiver ID and programming to process data streams (e.g., programming for performing calibration and other algorithms described elsewhere herein). In this exemplary embodiment, a RAM 742 is used for the system's cache memory and is helpful in data processing.

A battery 744 is operatively connected to the processor 738 and provides power for the receiver. In one embodiment, the battery is a standard AAA alkaline battery, however any appropriately sized and powered battery can be used. In some embodiments, a plurality of batteries can be used to power the system. A quartz crystal 746 is operatively connected to the processor 738 and maintains system time for the computer system as a whole.

A user interface 754 comprises a keyboard 2, speaker 3, vibrator 4, backlight 5, liquid crystal display (LCD 6), and one or more buttons 7, which may be implemented as physical buttons or buttons on a touchscreen interface. The components that comprise the user interface 754 provide controls to interact with the user. The keyboard 2 can allow, for example, input of user information about himself/herself, such as mealtime, exercise, insulin administration, and reference glucose values. The speaker 3 can provide, for example, audible signals or alerts for conditions such as present and/or predicted hyper- and hypoglycemic conditions. The vibrator 4 can provide, for example, tactile signals or alerts for reasons such as described with reference to the speaker, above. The backlight 5 can be provided, for example, to aid the user in reading the LCD in low light conditions. The LCD 6 can be provided, for example, to provide the user with visual data output such as is illustrated in FIG. 50, or the data fields and data visualizations described above. The buttons 7 can provide for toggle, menu selection, option selection, mode selection, and reset, for example.

In some embodiments, prompts or messages can be displayed on the user interface to convey information to the user, such as requests for reference analyte values, therapy recommendations, deviation of the measured analyte values from the predicted analyte values, and the like. Additionally, prompts can be displayed to guide the user through calibration or trouble-shooting of the calibration.

In some implementations, the continuous analyte sensor system includes a DexCom G4® Platinum glucose sensor and transmitter commercially available from DexCom, Inc., for continuously monitoring a host's glucose levels.

In some embodiments, the system may execute various applications, for example, a CGM application, which may be downloaded to the receiver or other electronic device over the Internet and/or a cellular network, and the like. Data for various applications may be shared between the device and one or more other devices/systems, and stored by cloud or network storage and/or on one or more other devices/systems. The data so stored may form the basis of the dynamic reports described above.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIG. 48) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

The system and method may be fully implemented in any number of computing devices. Typically, instructions are laid out on computer readable media, generally non-transitory, and these instructions are sufficient to allow a processor in the computing device to implement the method. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file-storing medium. The outputs may be delivered to a user by way of a video graphics card, graphics processor, or integrated graphics chipset coupled to a display that may be seen by a user. Alternatively, a printer may be employed to output hard copies of the results including the formats described above with respect to FIGS. 35-44. Given this teaching, any number of other tangible outputs will also be understood to be contemplated. For example, outputs may be stored on a memory chip, hard drive, flash drives, flash memory, optical media, magnetic media, or any other type of output. It should also be noted that the aspects may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi-connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the above system where, for some implementations, multiple sources of data are contemplated, the plural inputs may allow plural users to input relevant data at the same time.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred, "desired," or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A computer-implemented method for interfacing a computing device and a user to display data pertaining to user intake of one or more units of a substance, the method comprising:
    receiving, a first set of data about a user, the first set of data measured using a continuous analyte sensor, the first set of data representing an analyte concentration value with respect to time;
    receiving a second set of data about a user, the second set of data representing user intake of a substance with respect to time;
    generating a screen for display at the computing device, the screen comprising:
        a graph having a horizontal axis indicating time and a vertical axis;
        a first indicator indicating at least a portion of the first set of data; and
        a second indicator indicating at least a portion of the second set of data, wherein the second indicator is positioned on the graph to indicate how the user intake of the substance tends to increase the analyte concentration value and is displayed below the first indicator, or the second indicator is positioned on the graph to indicate how the user intake of the substance tends to decrease the analyte concentration value and is displayed above the first indicator; and
    causing the screen to be displayed at the computing device.

2. The method of claim 1, wherein the second set of data further represents user intake of one or more units of the substance with respect to time, and wherein the second indicator is displayed such that, for substances that tend to increase the analyte concentration value, the second indicator comprises individual units with a quantity according to the user intake and below the first indicator, and, for substances that tend to decrease the analyte concentration value, the second indicator comprises individual units with a quantity according to the user intake and above the first indicator.

3. The method of claim 2, wherein the first set of data represents a signal trace of glucose concentration and the second set of data represents insulin intake and/or carbohydrate ingestion, wherein the second indicator comprises units representing insulin intake that are displayed above the first indicator, whereby the units representing insulin intake appear to push down on the signal trace, and wherein the second indicator comprises units representing carbohydrate ingestion that are displayed below the first indicator, whereby the units representing carbohydrate ingestion appear to push up on the signal trace.

4. The method of claim 1, further comprising:
    receiving a basal value of a medicament, and
    modifying the second indicator based on the basal value on the screen.

5. A method for interfacing a computing device and a user to display data pertaining to user glucose concentration values, the method comprising:
    receiving a first set of data about a user, the first set of data measured using a continuous analyte sensor, the first set of data representing a glucose concentration value with respect to time;
    receiving a second set of data about a user, the second set of data representing user intake of a substance with respect to time;
    receiving at least one threshold value;
    generating a screen for display at the computing device, the screen comprising a graph, a first indicator based on at least a portion of the first set of data, and a second indicator based on at least a portion of the second set of data, wherein the graph has an abscissa indicating time and an ordinate indicating the glucose concentration value, wherein the first indicator is arranged to indicate values of the glucose concentration value above the at least one threshold value on the graph using a first format and to indicate values of the glucose concentration not above the at least one threshold value on the graph using a second format that is different than the first format,
    wherein the at least one threshold value varies with respect to time, the varying to reflect biological processing of insulin or carbohydrates within a host; and
    wherein the second indicator is arranged to indicate how the user intake of the substance tends to increase the glucose concentration value and is displayed below the first indicator, or the second indicator is arranged to indicate how the user intake of the substance tends to decrease the glucose concentration value and is displayed above the first indicator.

6. The method of claim 5, further comprising displaying a third indicator of the received at least one threshold value along with the first indicator and the second indicator.

7. The method claim 5, further comprising:
    receiving at least one alert value; and
    displaying an indication of the at least one alert value along with the first indicator and the second indicator.

8. The method of claim 5, further comprising:
    receiving at least one alarm value; and
    displaying an indication of the at least one alarm value along with the first indicator and the second indicator.

9. The method of claim 5, wherein the at least one threshold value varies periodically over time.

10. The method of claim 9, wherein the period is one day.

11. The method of claim 5, wherein the at least one threshold value is entered by a user.

12. A system for interfacing with a user to display data pertaining to user intake of one or more units of a substance, comprising:
    a continuous analyte sensor device configured for receiving a first set of data about a user, the first set of data representing an analyte concentration value with respect to time, and receiving a second set of data about a user, the second set of data representing user intake of a substance with respect to time;
    a processor configured for generating a screen, the screen comprising:
        a graph having a horizontal axis indicating time and a vertical axis;
        a first indicator indicating at least a portion of the first set of data; and
        a second indicator indicating at least a portion of the second set of data, wherein the second indicator is positioned on the graph to indicate how the user intake of the substance tends to increase the analyte concentration value and is displayed below the first indicator or the second indicator is positioned on the graph to indicate how the user intake of the substance tends to decrease the analyte concentration value and is displayed above the first indicator; and a display configured for displaying the screen.

13. The system of claim 12, wherein the second set of data further represents user intake of one or more units of the substance with respect to time and wherein the second indicator is displayed such that, for substances that tend to increase the analyte concentration value, the second indicator comprises individual units with a quantity according to the user intake and below the first indicator, and, for substances that tend to decrease the analyte concentration value, the second indicator comprises as individual units with a quantity according to the user intake and above the first indicator.

14. The system of claim 13, wherein the first set of data represents a signal trace of glucose concentration and the second set of data represents insulin intake and/or carbohydrate ingestion, wherein the second indicator comprises units representing insulin intake that are displayed above the first indicator, whereby the units representing insulin intake appear to push down on the signal trace, and wherein the second indicator also comprises units representing carbohydrate ingestion that are displayed below the first indicator, whereby the units representing carbohydrate ingestion appear to push up on the signal trace.

15. The system of claim 12, further comprising:
a processor configured for receiving a basal value of a medicament, and
modifying the second indicator based on.

16. A system for interfacing with a user to display data pertaining to user glucose concentration values, comprising:
a continuous glucose sensor device configured for generating a first set of data about a user, the first set of data representing a glucose concentration value with respect to time;
a processor configured for:
receiving the first set of data;
receiving at least one threshold value;
receiving a second set of data about a user, the second set of data representing user intake of a substance with respect to time; and
generating a screen for display at the computing device, the screen comprising a graph, a first indicator based on at least a portion of the first set of data, and a second indicator based on at least a portion of the second set of data,
wherein the graph has an abscissa indicating time and an ordinate indicating the glucose concentration value,
wherein the first indicator is arranged to indicate values of the glucose concentration value above the at least one threshold value on the graph using a first format and to indicate values of the glucose concentration not above the at least one threshold value using a second format that is different from the first format, and
wherein the second indicator as arranged to indicate how the user intake of the substance tends to increase the glucose concentration value and is displayed below the first indicator or the second indicator is arranged to indicate how the user intake of the substance tends to decrease the glucose concentration value and is displayed above the first indicator; and
a display configured for displaying the screen.

17. The system of claim 16, wherein the display is configured for displaying a third indicator of the received at least one threshold value along with the first indicator and the second indicator.

18. The system of claim 16, further comprising:
a continuous glucose sensor configured for receiving at least one alert value; and
a display configured for displaying an indication of the at least one alert value along with the first indicator and the second indicator.

19. The system of claim 16, further comprising:
a continuous glucose sensor configured for receiving at least one alarm value; and
a display configured for displaying an indication of the at least one alarm value along with the first indicator and the second indicator.

20. The system of claim 16, wherein the at least one threshold value varies periodically over time.

21. The system of claim 20, wherein the period is one day.

22. The system of claim 16, wherein the at least one threshold value is entered by a user.

* * * * *

UNITED STATES PATENT AND TRADEMARK OFFICE
CERTIFICATE OF CORRECTION

PATENT NO. : 10,467,780 B2
APPLICATION NO. : 14/874296
DATED : November 5, 2019
INVENTOR(S) : Georgios Zamanakos It is certified that error appears in the above-identified patent and that said Letters Patent is hereby corrected as shown below:

In the Specification

In Column 17, Line 23, delete "andrenostenedione;" and insert -- androstenedione; --.

In Column 17, Line 39, delete "diptheria" and insert -- diphtheria --.

In Column 17, Line 46, delete "perioxidase;" and insert -- peroxidase; --.

In Column 17, Line 55, delete "sissomicin;" and insert -- sisomicin; --.

In Column 17, Line 59, delete "duodenalisa," and insert -- duodenalis, --.

In Column 17, Line 67, delete "Trepenoma pallidium," and insert -- Treponema pallidum, --.

In Column 18, Line 1, delete "stomatis" and insert -- stomatitis --.

In Column 58, Line 37, delete "may be" and insert -- maybe --.

In the Claims

In Column 62, Line 38, Claim 7, after "method" insert -- of --.

In Column 63, Line 34, Claim 15, delete "on." and insert -- on the basal value. --.

Signed and Sealed this
Eleventh Day of February, 2020

Andrei Iancu
*Director of the United States Patent and Trademark Office*